(12) United States Patent
Popov et al.

(10) Patent No.: US 9,737,491 B2
(45) Date of Patent: *Aug. 22, 2017

(54) NANOCRYSTALS, COMPOSITIONS, AND METHODS THAT AID PARTICLE TRANSPORT IN MUCUS

(71) Applicant: The Johns Hopkins University, Baltimore, MD (US)

(72) Inventors: Alexey Popov, Waltham, MA (US); Elizabeth M. Enlow, Waltham, MA (US); James Bourassa, Somerville, MA (US); Colin R. Gardner, Concord, MA (US); Hongming Chen, Belmont, MA (US); Laura M. Ensign, Towson, MD (US); Samuel K. Lai, Carrboro, NC (US); Tao Yu, Baltimore, MD (US); Justin Hanes, Baltimore, MD (US); Ming Yang, Towson, MD (US)

(73) Assignee: The Johns Hopkins University, Baltimore, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 15/354,704

(22) Filed: Nov. 17, 2016

(65) Prior Publication Data
US 2017/0128378 A1    May 11, 2017

Related U.S. Application Data

(63) Continuation of application No. 15/187,552, filed on Jun. 20, 2016, now Pat. No. 9,532,955, which is a continuation of application No. 14/731,921, filed on Jun. 5, 2015, now Pat. No. 9,393,212, which is a continuation of application No. 13/886,493, filed on May 3, 2013, now Pat. No. 9,056,057.

(60) Provisional application No. 61/642,227, filed on May 3, 2012.

(51) Int. Cl.
| | |
|---|---|
| A61K 9/50 | (2006.01) |
| A61K 31/56 | (2006.01) |
| A61K 31/635 | (2006.01) |
| A61K 31/496 | (2006.01) |
| A61K 31/573 | (2006.01) |
| A61K 31/58 | (2006.01) |
| A61K 31/405 | (2006.01) |
| A61K 31/12 | (2006.01) |
| A61K 31/409 | (2006.01) |
| A61K 31/675 | (2006.01) |
| A61K 31/522 | (2006.01) |

(52) U.S. Cl.
CPC ............ *A61K 9/5031* (2013.01); *A61K 31/12* (2013.01); *A61K 31/405* (2013.01); *A61K 31/409* (2013.01); *A61K 31/496* (2013.01); *A61K 31/522* (2013.01); *A61K 31/56* (2013.01); *A61K 31/573* (2013.01); *A61K 31/58* (2013.01); *A61K 31/635* (2013.01); *A61K 31/675* (2013.01)

(58) Field of Classification Search
CPC .............................. A61K 47/34; A61K 9/5089
See application file for complete search history.

(56) References Cited

U.S. PATENT DOCUMENTS

| | | | |
|---|---|---|---|
| 4,910,225 A | 3/1990 | Ogawa et al. | |
| 4,996,335 A | 2/1991 | Bodor | |
| 5,298,262 A | 3/1994 | Na et al. | |
| 5,364,884 A | 11/1994 | Varma et al. | |
| 5,429,824 A | 7/1995 | June | |
| 5,518,187 A | 5/1996 | Bruno et al. | |
| 5,534,259 A | 7/1996 | Zalipsky et al. | |
| 5,540,930 A | 7/1996 | Guy | |
| 5,567,435 A | 10/1996 | Hubbell | |
| 5,576,311 A | 11/1996 | Guy | |
| 5,696,298 A | 12/1997 | Emanuele | |
| 5,718,388 A | 2/1998 | Czekai et al. | |
| 5,747,061 A | 5/1998 | Aselem et al. | |
| 5,862,999 A | 1/1999 | Czekai et al. | |

(Continued)

FOREIGN PATENT DOCUMENTS

| | | |
|---|---|---|
| AU | 2006220411 A1 | 10/2006 |
| CA | 2 564 982 A1 | 11/2005 |

(Continued)

OTHER PUBLICATIONS

Lutrol "Lutrol and Lutrol F-Grades" BASF, Apr. 2010.*

(Continued)

*Primary Examiner* — Timothy Thomas
*Assistant Examiner* — Andrew S Rosenthal
(74) *Attorney, Agent, or Firm* — K&L Gates LLP; Louis C. Cullman; Michelle Glasky Bergman

(57) ABSTRACT

Nanocrystals, compositions, and methods that aid particle transport in mucus are provided. In some embodiments, the compositions and methods involve making mucus-penetrating particles (MPP) without any polymeric carriers, or with minimal use of polymeric carriers. The compositions and methods may include, in some embodiments, modifying the surface coatings of particles formed of pharmaceutical agents that have a low water solubility. Such methods and compositions can be used to achieve efficient transport of particles of pharmaceutical agents though mucus barriers in the body for a wide spectrum of applications, including drug delivery, imaging, and diagnostic applications. In certain embodiments, a pharmaceutical composition including such particles is well-suited for administration routes involving the particles passing through a mucosal barrier.

21 Claims, 29 Drawing Sheets

(56) References Cited

U.S. PATENT DOCUMENTS

| | | |
|---|---|---|
| 5,869,130 A | 2/1999 | Ferrier |
| 5,922,357 A | 7/1999 | Coombes et al. |
| 6,106,819 A | 8/2000 | Sucher |
| 6,153,607 A | 11/2000 | Pflugfelder et al. |
| 6,165,509 A | 12/2000 | Hoffman et al. |
| 6,197,346 B1 | 3/2001 | Mathiowitz et al. |
| 6,217,908 B1 | 4/2001 | Mathiowitz et al. |
| 6,235,313 B1 | 5/2001 | Mathiowitz et al. |
| 6,264,981 B1 | 7/2001 | Zhang et al. |
| 6,270,806 B1 | 8/2001 | Liversidge |
| 6,287,588 B1 | 9/2001 | Shih |
| 6,365,187 B2 | 4/2002 | Mathiowitz et al. |
| 6,372,246 B1 | 4/2002 | Wei et al. |
| 6,413,539 B1 | 7/2002 | Shalaby |
| 6,432,381 B2 | 8/2002 | Liversidge |
| 6,495,164 B1 | 12/2002 | Ramstack |
| 6,589,549 B2 | 7/2003 | Shih |
| 6,627,228 B1 | 9/2003 | Milstein et al. |
| 6,706,289 B2 | 3/2004 | Lewis et al. |
| 7,153,524 B2 | 12/2006 | Yoshihara et al. |
| 7,534,449 B2 | 5/2009 | Saltzman et al. |
| 7,550,441 B2 | 6/2009 | Farokhzad et al. |
| 7,795,237 B2 * | 9/2010 | Ahmed ............... A61K 9/14 424/464 |
| 7,842,232 B2 | 11/2010 | Bosch et al. |
| 7,906,136 B2 | 3/2011 | Wong et al. |
| 8,354,476 B2 | 1/2013 | Hanes |
| 8,409,607 B2 | 4/2013 | Hughes |
| 8,465,778 B2 | 6/2013 | Hughes |
| 8,481,069 B2 | 7/2013 | Hughes |
| 8,512,738 B2 | 8/2013 | Edelman |
| 8,628,801 B2 | 1/2014 | Garreta |
| 8,632,809 B2 | 1/2014 | Asgharian |
| 8,663,674 B2 | 3/2014 | Wen |
| 8,889,193 B2 | 11/2014 | McDonnell |
| 8,911,768 B2 | 12/2014 | Whitcup |
| 8,957,034 B2 | 2/2015 | Hanes |
| 8,962,577 B2 | 2/2015 | Hanes |
| 9,056,057 B2 | 6/2015 | Popov |
| 2002/0035264 A1 | 3/2002 | Kararli |
| 2004/0076670 A1 | 4/2004 | Klinksiek et al. |
| 2004/0234611 A1 | 11/2004 | Ahlheim |
| 2005/0009910 A1 | 1/2005 | Hughes |
| 2005/0058603 A1 | 3/2005 | Gao et al. |
| 2005/0191359 A1 | 9/2005 | Goldshtein et al. |
| 2005/0266067 A1 | 12/2005 | Sengupta et al. |
| 2005/0266090 A1 | 12/2005 | Prokop et al. |
| 2006/0257487 A1 | 11/2006 | Owen et al. |
| 2007/0071756 A1 | 3/2007 | Peyman |
| 2007/0093461 A1 | 4/2007 | Shafiee |
| 2007/0141143 A1 | 6/2007 | Smithey |
| 2007/0149480 A1 | 6/2007 | Ghosh et al. |
| 2007/0149593 A1 | 6/2007 | Ghosh |
| 2007/0178051 A1 | 8/2007 | Pruitt et al. |
| 2007/0231360 A1 | 10/2007 | Peyman |
| 2007/0249536 A1 | 10/2007 | Ma |
| 2007/0299044 A1 | 12/2007 | Farng et al. |
| 2008/0086199 A1 | 4/2008 | Dave |
| 2008/0159984 A1 | 7/2008 | Ben-Sasson |
| 2008/0166411 A1 | 7/2008 | Shah |
| 2008/0175887 A1 | 7/2008 | Wang |
| 2008/0194468 A1 | 8/2008 | Bodor |
| 2008/0248125 A1 | 10/2008 | Irache Garreta et al. |
| 2008/0267876 A1 | 10/2008 | Benita et al. |
| 2008/0305172 A1 | 12/2008 | Ahlheim |
| 2009/0087493 A1 | 4/2009 | Dai et al. |
| 2009/0203709 A1 | 8/2009 | Steinberg |
| 2009/0247604 A1 | 10/2009 | Tang |
| 2010/0076045 A1 | 3/2010 | Castillo et al. |
| 2010/0215580 A1 | 8/2010 | Hanes |
| 2010/0222308 A1 | 9/2010 | Zhang |
| 2010/0227905 A1 | 9/2010 | Kabra |
| 2010/0290983 A1 | 11/2010 | Rabinow et al. |
| 2012/0028910 A1 | 2/2012 | Combal |
| 2012/0052041 A1 | 3/2012 | Basu |
| 2012/0121718 A1 * | 5/2012 | Lai ............... A61K 45/06 424/497 |
| 2012/0157499 A1 | 6/2012 | Hughes |
| 2012/0252756 A1 | 10/2012 | Coffey et al. |
| 2012/0269894 A1 | 10/2012 | Ahlheim |
| 2012/0289486 A1 | 11/2012 | Bodor |
| 2013/0071349 A1 | 3/2013 | Robinson |
| 2013/0122064 A1 | 5/2013 | Ahlheim |
| 2013/0164343 A1 | 6/2013 | Hanes |
| 2013/0183244 A1 | 7/2013 | Hanes |
| 2013/0217657 A1 | 8/2013 | Lindstrom |
| 2013/0236556 A1 | 9/2013 | Lai |
| 2013/0272994 A1 | 10/2013 | Hanes |
| 2013/0274217 A1 | 10/2013 | Hanes |
| 2013/0316001 A1 | 11/2013 | Popov |
| 2013/0316009 A1 | 11/2013 | Popov |
| 2013/0323313 A1 | 12/2013 | Suk |
| 2014/0031408 A1 | 1/2014 | Edelman |
| 2014/0107025 A1 | 4/2014 | Wirostko |
| 2014/0178475 A1 | 6/2014 | Figueiredo |
| 2014/0248358 A1 | 9/2014 | Figueiredo |
| 2014/0249158 A1 | 9/2014 | Figueiredo |
| 2014/0276482 A1 | 9/2014 | Astafieva |
| 2014/0294986 A1 | 10/2014 | Liu |
| 2014/0329913 A1 | 11/2014 | Hanes |
| 2015/0044270 A1 | 2/2015 | McDonnell |
| 2015/0086484 A1 | 3/2015 | Hanes |
| 2015/0125539 A1 | 5/2015 | Popov |
| 2015/0265542 A1 | 9/2015 | Popov |
| 2015/0265543 A1 | 9/2015 | Popov |
| 2015/0297531 A1 | 10/2015 | Ensign |

FOREIGN PATENT DOCUMENTS

| | | | |
|---|---|---|---|
| EP | 0 692 510 B1 | 12/2004 | |
| EP | 1 744 759 B1 | 9/2009 | |
| EP | 2 127 655 A1 | 12/2009 | |
| EP | 2335686 | 6/2011 | |
| JP | 2011-140470 | 7/2011 | |
| WO | 95/03356 A1 | 2/1995 | |
| WO | 95/11669 A1 | 5/1995 | |
| WO | 95/22318 A1 | 8/1995 | |
| WO | 97/20578 A1 | 6/1997 | |
| WO | 97/44013 A1 | 11/1997 | |
| WO | 98/29097 A1 | 7/1998 | |
| WO | 98/31346 A1 | 7/1998 | |
| WO | 99/01498 A1 | 1/1999 | |
| WO | 00/46147 A2 | 8/2000 | |
| WO | 02/38127 A2 | 5/2002 | |
| WO | 02/053189 A2 | 7/2002 | |
| WO | 03/000237 A2 | 1/2003 | |
| WO | 2004060977 | 7/2004 | |
| WO | 2005/046671 A1 | 5/2005 | |
| WO | 2005055985 A1 | 6/2005 | |
| WO | 2005/072710 A2 | 8/2005 | |
| WO | 2005/094836 A2 | 10/2005 | |
| WO | 2006/044660 A2 | 4/2006 | |
| WO | 2006/063249 A2 | 6/2006 | |
| WO | 2006063249 | 6/2006 | |
| WO | 2006091780 A2 | 8/2006 | |
| WO | 2006094808 | 9/2006 | |
| WO | 2007084418 | 7/2007 | |
| WO | 2007/133808 A2 | 11/2007 | |
| WO | 2008/030557 A2 | 3/2008 | |
| WO | 2008/033924 A2 | 3/2008 | |
| WO | WO 2008030557 A2 * | 3/2008 | ............ A61K 9/0034 |
| WO | 2010040188 | 4/2008 | |
| WO | 2008/124632 A1 | 10/2008 | |
| WO | 2010132664 | 11/2010 | |
| WO | 2011080148 A2 | 7/2011 | |
| WO | 2011/106168 A1 | 9/2011 | |
| WO | 2011106702 | 9/2011 | |
| WO | WO 2011106702 A2 * | 9/2011 | ............ A61K 9/0051 |
| WO | 2011/157428 A2 | 12/2011 | |
| WO | 2011/159328 A1 | 12/2011 | |
| WO | 2012/013884 A1 | 2/2012 | |
| WO | 2012/014114 A1 | 2/2012 | |
| WO | 2012/038942 A1 | 3/2012 | |
| WO | 2012/038943 A1 | 3/2012 | |

(56) References Cited

FOREIGN PATENT DOCUMENTS

| WO | 2012/038944 A1 | 3/2012 |
|---|---|---|
| WO | 2012/039979 A2 | 3/2012 |
| WO | 2012054923 | 4/2012 |
| WO | 2012/059158 A1 | 5/2012 |
| WO | 2012/061703 A1 | 5/2012 |
| WO | 2012/071042 A1 | 5/2012 |
| WO | 2012/074980 A2 | 6/2012 |
| WO | 2012/088431 A1 | 6/2012 |
| WO | 2012/088469 A1 | 6/2012 |
| WO | 2012/093117 A1 | 7/2012 |
| WO | 2012/109363 A2 | 8/2012 |
| WO | 2012/127506 A1 | 9/2012 |
| WO | 2012/149228 A1 | 11/2012 |
| WO | 2012/155062 A1 | 11/2012 |
| WO | 2012/162698 A1 | 11/2012 |
| WO | 2013/040347 A1 | 3/2013 |
| WO | 2013/061269 A1 | 5/2013 |
| WO | 2013/065028 A1 | 5/2013 |
| WO | 2013/090804 A2 | 6/2013 |
| WO | 2013110028 | 7/2013 |
| WO | 2013138343 | 9/2013 |
| WO | 2013138346 | 9/2013 |
| WO | 2013166385 | 11/2013 |
| WO | 2013166408 | 11/2013 |
| WO | 2013166436 | 11/2013 |
| WO | 2013166498 | 11/2013 |
| WO | 2014047439 | 3/2014 |

OTHER PUBLICATIONS

Yang M. et al. "Production of virus-mimetic mucus-penetrating particles for drug and gene delivery in mucosal tissues." 2008 Annual Meeting of AIChE Nanoscale Science and Engineering Forum, Nov. 16-21, 2008, Abstract 705b.
Ludwig A "The use of mucoadhesive polymers in ocular drug delivery." Adv Drug Deliv Rev 57:1595-1639, 2005.
Miemon A. et al. "Optimization of formulation parameters on ocular loteprednol etabonate nanosuspension by media milling method." Int J Pharmaceut Biol Arch 4:46-51, 2012.
Sahib MN et al. "Solubilization of beclomethasone dipropionate in sterically stabilized phospholipid nanomicelles (SSMs): physicochemical and in vitro evaluations." Drug Des Devel Ther 6:29-42, 2012.
Lai et al., "Mucus-penetrating nanoparticles for drug and gene delivery to mucosal tissues", Adv. Drug Deliv. Rev., (Feb. 27, 2009), vol. 61, No. 2, 36 pages.
Lai et al., "Drug carrier nanoparticles that penetrate human chronic rhinosinusitis mucus", Biomaterials, (2011), vol. 32, pp. 6285-6290.
Lai et al., "Altering Mucus Rheology to "Solidify" Human Mucus at the Nanoscale", PLoS ONE, (Jan. 2009), vol. 4, Issue 1, pp. 1-6.
Lai et al., "Rapid transport of large polymeric nanoparticles in fresh undiluted human mucus", PNAS, (Jan. 30, 2007), vol. 104, No. 5, pp. 1482-1487.
Lai et al., "Nanoparticles reveal that human cervicovaginal mucus is riddled with pores larger than viruses", PNAS, (Jan. 12, 2010), vol. 107, No. 2, pp. 598-603.
Lipman et al., "Monoclonal Versus Polyclonal Antibodies: Distinguishing Characteristics, Applications, and Information Resources", ILAR Journal, (2005), vol. 46, No. 3, pp. 258-268.
Lo et al., "Formulation design and pharmaceutical development of a novel controlled release form of azithromycin for single-dose therapy", Drug Development and Industrial Pharmacy, (2009), vol. 35, No. 12, pp. 1522-1529.
Qiu et al., "Compatibility and degradation of new polyphosphazene/polyanhydride blend", CAPLUS, (2001), No. 5, Abstract Only.
Abelson et al., "Loteprednol Etabonate in the Management of Dry Eye Inflammation", Refractive eyecare for ophthalmologists, (Nov. 2000), vol. 4, No. 11, pp. 4-7.
Mert et al., "A poly(ethylene glycol)-based surfactant for formulation of drug-loaded mucus penetrating particles", Journal of Controlled Release, (2012), vol. 157, pp. 455-460.

Mu et al., "Vitamin E TPGS used as emulsifier in the solvent evaporation/extraction technique for fabrication of polymeric nanospheres for controlled release of paclitaxel (Taxol®)", Journal of Controlled Release, (2002), vol. 80, pp. 129-144.
Nance et al., "A Dense Poly(Ethylene Glycol) Coating Improves Penetration of Large Polymeric Nanoparticles Within Brain Tissue", Science Translational Medicine, (Aug. 29, 2012), vol. 4, Issue 149, pp. 1-8.
Newman et al., "Uptake of poly(D,L-lactic-co-glycolic acid) microspheres by antigen-presenting cells in vivo", Journal of Biomedical Materials Research, (Jun. 5, 2002), vol. 60, Issue 3, pp. 480-486.
Norris et al., "Effect of Size, Surface Charge, and Hydrophobicity on the Translocation of Polystyrene microspheres Through Gastrointestinal Mucin", Journal of Applied Polymer Science, (Mar. 14, 1997), vol. 63, Issue 11, pp. 1481-1492.
Norris et al., "The Uptake and Translocation of Microparticles through GI Mucin", Pharma. Res., (1995), vol. 12, pp. S233 abstract only.
Peppas et al., "Ultrapure poly(vinyl alcohol) hydrogels with mucoadhesive drug delivery characteristics", European Journal of Pharmaceutics and Biopharmaceutics, (1997), vol. 43, pp. 51-58.
Peppas et al., "Poly(ethylene glycol)-containing hydrogels in drug delivery", Journal of Controlled Release, (1999), vol. 62, pp. 81-87.
Peracchia et al., "PEG-coated nanospheres from amphiphilic diblock and multiblock copolymers: Investigation of their drug encapsulation and release characteristics", Journal of Controlled Release, (1997), vol. 46, pp. 223-231.
Perry, "Sorbent Materials and Sorption-Process Analysis", Perry's Chemical Engineers' Handbook, (1984), vol. 6, pp. 16-5-16-6.
Pillai et al., "Polymers in drug delivery", Current Opinion in Chemical Biology, (2001), vol. 5, pp. 447-451.
Prasad et al., "Confocal microscopy of colloids", Journal of Physics Condensed Matter, (2007), vol. 19, pp. 1-25.
Prego et al., "The potential of chitosan for the oral administration of peptides", Expert Opinion Drug Deliver, (2005), vol. 2, No. 5, pp. 843-854.
Pui, "Rasburicase: a potent uricolytic agent", Expert Opin. Pharmacother., (2002), vol. 3, No. 4, pp. 433-452.
Qiu et al., "Design of a core-shelled polymer cylinder for potential programmable drug delivery", International Journal of Pharmaceutics, (2001), vol. 219, pp. 151-160.
Rodeheaver et al., "Pluronic F-68: A Promising New Skin Wound Cleanser", Ann Emerg Med, (Nov. 1980), vol. 9, No. 11, pp. 572-576.
Rolland et al., "Direct Fabrication and Harvesting of Monodisperse, Shape-Specific Nanobiomaterials", J. Am. Chem. Soc., (2005), vol. 127, No. 28, pp. 10096-10100.
Schuster et al., "Nanoparticle diffusion in respiratory mucus from humans without lung disease", Biomaterials, (2013), vol. 34, pp. 3439-3446.
Serra et al., "Engineering Design and Molecular Dynamics of Mucoadhesive Drug Delivery Systems as Targeting Agents", Eur. J. Pharm. Biopharm., (Mar. 2009), vol. 71, No. 3, 24 pages.
Serra et al., "Design of poly(ethylene glycol)-tethered copolymers as novel mucoadhesive drug delivery systems", European Journal of Pharmaceutics and Biopharmaceutics, (2006), vol. 63, pp. 11-18.
Shakesheff et al., "The Adsorption of Poly(vinyl alcohol) to Biodegradable Microparticles Studied by X-Ray Photoelectron Spectroscopy (XPS)", Journal of Colloid and Interface Science, (1997), vol. 185, pp. 538-547.
Singh et al., "Cationic microparticles: A potent delivery system for DNA vaccines", PNAS, (Jan. 18, 2000), vol. 97, No. 2, pp. 811-816.
Singla et al., "Paclitaxel and its formulations", International Journal of Pharmaceutics, (2002), vol. 235, pp. 179-192.
Suh et al., "Real-time multiple-particle tracking: applications to drug and gene delivery", Advanced Drug Delivery Reviews, (2005), vol. 57, pp. 63-78.
Suh et al., "PEGylation of nanoparticles improves their cytoplasmic transport", International Journal of Nanomedicine, (2007), vol. 2, No. 4, pp. 735-741.

(56) References Cited

OTHER PUBLICATIONS

Suk et al., "The penetration of fresh undiluted sputum expectorated by cystic fibrosis patients by non-adhesive polymer nanoparticles", Biomaterials, (2009), vol. 30, pp. 2591-2597.
Suk et al., "N-acetylcysteine Enhances Cystic Fibrosis Sputum Penetration and Airway Gene Transfer by Highly Compacted DNA Nanoparticles", Molecular Therapy, (Nov. 2011), vol. 19, No. 11, pp. 1981-1989.
Suk et al., "Rabid transport of muco-inert nanoparticles in cystic fibrosis sputum treated with N-acetyl cysteine", Nanomedicine, (2011), vol. 6, No. 2, pp. 365-375.
Tang et al., "Biodegradable polymer nanoparticles that rapidly penetrate the human mucus barrier", PNAS, (Nov. 17, 2009), vol. 106, No. 46, pp. 19268-19273.
Vila et al., "Transport of PLA-PEG particles across the nasal mucosa: effect of particle size and PEG coating density", Journal of Controlled Release, (2004), vol. 98, pp. 231-244.
Whaley et al., "Novel Approaches to Vaginal Delivery and Safety of Microbicides: Biopharmaceuticals, Nanoparticles, and Vaccines", Antiviral Research, (2010), vol. 885, pp. S55-S66.
Wang et al., "Mucoadhesive Nanoparticles May Disrupt the Protective Human Mucus Barrier by Altering Its Microstructure", PLoS ONE, (Jun. 2011), vol. 6, Issue 6, pp. 1-7.
Wang et al., "Addressing the PEG Mucoadhesivity Paradox to Engineer Nanoparticles that "Slip" through the Human Mucus Barrier", Angew. Chem. Int. Ed., (2008), vol. 47, pp. 1-5.
Wu et al., "Novel Nanoparticles Formed via Self-Assembly of Poly(ethylene glycol-b-sebacic anhydride) and Their Degradation in Water", Macromolecules, (2000), vol. 33, pp. 9040-9043.
Xu et al., "Nanoparticle diffusion in, and microrheology of, the bovine vitreous ex vivo", Journal of Controlled Release, (2013), vol. 167, pp. 76-84.
Xu et al., "Scalable method to produce biodegradable nanoparticles that rapidly penetrate human mucus", Journal of Controlled Release, (2013), vol. 170, pp. 279-286.
Yang et al., "Biodegradable Nanoparticles Composed Entirely of Safe Materials that Rapible Penetrate Human Mucus", Angew. Chem. Int. Ed., (2011), vol. 50, pp. 2597-2600.
Yoncheva et al., "Bioadhesive properties of pegylated nanoparticles", Expert Opin. Drug Deily., (2005), vol. 2, No. 2, pp. 205-218.
Yoncheva et al., "Evaluation of bioadhesive potential and intestinal transport of pegylated poly(anhydride) nanoparticles", International Journal of Pharmaceutics, (2007), vol. 334, pp. 156-165.
Yoo et al., "Biodegradable Nanoparticles Containing Doxorubicin-PLGA Conjugate for Sustained Release", Pharmaceutical Research, (1999), vol. 16, No. 7, pp. 1114-1118.
Yu et al., "Biodegradable mucus-penetrating nanoparticles composed of diblock copolymers of polyethylene glycol and poly(lactic-co-glycolic acid)", Drug Deliv. and Trans!. Res., (2012), vol. 2, pp. 124-128.
Declaration of Dr. Alexey Popov executed Feb. 21, 2013 with Curriculum vitae.
Shuai et al., "Synthesis and characterization of several degradable aliphatic polyanhydrides", Journal of Beijing Institute of Technology (English Edition), (1996), vol. 5, No. 2, pp. 130-136 abstract only.
Webster's Ninth New Collegiate Dictionary, (1988), pp. 58.
International Search Report (Form PCT/ISA/210)dated Mar. 12, 2008, by the International Bureau of WIPO in corresponding International Patent Application No. PCT/US2007/019522. (5 pages).
Hancock et al., "What is the True Solubility Advantage for Amorphous Pharmaceuticals?", Pharmaceutical Research, (Nov. 4, 2000), vol. 17, No. 4, pp. 397-404.
"Lutrol® L and Lutrol F-Grades", Pharma Ingredients & Services, (Apr. 2010), 8 pages.
Kapin et al., "Inflammation-Mediated Retinal Edema in the Rabbit Is Inhibited by Topical Nepafenac", Inflammation, (Oct. 2003), vol. 27, No. 5, pp. 281-291.

Lin et al., "Carbopol.pluronic phase change solutions for ophthalmic drug delivery", Journal of Controlled Release, (2000), vol. 69, pp. 379-388.
Alexandridis, "Poly(ethylene oxide)/poly(propylene oxide) block copolymer surfactants", Current Opinion in Colloid & Interface Science, (Oct. 1997), vol. 2, Issue 5, pp. 478-489.
Yamagata et al., Improvement of the Oral Drug Absorption of Topotecan through the Inhibition of Intestinal Xenobiotic Efflux Transporter, Breast Cancer Resistance Protein, by Excipients, 35(7) Drug Metabolism and Disposition 1142-1148 (2007).
International Search Report dated Oct. 17, 2013, in PCT/US2013/039540.
International Search Report dated Aug. 26, 2013, in PCT/US2013/039499.
Albertsson et al, "Synthesis, Characterization and Degradation of Aliphatic Polyanhydrides", British Polymer Journal, (1990), vol. 23, No. 3, pp. 205-212.
Apgar et al., "Multiple-Particle Tracking Measurements of the Heterogeneities in Solutions of Actin Filaments and Actin Bundles", Biophysical Journal, (Aug. 2000), vol. 79, No. 2, pp. 1095-1106.
Batrakove et al., "Pluronic Block Copolymers: Evolution of Drug Delivery Concept from Inert Nanocarriers to Biological Response Modifiers", J. Control Release, (Sep. 10, 2008), vol. 130, No. 2, 25 pages.
Bhalla, "Microtubule-targeted anticancer agents and apoptosis", Oncogene, (2003), vol. 22, pp. 9075-9086.
Boskey et al., "A Self-Sampling Method to Obtain Large Volumes of Undiluted Cervicovaginal Secretions", Sexually Transmitted Diseases, (Feb. 2003), vol. 30, No. 2, pp. 107-109.
Boylan et al., "Enhancement of airway gene transfer by DNA nanoparticles using a pH-responsive block copolymer glycol and poly-L-lysine", Biomaterials, (2012) vol. 33, pp. 2361-2371.
Boylan et al., "Highly compacted DNA nanoparticles with low MW PEG coatings: In vitro, ex vivo and in vivo evaluation", Journal of Controlled Release, (2012), vol. 157, pp. 72-79.
Brorson et al., "Mutational Analysis of Avidity and Fine Specificity of Anti-Levan Antibodies", The Journal of Immunology, (1999), pp. 6694-6701.
Brummell et al., "Probing the Combining Site of an Anti-Carbohydrate Antibody by Saturation-Mutagenesis: Role of the Heavy-Chain CDR3 Residues", Biochemistry, (1993), vol. 32, No. 4, pp. 1180-1187.
Bures et al., "Surface modifications and molecular imprinting of polymers in medical and pharmaceutical applications", Journal of Controlled Release, (2001), vol. 72, pp. 25-33.
Burks et al., "In vitro scanning saturation mutagenesis of an antibody binding pocket", Proc. Natl. Acad. Sci. USA, (Jan. 1997), vol. 94, pp. 412-417.
Chan et al., "Phase behavior and miscibility in blends of poly(sebacic anhydride)/poly(ethylene glycol)", Biomaterials, (2002), vol. 23, pp. 2353-2358.
Bin Choy et al., "Mucoadhesive Microparticles Engineered for Ophthalmic Drug Delivery", J. Phys. Chem Solids, (May 2008), vol. 69, No. 5-6, 8 pages.
Colman, "Effects of amino acid sequence changes on antibody-antigen interactions", Research in Immunology, (1994), vol. 145, pp. 33-36.
Cone, "Barrier properties of mucus", Advanced Drug Delivery Reviews, (2009), vol. 61, pp. 75-85.
Cone, "Mucus", Mucosal Immunology, (1999), Section Edition, Chapter 4, pp. 43-64.
Cu et al., "Controlled surface modification with poly(ethylene)glycol enhances diffusion of PLGA nanoparticles in human cervical mucus", Mol Pharm., (2009), vol. 6, No. 1, 18 pages.
Dawson et al., "Transport of Polymeric Nanoparticle Gene Carriers in Gastric Mucus", Biotechnol. Prog., (2004), vol. 20, No. 3, pp. 851-857.
Dawson et al., "Enhanced Viscoelasticity of Human Cystic Fibrotic Sputum Correlates with Increasing Microheterogeneity in Particle Transport", The Journal of Biological Chemistry, (2003), vol. 278, No. 50, pp. 50393-50401.

(56) References Cited

OTHER PUBLICATIONS

Dawson et al., "Primary parenteral transmission of bovine spongiform encephalopathy to the pig", The Veterinary Record, (Sep. 29, 1990), 1 page.
De Campos et al., "The effect of a PEG versus a chitosan coating on the interaction of drug colloidal carriers with the ocular mucosa", European Journal of Pharmaceutical Sciences, (2003), vol. 20, pp. 73-81.
Delgado et al., "Radiolabelled biodegradable microspheres for lung imaging", European Journal of Pharmaceutics and Biopharmaceutics, (2000), vol. 50, pp. 227-236.
Denis-Mize et al., "Plasmid DNA adsorbed onto cationic microparticles mediates target gene expression and antigen presentation by dendritic cells", Gene Therapy, (2000), vol. 7, pp. 2105-2112.
Donaldson et al., "A placebo-controlled multi-centred evaluation of an anaesthetic gel (Oraqix®) for periodontal therapy", Journal of Clinical Peridontology, (2003), vol. 30, pp. 171-175.
Dufner et al., "Harnessing phage and ribosome display for antibody optimisation", TRENDS in Biotechnology, (2006), vol. 24, No. 11, pp. 523-529.
Dumortier et al., "A Review of Poloxamer 407 Pharmaceutical and Pharmacological Characteristics", Pharmaceutical Research, (Dec. 2006), vol. 23, No. 12, pp. 2709-2728.
Ehrhardt et al., "Drug Absorption by the Respiratory Mucosa: Cell Culture Models and Particulate Drug Carriers", Journal of Aerosol Medicine, (2002), vol. 15, No. 2, pp. 131-139.
Emanuele, "FLOCOR™: a new anti-adhesive, rheologic agent", Expert Opinion on Investigational Drugs, (1998), vol. 7, No. 7, pp. 1193-1200.
Ensign et al., "Oral drug delivery with polymeric nanoparticles: The gastrointestinal mucus barriers", Advanced Drug Delivery Reviews, (2012), vol. 64, pp. 557-570.
Ensign et al., "Mucus Penetrating Nanoparticles: Biophysical Tool and Method of Drug and Gene Delivery", Advanced Materials, (2012), vol. 24, pp. 3887-3894.
Ensign et al., "Enhanced vaginal drug delivery through the use of hypotonic formulations that induce fluid uptake", Biomaterials, (2013), vol. 34, pp. 6922-6929.
Ensign et al., "Ex Vivo Characterization of Particle Transport in Mucus Secretions Coating Freshly Excised Mucosal Tissues", Molecular Pharmaceutics, (2013), vol. 10, pp. 2176-2182.
Ensign et al., "Mucus-Penetrating Nanoparticles for Vaginal Drug Deliver Protect Against Herpes Simplex Virus", Science Translational Medicine, (2012), vol. 4, Issue 138, pp. 1-10.
Escobar-Chávez et al., "Application of Thermo-Reversible Pluronic F-127 Gels in Pharmaceutical Formulations", J. Pharm. Pharmaceut. Sci., (2006), vol. 9, No. 3, pp. 339-358.
Farokhzad et al., "Targeted nanoparticle-aptamer bioconjugates for cancer chemotherapy in vivo", PNAS, (Apr. 18, 2006), vol. 103, No. 16, pp. 6315-6320.
Fresta et al., "Ocular Tolerability and In Vivo Bioavailability of Poly(ethylene glycol) (PEG)-Coated Polyethyl-2-Cyanoacrylate Nanosphere-Encapsulated Acyclovir", Journal of Pharmaceutical Science, (Mar. 2001), vol. 90, No. 3, pp. 288-297.
Fu et al., "New polymeric carriers for controlled drug delivery following inhalation or injection", Biomaterials, (2002), vol. 23, pp. 4425-4433.
Giannavola et al., "Influence of Preparation Conditions on Acyclovir-Loaded Poly-d,I-Lactic Acid Nanospheres and Effect of PEG Coating on Ocular Drug Bioavailability", Pharmaceutical Research, (Apr. 2003), vol. 20, No. 4, pp. 584-590.
Giunchedi et al., "Emulsion Spray-Drying for the Preparation of Albumin-Loaded PLGA Microspheres", Drug Development and Industrial Pharmacy, (2001), vol. 27, No. 7, pp. 745-750.
Hida et al., "Common Gene Therapy Viral Vectors Do Not Efficiently Penetrate Sputum from Cystic Fibrosis Patients", PLoS ONE, (May 2011), vol. 6, Issue 5, pp. 1-6.
Huang et al., "Molecular aspects of muco- and bioadhesion: Tethered structures and site-specific surfaces", Journal of Controlled Release, (2000), vol. 65, pp. 63-71.
Jachak et al., "Transport of metal oxide nanoparticles and single walled carbon nanotubes in human mucus", Nanotoxicology, (Sep. 2012), vol. 6, No. 6, pp. 614-622.
Jang et al., "The structural basis for DNA binding by an anti-DNA autoantibody", Molecular Immunology, (1998), vol. 35, pp. 1207-1217.
Jiang et al., "Pulsatile protein release from a laminated device comprising of polyanhydrides and pH-sensitive complexes", International Journal of Pharmaceutics, (2000), vol. 194, pp. 51-60.
Jiang et al., Preparation, characterization and degradation characteristics of polyanhydrides contained poly(ethylene glycol), Polymer International, (1999), vol. 48, pp. 47-52.
Kim et al., "Use of Single-Site-Functionalized PEG Dendrons to Prepare Gene Vectors that Penetrate Human Mucus Barriers", Angewandte Chemie International Edition, (2013), vol. 52, pp. 3985-3988.
Kim et al., "Comparison of the pharmacokinetic profiles of two locally administered doxycycline gels in crevicular fluid and saliva", Journal of Clinical Periodontology, (2004), vol. 31, pp. 286-292.
Knowles et al., "Mucus clearance as primary innate defense mechanism for mammalian airways", The Journal of Clinical Investigation, (Mar. 2002), vol. 109, No. 5, pp. 571-577.
Kobayashi et al., "Tryptophan H33 plays an important role in pyrimidine (6-4) pyrimidone photoproduct binding by a high-affinity antibody", Protein Engineering, (1999), vol. 12, No. 10, pp. 879-884.
Lai et al., "Micro- and macrorheology of mucus", Advanced Drug Delivery Reviews, (2009), vol. 61, pp. 86-100.
Wang et al. "Preparation, characterization of paclitaxel-loaded Pluronic P105 polymeric micelles and in vitro reversal of multidrug resistant tumor." Acta Pharmaceutica Sincia 43:640-646, 2008.

* cited by examiner

FIG. 8A
FIG. 8B
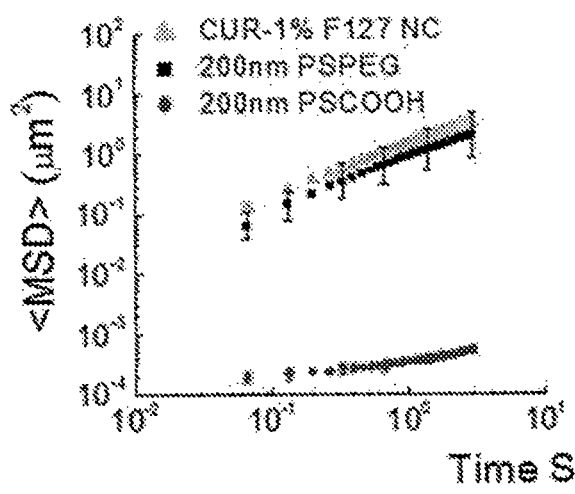
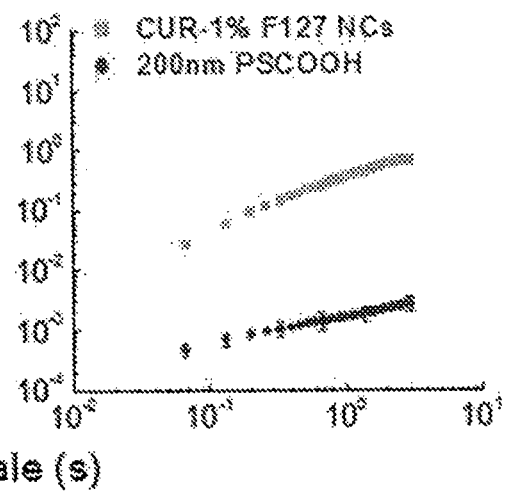

FIG. 13A
FIG. 13B
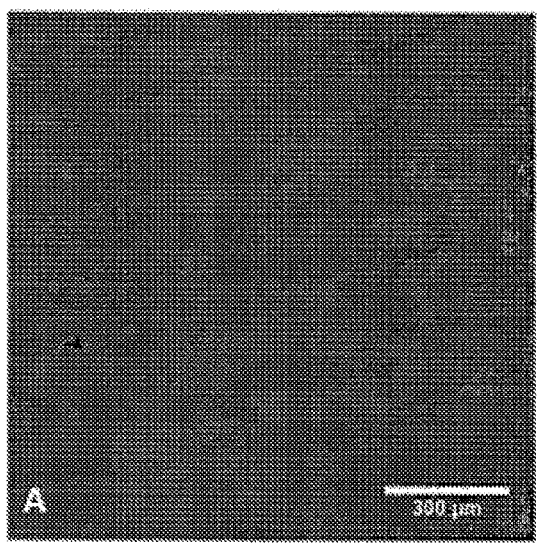
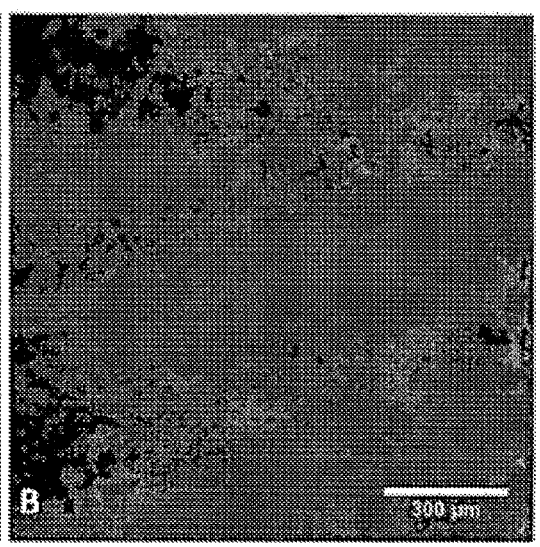

FIG. 14A
FIG. 14B
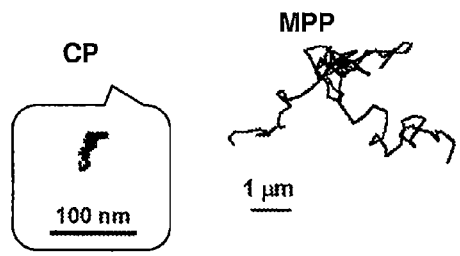
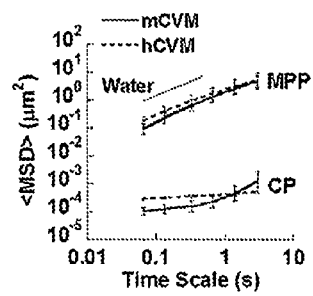
FIG. 14C
FIG. 14D
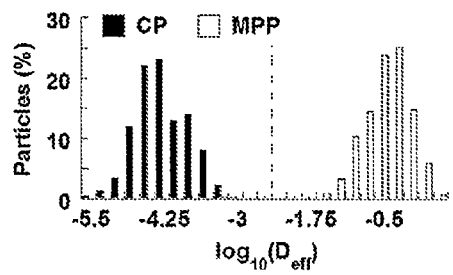
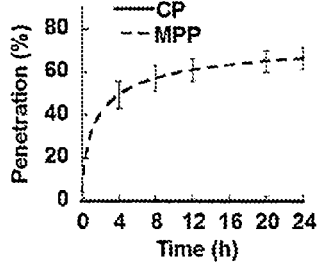
FIG. 14E
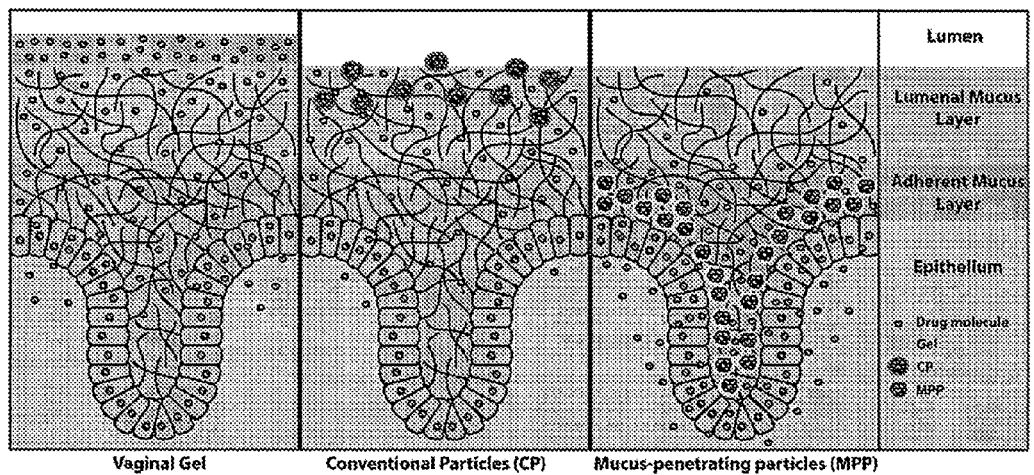

FIG. 21A
FIG. 21B
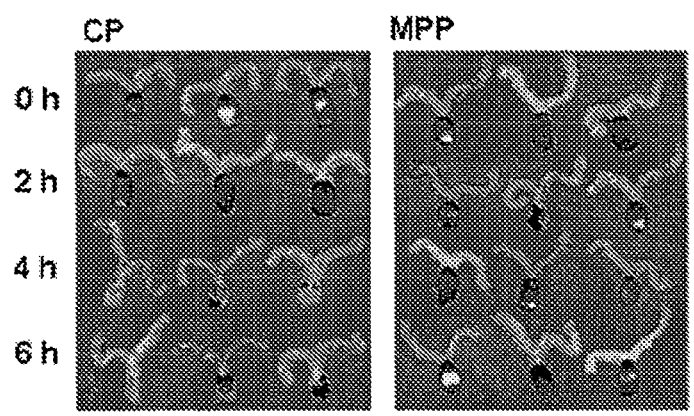
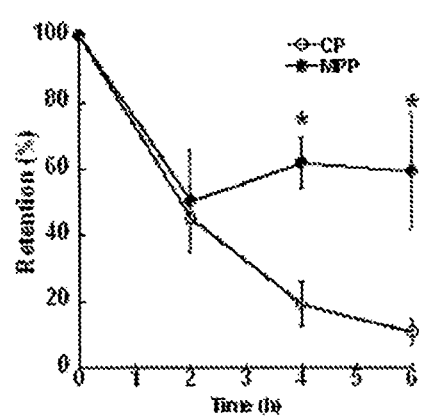

NANOCRYSTALS, COMPOSITIONS, AND METHODS THAT AID PARTICLE TRANSPORT IN MUCUS

RELATED APPLICATIONS

The present application is a continuation of U.S. patent application Ser. 15/187,552 filed Jun. 20, 3016, which is a continuation of U.S. patent application Ser. 14/731,921 filed Jun. 5, 2015, which is a continuation of Ser. No. 13/886,493, filed May 3, 2013, now U.S. Pat. No. 9,056,057, which claims priority under 35 U.S.C. §119(e) to U.S. Provisional Patent Application No. 61/642,227, filed May 3, 2012 and entitled "Nanocrystals, Compositions, and Methods That Aid Particle Transport in Mucus", which is incorporated herein by reference.

STATEMENT REGARDING FEDERALLY SPONSORED RESEARCH

This invention was made with government support under Grant Nos. R33AI079740, R33AI094519, R01HD062844, and R01CA140746 awarded by the National Institutes of Heath. The government has certain rights in the invention.

FIELD OF THE INVENTION

The present invention generally relates to nanocrystals, compositions, and methods that aid particle transport in mucus.

BACKGROUND OF THE INVENTION

A mucus layer present at various points of entry into the body, including the eyes, nose, lungs, gastrointestinal tract, and female reproductive tract, is naturally adhesive and serves to protect the body against pathogens, allergens, and debris by effectively trapping and quickly removing them via mucus turnover. For effective delivery of therapeutic, diagnostic, or imaging particles via mucus membranes, the particles must be able to readily penetrate the mucus layer to avoid mucus adhesion and rapid mucus clearance. Several lines of evidence suggest that conventional nanoparticles are not capable of crossing mucosal barriers. However, it has been recently demonstrated that polymeric nanoparticles (degradable or not) modified with a special surface coating (covalently or non-covalently) can diffuse in physiologically thick mucus samples nearly as rapidly as they would in water. Such polymer-based mucus-penetrating particles (MPP) can encapsulate various therapeutic, imaging, or diagnostic agents to enable drug delivery, diagnostic, or imaging applications.

Nevertheless, polymer-based MPP may have several inherent limitations compared to unencapsulated particles of pharmaceutical agents. In particular, in light of drug delivery applications these limitations may include: 1) Inherently lower drug loading; 2) Less convenient dosage form, as reconstitution from a dry powder storage form may be required for polymeric nanoparticles; 3) Potentially increased toxicity; 4) Chemical and physical stability concerns; and 5) Increased manufacturing complexity. Accordingly, improvements in compositions and methods involving mucus-penetrating particles for delivery of pharmaceutical agents would be beneficial.

SUMMARY OF THE INVENTION

The present description generally relates to nanocrystals, compositions, and methods that aid particle transport in mucus. In some embodiments, the compositions and methods involve mucus-penetrating particles without any polymeric carriers, or with minimal use of polymeric carriers. The subject matter of this application involves, in some cases, interrelated products, alternative solutions to a particular problem, and/or a plurality of different uses of structures and compositions.

In one set of embodiments, a method of forming coated particles is provided. The method involves combining core particles with a solution comprising a surface-altering agent, wherein the core particles comprise a solid pharmaceutical agent or a salt thereof, wherein the agent or salt has a solubility of less than or equal to about 1 mg/mL in the solution at 25° C., and wherein the pharmaceutical agent or salt thereof constitutes at least about 80 wt % of each of the core particles. The method also involves coating the core particles with the surface-altering agent to form coated particles, wherein the surface-altering agent comprises a triblock copolymer comprising a hydrophilic block-hydrophobic block-hydrophilic block configuration, wherein the hydrophobic block has a molecular weight of at least about 2 kDa, and the hydrophilic blocks constitute at least about 15 wt % of the triblock copolymer, wherein the hydrophobic block associates with the surface of the core particles, wherein the hydrophilic block is present at the surface of the coated particles and renders the coated particles hydrophilic, and wherein the coated particles have a relative velocity of greater than 0.5 in mucus.

In another set of embodiments, a composition comprising a plurality of coated particles is provided. The coated particle comprises a core particle comprising a solid pharmaceutical agent or a salt thereof, wherein the agent or salt has an aqueous solubility of less than or equal to about 1 mg/mL at 25° C. at any point throughout the pH range, wherein the pharmaceutical agent or salt thereof constitutes at least about 80 wt % of the core particle. The coated particle also includes a coating comprising a surface-altering agent surrounding the core particle, wherein the surface-altering agent comprises a triblock copolymer comprising a hydrophilic block-hydrophobic block-hydrophilic block configuration, wherein the hydrophobic block has a molecular weight of at least about 2 kDa, and the hydrophilic blocks constitute at least about 15 wt % of the triblock copolymer, wherein the hydrophobic block associates with the surface of the core particle, wherein the hydrophilic block is present at the surface of the coated particle and renders the coated particle hydrophilic, and wherein the surface-altering agent is present on the surface of the core particle at a density of at least about 0.001 molecules per nanometer squared. The coated particles have a relative velocity of greater than 0.5 in mucus.

In another set of embodiments, a method of forming coated comprises providing a pharmaceutical agent and precipitating the pharmaceutical agent by forming a salt in an aqueous solution in the presence of a surface-altering agent to form core particles of the pharmaceutical agent, wherein the salt has a lower aqueous solubility than the pharmaceutical agent in the non-salt form, the aqueous solubility of the salt being less than about 1 mg/mL at 25° C. at any point throughout the pH range, and wherein the surface-altering agent is present at a concentration of at least about 0.01% (w/v) in the aqueous solution. The method involves coating the core particles with the surface-altering agent to form coated particles, wherein the surface-altering agent comprises a triblock copolymer comprising a hydrophilic block-hydrophobic block-hydrophilic block configuration, wherein the hydrophobic block has a molecular weight of at least about 2 kDa, and the hydrophilic blocks constitute at least about 15 wt % of the triblock copolymer, wherein the hydrophobic block associates with the surfaces of the core particles, and wherein the hydrophilic block is present at the surfaces of the coated particles and renders the coated particles hydrophilic. The coated particles have a relative velocity of greater than 0.5 in mucus.

In another set of embodiments, a method of treatment is provided. The method comprises administering to a patient or a subject in need thereof, a composition comprising a plurality of coated particles. The coated particle comprises a core particle comprising a solid pharmaceutical agent or a salt thereof, wherein the agent or salt has an aqueous solubility of less than or equal to about 1 mg/mL at 25° C. at any point throughout the pH range, wherein the pharmaceutical agent or salt thereof constitutes at least about 80 wt % of the core particle. The coated particle also includes a coating comprising a surface-altering agent surrounding the core particle, wherein the surface-altering agent comprises a triblock copolymer comprising a hydrophilic block-hydrophobic block-hydrophilic block configuration, wherein the hydrophobic block has a molecular weight of at least about 2 kDa, and the hydrophilic blocks constitute at least about 15 wt % of the triblock copolymer, wherein the hydrophobic block associates with the surface of the core particle, wherein the hydrophilic block is present at the surface of the coated particle and renders the coated particle hydrophilic, and wherein the surface-altering agent is present on the surface of the core particle at a density of at least about 0.001 molecules per nanometer squared. The coated particles have a relative velocity of greater than 0.5 in mucus.

In another set of embodiments, a method is provided. The method comprises delivering to a mucus membrane a composition comprising a plurality of coated particles. The coated particle comprises a core particle comprising a solid pharmaceutical agent or a salt thereof, wherein the agent or salt has an aqueous solubility of less than or equal to about 1 mg/mL at 25° C. at any point throughout the pH range. The pharmaceutical agent or salt thereof constitutes at least about 80 wt % of the core particle. The coated particle also includes a coating comprising a surface-altering agent surrounding the core particle, wherein the surface-altering agent comprises a triblock copolymer comprising a hydrophilic block-hydrophobic block-hydrophilic block configuration, wherein the hydrophobic block has a molecular weight of at least about 2 kDa, and the hydrophilic blocks constitute at least about 15 wt % of the triblock copolymer. The hydrophobic block associates with the surface of the core particle, and the hydrophilic block is present at the surface of the coated particle and renders the coated particle hydrophilic. The surface-altering agent is present on the surface of the core particle at a density of at least about 0.001 molecules per nanometer squared. The coated particles have a relative velocity of greater than 0.5 in mucus.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 7A is a powder X-ray diffraction (Powder-XRD) diagram of F127, raw curcumin and CUR-1% F127 particles. FIG. 7B is a representative transmission electron microscope (TEM) image of CUR-1% F127 particles.

FIGS. 8A and 8B are ensemble averaged geometric mean-squared displacements (<MSD>) of CUR-1% F127 particles, 200 nm carboxylated polystyrene (PSCOOH) and 200 nm PEGylated polystyrene (PSPEG) particles in CVM (FIG. 8A) and human cystic fibrosis sputum (CFS) (FIG. 8B) as a function of time scale according to one set of embodiments. Data represent the ensemble average of five independent experiments, with n≥100 for each experiment. Error bars indicate geometric standard error.

FIG. 10A shows distribution of <Deff> at a time scale of 1 s with regards to the molecular weight (MW) of poly(ethylene glycol) (PEG) segment and poly(propylene oxide) (PPO) segment of Pluronics®. Each data point represents a specific type of Pluronics®. PPO and PEG MW were estimated based on the molecular weight provided by the manufacturer. FIGS. 10B-C show <Deff> at a time scale of 1 s as a function of the MW of (B) PEG or (C) PPO segments. Inset represents the same plot with linear scale of <Deff>, while R represents the correlation coefficient. Data represent the ensemble average of at least three independent experiments, with n≥100 for each experiment. Error bars indicate geometric standard error.

FIGS. 13A-13B are images showing distribution of mucus penetrating/F127-coated TFV particles (FIG. 13A) and muco-adhesive/PVA-coated TFV particles (FIG. 13B) on flattened vaginal tissue from human-like estrus phase mice according to one set of embodiments. Vaginal tissues were removed within 10 minutes of administration.

FIGS. 14A-14D show the transport rates of CP and MPP in mouse estrus phase CVM. (FIG. 14A) Representative trajectories for particles exhibiting effective diffusivities within one SEM of the ensemble average at a time scale of 1 s. (FIG. 14B) Ensemble-averaged geometric mean square displacements (<MSD>) as a function of time scale. Data for particles on ex vivo mouse vaginal tissue (mCVM) compared to the same particles in ex vivo human CVM (hCVM) (S. K. Lai, Y. Y. Wang, K. Hida, R. Cone, J. Hanes, Nanoparticles reveal that human cervicovaginal mucus is riddled with pores larger than viruses. P Natl Acad Sci USA 107, 598-603 (2010)) and the theoretical diffusion rate of 110 nm particles in water (~4 μm$^2$/s). (FIG. 14C) Distributions of the logarithms of individual particle effective diffusivities ($D_{eff}$) at a time scale of 1 s. Data represent the ensemble average of three independent experiments, with n≥150 particles for each experiment. Diffusivity values to the left of the dotted line indicate particles with MSD values less than the particle diameter. (FIG. 14D) Percentage of particles capable of penetrating a 100 μm-thick layer of mouse CVM over time, based on Fick's Second Law of diffusion simulation of particles undergoing random diffusion, with diffusivities equal to the experimentally measured diffusivities of the particles. FIG. 14E is a graphical depiction of vaginal drug delivery from gel, CP, and MPP formulations.

(FIG. 15A) Data are shown for MPP and CP on ex vivo vaginal tissue of induced estrus (IE) and naturally cycling estrus phase mice. (FIG. 15B) Biodegradable MPPs on IE tissue were compared to non-degradable MPPs. Data represent the ensemble average of at least 3 independent experiments, with an average n≥150 particles and at least 130 particles for each experiment. Data are presented as a mean with the standard error of the mean (SEM).

FIGS. 21A-21B are images and a plot showing the retention of non-biodegradable MPPs and CPs in the IE mouse cervicovaginal tract. (FIG. 21A) Overlay of particle fluorescence intensity and bright-field images for CPs and MPPs in whole cervicovaginal tract tissue. (FIG. 21B) Fraction of particles remaining over time based on quantification of particle fluorescence. Data are means±SEM (n≥7). *P<0.05, Student's t test.

DETAILED DESCRIPTION

Figure 1:
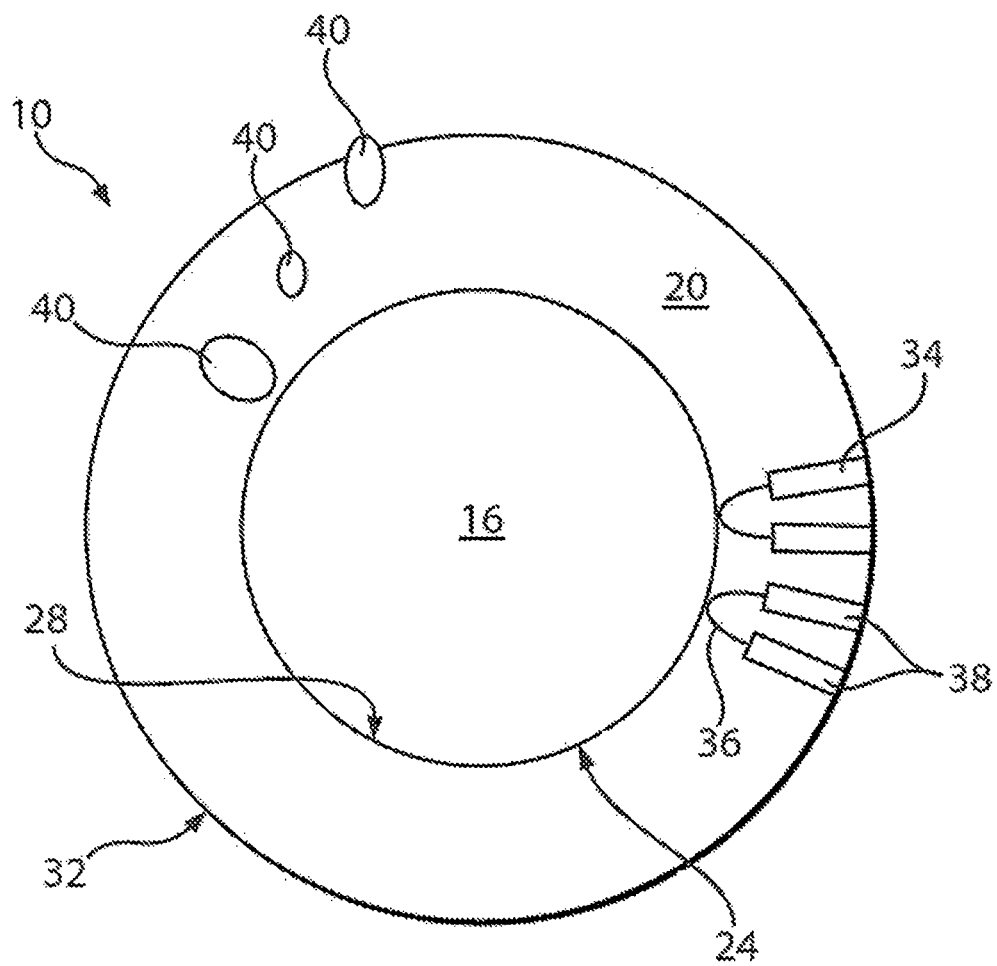
FIG. 1 is a schematic drawing of a mucus-penetrating particle having a coating and a core of a solid pharmaceutical agent according to one set of embodiments.

Nanocrystals, compositions, and methods that aid particle transport in mucus are provided. In some embodiments, the compositions and methods involve making mucus-penetrating particles (MPP) without any polymeric carriers, or with minimal use of polymeric carriers. The compositions and methods may include, in some embodiments, modifying the surface coatings of particles formed of pharmaceutical agents that have a low water/aqueous solubility. Such methods and compositions can be used to achieve efficient transport of particles of pharmaceutical agents though mucus barriers in the body for a wide spectrum of applications, including drug delivery, imaging, and diagnostic applications. In certain embodiments, a pharmaceutical composition including such particles is well-suited for administration routes involving the particles passing through a mucosal barrier.

In some embodiments, the particles described herein have a core-shell type arrangement. The core may comprise a solid pharmaceutical agent or a salt thereof having a relatively low aqueous solubility. The core may be coated with a coating or shell comprising a surface-altering agent that facilitates mobility of the particle in mucus. As described in more detail below, in some embodiments the surface-altering agent may comprise a triblock copolymer comprising a hydrophilic block-hydrophobic block-hydrophilic block configuration. The molecular weights of each of the hydrophilic and hydrophobic blocks may be chosen to impart certain transport characteristics to the particles, such as increased transport through mucus.

Non-limiting examples of particles are now provided. As shown in the illustrative embodiment of FIG. 1, a particle 10 includes a core 16 (which may be in the form of a particle, referred to herein as a core particle) and a coating 20 surrounding the core. In one set of embodiments, a substantial portion of the core is formed of one or more solid pharmaceutical agents (e.g., a drug, therapeutic agent, diagnostic agent, imaging agent) that can lead to certain beneficial and/or therapeutic effects. The core may be, for example, a nanocrystal (i.e., a nanocrystal particle) of a pharmaceutical agent. The core includes a surface 24 to which one or more surface-altering agents can be attached. For instance, in some cases, core 16 is surrounded by coating 20, which includes an inner surface 28 and an outer surface 32. The coating may be formed, at least in part, of one or more surface-altering agents 34, such as a polymer (e.g., a block copolymer), which may associate with surface 24 of the core. Surface-altering agent 34 may be associated with the core particle by, for example, being covalently attached to the core particle, non-covalently attached to the core particle, adsorbed to the core, or attached to the core through ionic interactions, hydrophobic and/or hydrophilic interactions, electrostatic interactions, van der Waals interactions, or combinations thereof. In one set of embodiments, the surface-altering agents, or portions thereof, are chosen to facilitate transport of the particle through a mucosal barrier (e.g., mucus or a mucosal membrane).

In certain embodiments described herein, one or more surface-altering agents 34 are oriented in a particular configuration in the coating of the particle. For example, in some embodiments in which a surface-altering agent is a triblock copolymer, such as a triblock copolymer having a hydrophilic block-hydrophobic block-hydrophilic block configuration, a hydrophobic block 36 may be oriented towards the surface of the core, and hydrophilic blocks 38 may be oriented away from the core surface (e.g., towards the exterior of the particle). The hydrophilic blocks may have characteristics that facilitate transport of the particle through a mucosal barrier, as described in more detail below.

Particle 10 may optionally include one or more components 40 such as targeting moieties, proteins, nucleic acids, and bioactive agents which may optionally impart specificity to the particle. For example, a targeting agent or molecule (e.g., a protein, nucleic acid, nucleic acid analog, carbohydrate, or small molecule), if present, may aid in directing the particle to a specific location in the subject's body. The location may be, for example, a tissue, a particular cell type, or a subcellular compartment. One or more components 40, if present, may be associated with the core, the coating, or both; e.g., they may be associated with surface 24 of the core, inner surface 28 of the coating, outer surface 32 of the coating, and/or embedded in the coating. The one or more components 40 may be associated through covalent bonds, absorption, or attached through ionic interactions, hydrophobic and/or hydrophilic interactions, electrostatic interactions, van der Waals interactions, or combinations thereof. In some embodiments, a component may be attached (e.g., covalently) to one or more of the surface-altering agents of the coated particle using methods known to those of ordinary skill in the art.

It should be understood that components and configurations other than those shown in FIG. 1 or described herein may be suitable for certain particles and compositions, and that not all of the components shown in FIG. 1 are necessarily present in some embodiments.

In one set of embodiments, particle 10, when introduced into a subject, may interact with one or more components in the subject such as mucus, cells, tissues, organs, particles, fluids (e.g., blood), portions thereof, and combinations thereof. In some such embodiments, the coating of particle 10 can be designed to include surface-altering agents or other components with properties that allow favorable interactions (e.g., transport, binding, adsorption) with one or more materials from the subject. For example, the coating may include surface-altering agents or other components having a certain hydrophilicity, hydrophobicity, surface charge, functional group, specificity for binding, and/or density to facilitate or reduce particular interactions in the subject. One specific example includes choosing a certain hydrophilicity, hydrophobicity, surface charge, functional group, specificity for binding, and/or density of one or more surface-altering agents to reduce the physical and/or chemical interactions between the particle and mucus of the subject, so as to enhance the mobility of the particle through mucus. Other examples are described in more detail below.

In some embodiments, once a particle is successfully transported across a mucosal barrier (e.g., mucus or a mucosal membrane) in a subject, further interactions between the particle in the subject may take place. Interactions may take place, in some instances, through the coating and/or the core, and may involve, for example, the exchange of materials (e.g., pharmaceutical agents, therapeutic agents, proteins, peptides, polypeptides, nucleic acids, nutrients, e.g.) from the one or more components of the subject to particle 10, and/or from particle 10 to the one or more components of the subject. For example, in some embodiments in which the core is formed of or comprises a pharmaceutical agent, the breakdown, release and/or transport of the pharmaceutical agent from the particle can lead to certain beneficial and/or therapeutic effects in the subject. As such, the particles described herein can be used for the diagnosis, prevention, treatment or management of certain diseases or bodily conditions.

Specific examples for the use of the particles described herein are provided below in the context of being suitable for administration to a mucosal barrier (e.g., mucus or a mucosal membrane) in a subject. It should be appreciated that while many of the embodiments herein are described in this context, and in the context of providing a benefit for diseases and conditions that involve transport of materials across a mucosal barrier, the invention is not limited as such and the particles, compositions, kits, and methods described herein may be used to prevent, treat, or manage other diseases or bodily conditions.

Mucus is a sticky viscoelastic gel that protects against pathogens, toxins, and debris at various points of entry into the body, including the eyes, nose, lungs, gastrointestinal tract, and female reproductive tract. Many synthetic nanoparticles are strongly mucoadhesive and become effectively trapped in the rapidly-cleared peripheral mucus layer, vastly limiting their distribution throughout the mucosal membrane as well as penetration toward the underlying tissue. The residence time of these trapped particles is limited by the turnover rate of the peripheral mucus layer, which, depending on the organ, ranges from seconds to several hours. To ensure effective delivery of particles including pharmaceutical agents (e.g., therapeutic, diagnostic, and/or imaging agents) via mucus membranes, such particles must be able to readily diffuse through the mucus barrier, avoiding mucus adhesion.

It has been recently demonstrated that modifying surfaces of polymeric nanoparticles with a mucus-penetrating coating can minimize adhesion to mucus and thus allow rapid particle penetration across mucus barriers. Specifically, it has been shown that polymeric nanoparticles as large as 500 nm, when coated covalently with dense coatings of low molecular weight PEG (2 kDa-5 kDa) or non-covalently with specific Pluronic® molecules (e.g., P103, P105, F127) can penetrate human mucus nearly as fast as they move in pure water, and at rates almost 100-fold faster than similarly-sized uncoated polymeric particles.

Nevertheless, polymer-based mucus-penetrating particles may have one or more inherent limitations in some embodiments. In particular, in light of drug delivery applications, these limitations may include one or more of the following: A) Low drug encapsulation efficiency and low drug loading: Encapsulation of drugs into polymeric particles is often inefficient, as generally less than 10% of the total amount of drug used gets encapsulated into particles during manufacturing. Additionally, drug loadings above 50% are rarely achieved. B) Convenience of usage: Formulations based on drug-loaded polymeric particles, in general, typically need to be stored as dry powder to avoid premature drug release and, thus, require either point-of-use re-constitution or a sophisticated dosing device. C) Biocompatibility: Accumulation of slowly degrading polymer carriers following repeated dosing and their toxicity over the long term present a major concern for polymeric drug carriers. D) Chemical and physical stability: Polymer degradation may compromise stability of encapsulated drugs. In many encapsulation processes, the drug undergoes a transition from a solution phase to a solid phase, which is not well-controlled in terms of physical form of the emerging solid phase (i.e., amorphous vs. crystalline vs. crystalline polymorphs). This is a concern for multiple aspects of formulation performance, including physical and chemical stability and release kinetics. E) Manufacturing complexity: Manufacturing, especially scalability, of drug-loaded polymeric MPP is a fairly complex process that typically involves multiple steps and a considerable amount of toxic organic solvents.

In some embodiments described herein, the compositions and methods of making particles, including certain compositions and methods for making particles that have increased transport through mucosal barriers, address one or more, or all, of the concerns described above. Specifically, in some embodiments, the compositions and methods do not involve encapsulation into polymeric carriers or involve minimal use of polymeric carriers. Advantageously, by avoiding or minimizing the need to encapsulate pharmaceutical agents (e.g., drugs, imaging or diagnostic agents) into polymeric carriers, certain limitations of polymeric MPP with respect to drug loading, convenience of usage, biocompatibility, stability, and/or complexity of manufacturing, may be addressed. The methods and compositions described herein may facilitate clinical development of the mucus-penetrating particle technology.

Core Particles

As described above in reference to FIG. 1, particle 10 may include a core 16. The core may be formed of any suitable material, such as an organic material, an inorganic material, a polymer, or combinations thereof. In one set of embodiments, the core comprises a solid. The solid may be, for example, a crystalline or an amorphous solid, such as a crystalline or amorphous solid pharmaceutical agent (e.g., a therapeutic agent, diagnostic agent, and/or imaging agent), or a salt thereof. In some embodiments, more than one pharmaceutical agents may be present in the core. Specific examples of pharmaceutical agents are provided in more detail below.

The pharmaceutical agent may be present in the core in any suitable amount, e.g., at least about 1 wt %, at least about 5 wt %, at least about 10 wt %, at least about 20 wt %, at least about 30 wt %, at least about 40 wt %, at least about 50 wt %, at least about 60 wt %, at least about 70 wt %, at least about 80 wt %, at least about 85 wt %, at least about 90 wt %, at least about 95 wt %, or at least about 99 wt % of the core. In one embodiment, the core is formed of 100 wt % of the pharmaceutical agent. In some cases, the pharmaceutical agent may be present in the core at less than about 100 wt %, less than about 90 wt %, less than about 80 wt %, less than about 70 wt %, less than about 60 wt %, less than about 50 wt %, less than about 40 wt %, less than about 30 wt %, less than about 20 wt %, less than about 10 wt %, less than about 5 wt %, less than about 2 wt %, or less than about 1 wt %. Combinations of the above-referenced ranges are also possible (e.g., present in an amount of at least about 80 wt % and less than about 100 wt %). Other ranges are also possible.

In embodiments in which the core particles comprise relatively high amounts of a pharmaceutical agent (e.g., at least about 50 wt % of the core particle), the core particles generally have an increased loading of the pharmaceutical agent compared to particles that are formed by encapsulating agents into polymeric carriers. This is an advantage for drug delivery applications, since higher drug loadings mean that fewer numbers of particles may be needed to achieve a desired effect compared to the use of particles containing polymeric carriers.

In some embodiments, the core is formed of a solid material having a relatively low aqueous solubility (i.e., a solubility in water, optionally with one or more buffers), and/or a relatively low solubility in the solution in which the solid material is being coated with a surface-altering agent. For example, the solid material may have an aqueous solubility (or a solubility in a coating solution) of less than about or equal to about 5 mg/mL, less than or equal to about 2 mg/mL, less than or equal to about 1 mg/mL, less than or equal to about 0.5 mg/mL, less than or equal to about 0.1 mg/mL, less than or equal to about 0.05 mg/mL, less than or equal to about 0.01 mg/mL, less than or equal to about 1 µg/mL, less than or equal to about 0.1 µg/mL, less than or equal to about 0.01 µg/mL, less than or equal to about 1 ng/mL, less than or equal to about 0.1 ng/mL, or less than or equal to about 0.01 ng/mL at 25° C. In some embodiments, the solid material may have an aqueous solubility (or a solubility in a coating solution) of at least about 1 pg/mL, at least about 10 pg/mL, at least about 0.1 ng/mL, at least about 1 ng/mL, at least about 10 ng/mL, at least about 0.1 µg/mL, at least about 1 µg/mL, at least about 5 µg/mL, at least about 0.01 mg/mL, at least about 0.05 mg/mL, at least about 0.1 mg/mL, at least about 0.5 mg/mL, at least about 1.0 mg/mL, at least about 2 mg/mL. Combinations of the above-noted ranges are possible (e.g., an aqueous solubility or a solubility in a coating solution of at least about 10 pg/mL and less than about or equal to about 1 mg/mL). Other ranges are also possible. The solid material may have these or other ranges of aqueous solubilities at any point throughout the pH range (e.g., from pH 1 to pH 14).

In some embodiments, the core may be formed of a material within one of the ranges of solubilities classified by the U.S. Pharmacopeia Convention: e.g., very soluble: >1,000 mg/mL; freely soluble: 100-1,000 mg/mL; soluble: 33-100 mg/mL; sparingly soluble: 10-33 mg/mL; slightly soluble: 1-10 mg/mL; very slightly soluble: 0.1-1 mg/mL; and practically insoluble: <0.1 mg/mL.

Although a core may be hydrophobic or hydrophilic, in many embodiments described herein, the core is substantially hydrophobic. "Hydrophobic" and "hydrophilic" are given their ordinary meaning in the art and, as will be understood by those skilled in the art, in many instances herein, are relative terms. Relative hydrophobicities and hydrophilicities of materials can be determined by measuring the contact angle of a water droplet on a planar surface of the substance to be measured, e.g., using an instrument such as a contact angle goniometer and a packed powder of the core material.

In some embodiments, a material (e.g., a material forming a particle core) has a contact angle of at least about 20 degrees, at least about 30 degrees, at least about 40 degrees, at least about 50 degrees, at least about 60 degrees, at least about 70 degrees, at least about 80 degrees, at least about 90 degrees, at least about 100 degrees, at least about 110 degrees, at least about 120 degrees, or at least about 130 degrees. In some embodiments, a material has a contact angle of less than or equal to about 160 degrees, less than or equal to about 150 degrees, less than or equal to about 140 degrees, less than or equal to about 130 degrees, less than or equal to about 120 degrees, less than or equal to about 110 degrees, less than or equal to about 100 degrees, less than or equal to about 90 degrees, less than or equal to about 80 degrees, or less than or equal to about 70 degrees. Combinations of the above-referenced ranges are also possible (e.g., a contact angle of at least about 30 degrees and less than or equal to about 120 degrees). Other ranges are also possible.

Contact angle measurements can be made using a variety of techniques; here a static contact angle measurement between a pellet of the starting material which will be used to form the core and a bead of water is referenced. The material used to form the core was received as a fine powder or otherwise was ground into a fine powder using a mortar and pestle. In order to form a surface on which to make measurements, the powder was packed using a 7 mm pellet die set from International Crystal Labs. The material was added to the die and pressure was applied by hand to pack the powder into a pellet, no pellet press or high pressure was used. The pellet was then suspended for testing so that the top and bottom of the pellet (defined as the surface water is added to and the opposite parallel surface respectively) were not in contact with any surface. This was done by not fully removing the pellet from the collar of the die set. The pellet therefore touches the collar on the sides and makes no contact on the top or bottom. For contact angle measurements, water was added to the surface of the pellet until a bead of water with a steady contact angle over 30 seconds was obtained. The water was added into the bead of water by submerging or contacting the tip of the pipette or syringe used for addition to the bead of water. Once a stable bead of water was obtained, an image was taken and the contact angle was measured using standard practices.

In embodiments in which the core comprises an inorganic material (e.g., for use as imaging agents), the inorganic material may include, for example, a metal (e.g., Ag, Au, Pt, Fe, Cr, Co, Ni, Cu, Zn, and other transition metals), a semiconductor (e.g., silicon, silicon compounds and alloys, cadmium selenide, cadmium sulfide, indium arsenide, and indium phosphide), or an insulator (e.g., ceramics such as silicon oxide). The inorganic material may be present in the core in any suitable amount, e.g., at least about 1 wt %, at least about 5 wt %, at least about 10 wt %, at least about 20 wt %, at least about 30 wt %, at least about 40 wt %, at least about 50 wt %, at least about 75 wt %, at least about 90 wt %, or at least about 99 wt %. In one embodiment, the core is formed of 100 wt % inorganic material. In some cases, the inorganic material may be present in the core at less than about100 wt %, less than about 90 wt %, less than about 80 wt %, less than about 70 wt %, less than about 60 wt %, less than about 50 wt %, less than about 40 wt %, less than about 30 wt %, less than about 20 wt %, less than about 10 wt %, less than about 5 wt %, less than about 2 wt %, or less than about 1 wt %. Combinations of the above-referenced ranges are also possible (e.g., present in an amount of at least about 1 wt % and less than about 20 wt %). Other ranges are also possible.

The core may, in some cases, be in the form of a quantum dot, a carbon nanotube, a carbon nanowire, or a carbon nanorod. In some cases, the core comprises, or is formed of, a material that is not of biological origin.

In some embodiments, the core includes one or more organic materials such as a synthetic polymer and/or a natural polymer. Examples of synthetic polymers include non-degradable polymers such as polymethacrylate and degradable polymers such as polylactic acid, polyglycolic acid and copolymers thereof. Examples of natural polymers include hyaluronic acid, chitosan, and collagen. Other examples of polymers that may be suitable for portions of the core include those herein suitable for forming coatings on particles, as described below. A polymer may be present in the core in any suitable amount, e.g., less than about 100 wt %, less than about 90 wt %, less than about 80 wt %, less than about 70 wt %, less than about 60 wt %, less than about 50 wt %, less than about 40 wt %, less than about 30 wt %, less than about 20 wt %, less than about 10 wt %, less than about 5 wt %, less than about 2 wt %, or less than about 1 wt %. In some cases, the polymer may be present in an amount of at least about 1 wt %, at least about 5 wt %, at least about 10 wt %, at least about 20 wt %, at least about 30 wt %, at least about 40 wt %, at least about 50 wt %, at least about 75 wt %, at least about 90 wt %, or at least about 99 wt % in the core. Combinations of the above-referenced ranges are also possible (e.g., present in an amount of at least about 1 wt % and less than about 20 wt %). Other ranges are also possible. In one set of embodiments, the core is formed is substantially free of a polymeric component.

The core may have any suitable shape and/or size. For instance, the core may be substantially spherical, non-spherical, oval, rod-shaped, pyramidal, cube-like, disk-shaped, wire-like, or irregularly shaped. The core may have a largest or smallest cross-sectional dimension of, for example, less than or equal to about 10 µm, less than or equal to about 5 µm, less than or equal to about 1 µm, less than or equal to about 800 nm, less than or equal to about 700 nm, less than or equal to about 500 nm, less than or equal to 400 nm, less than or equal to about 300 nm, less than or equal to about 200 nm, less than or equal to about 100 nm, less than or equal to about 75 nm, less than or equal to about 50 nm, less than or equal to about 40 nm, less than or equal to about 35 nm, less than or equal to about 30 nm, less than or equal to about 25 nm, less than or equal to about 20 nm, less than or equal to about 15 nm, or less than or equal to about 5 nm. In some cases, the core may have a largest or smallest cross-sectional dimension of, for example, at least about 5 nm, at least about 20 nm, at least about 50 nm, at least about 100 nm, at least about 200 nm, at least about 300 nm, at least about 400 nm, at least about 500 nm, at least about 1 μm, or at least about 5 μm. Combinations of the above-referenced ranges are also possible (e.g., a largest or smallest cross-sectional dimension of at least about 50 nm and less than about 500 nm). Other ranges are also possible. In some embodiments, the sizes of the cores formed by a process described herein have a Gaussian-type distribution. Unless indicated otherwise, the measurements of particle/core sizes herein refer to the smallest cross-sectional dimension.

Those of ordinary skill in the art are familiar with techniques to determine sizes (e.g., smallest or largest cross-sectional dimensions) of particles. Examples of suitable techniques include (DLS), transmission electron microscopy, scanning electron microscopy, electroresistance counting and laser diffraction. Other suitable techniques are known to those or ordinary skill in the art. Although many methods for determining sizes of particles are known, the sizes described herein (e.g., average particle sizes, thicknesses) refer to ones measured by dynamic light scattering.

Methods of Forming Core Particles and Coated Particles

The core particles described herein may be formed by any suitable method. In some embodiments, a milling process is used to reduce the size of a solid material to form particles in the micrometer to nanometer size range. Dry and wet milling processes such as jet milling, cryo-milling, ball milling, media milling, and homogenization are known and can be used in methods described herein. Generally, in a wet milling process, a suspension of the material to be used as the core is mixed with milling media with or without excipients to reduce particle size. Dry milling is a process wherein the material to be used as the core is mixed with milling media with or without excipients to reduce particle size. In a cryo-milling process, a suspension of the material to be used as the core is mixed with milling media with or without excipients under cooled temperatures.

In some embodiments, the core particles described herein may be produced by nanomilling of a solid material (e.g., a pharmaceutical agent) in the presence of one or more stabilizers/surface-altering agents. Small particles of a solid material may require the presence of one or more stabilizers/surface-altering agents, particularly on the surface of the particles, in order to stabilize a suspension of particles without agglomeration or aggregation in a liquid solution. In some such embodiments, the stabilizer may act as a surface-altering agent, forming a coating on the particle.

As described herein, in some embodiments, a method of forming a core particle involves choosing a stabilizer that is suitable for both nanomilling and for forming a coating on the particle and rendering the particle mucus penetrating. For example, as described in more detail below, it has been demonstrated that 200-500 nm nanoparticles of a model compound pyrene produced by nanomilling of pyrene in the presence of Pluronic® F127 resulted in particles that can penetrate physiological mucus samples at the same rate as well-established polymer-based MPP. Interestingly, it was observed that only a handful of stabilizers/surface-altering agents tested fit the criteria of being suitable for both nanomilling and for forming a coating on the particle that renders the particle mucus penetrating, as described in more detail below.

In a wet milling process, milling can be performed in a dispersion (e.g., an aqueous dispersion) containing one or more stabilizers (e.g., a surface-altering agent), a grinding medium, a solid to be milled (e.g., a solid pharmaceutical agent), and a solvent. Any suitable amount of a stabilizer/surface-altering agent can be included in the solvent. In some embodiments, a stabilizer/surface-altering agent may be present in the solvent in an amount of at least about 0.001% (wt % or % weight to volume (w:v)), at least about 0.01%, at least about 0.1%, at least about 0.5%, at least about 1%, at least about 2%, at least about 3%, at least about 4%, at least about 5%, at least about 6%, at least about 7%, at least about 8%, at least about 10%, at least about 12%, at least about 15%, at least about 20%, at least about 40%, at least about 60%, or at least about 80% of the solvent. In some cases, the stabilizer may be present in the solvent in an amount of about 100% (e.g., in an instance where the stabilizer/surface-altering agent is the solvent). In other embodiments, the stabilizer may be present in the solvent in an amount of less than or equal to about 100%, less than or equal to about 80%, less than or equal to about 60%, less than or equal to about 40%, less than or equal to about 20%, less than or equal to about 15%, less than or equal to about 12%, less than or equal to about 10%, less than or equal to about 8%, less than or equal to about 7%, less than or equal to about 6%, less than or equal to about 5%, less than or equal to about 4%, less than or equal to about 3%, less than or equal to about 2%, or less than or equal to about 1% of the solvent. Combinations of the above-referenced ranges are also possible (e.g., an amount of less than or equal to about 5% and at least about 1% of the solvent). Other ranges are also possible. The particular range chosen may influence factors that may affect the ability of the particles to penetrate mucus such as the stability of the coating of the stabilizer/surface-altering agent on the particle surface, the average thickness of the coating of the stabilizer/surface-altering agent on the particles, the orientation of the stabilizer/surface-altering agent on the particles, the density of the stabilizer/surface altering agent on the particles, stabilizer:drug ratio, drug concentration, the size and polydispersity of the particles formed, and the morphology of the particles formed.

The pharmaceutical agent (or salt thereof) may be present in the solvent in any suitable amount. In some embodiments, the pharmaceutical agent (or salt thereof) is present in an amount of at least about 0.001% (wt % or % weight to volume (w:v)), at least about 0.01%, at least about 0.1%, at least about 0.5%, at least about 1%, at least about 2%, at least about 3%, at least about 4%, at least about 5%, at least about 6%, at least about 7%, at least about 8%, at least about 10%, at least about 12%, at least about 15%, at least about 20%, at least about 40%, at least about 60%, or at least about 80% of the solvent. In some cases, the pharmaceutical agent (or salt thereof) may be present in the solvent in an amount of less than or equal to about 100%, less than or equal to about 90%, less than or equal to about 80%, less than or equal to about 60%, less than or equal to about 40%, less than or equal to about 20%, less than or equal to about 15%, less than or equal to about 12%, less than or equal to about 10%, less than or equal to about 8%, less than or equal to about 7%, less than or equal to about 6%, less than or equal to about 5%, less than or equal to about 4%, less than or equal to about 3%, less than or equal to about 2%, or less than or equal to about 1% of the solvent. Combinations of the above-referenced ranges are also possible (e.g., an amount of less than or equal to about 20% and at least about 1% of the solvent). In some embodiments, the pharmaceutical agent is present in the above ranges but in w:v The ratio of stabilizer/surface-altering agent to pharmaceutical agent (or salt thereof) in a solvent may also vary. In some embodiments, the ratio of stabilizer/surface-altering agent to pharmaceutical agent (or salt thereof) may be at least 0.001:1 (weight ratio, molar ratio, or w:v ratio), at least 0.01:1, at least 0.01:1, at least 1:1, at least 2:1, at least 3:1, at least 5:1, at least 10:1, at least 25:1, at least 50:1, at least 100:1, or at least 500:1. In some cases, the ratio of stabilizer/surface-altering agent to pharmaceutical agent (or salt thereof) may be less than or equal to 1000:1 (weight ratio or molar ratio), less than or equal to 500:1, less than or equal to 100:1, less than or equal to 75:1, less than or equal to 50:1, less than or equal to 25:1, less than or equal to 10:1, less than or equal to 5:1, less than or equal to 3:1, less than or equal to 2:1, less than or equal to 1:1, or less than or equal to 0.1:1. Combinations of the above-referenced ranges are possible (e.g., a ratio of at least 5:1 and less than or equal to 50:1). Other ranges are also possible.

Stabilizers/surface-altering agents may be, for example, polymers or surfactants. Examples of polymers are those suitable for use in coatings, as described in more detail below. Non-limiting examples of surfactants include L-a-phosphatidylcholine (PC), 1,2-dipalmitoylphosphatidycholine (DPPC), oleic acid, sorbitan trioleate, sorbitan monooleate, sorbitan monolaurate, polyoxyethylene sorbitan monolaurate, polyoxyethylene sorbitan monooleate, natural lecithin, oleyl polyoxyethylene ether, stearyl polyoxyethylene ether, lauryl polyoxyethylene ether, block copolymers of oxyethylene and oxypropylene, synthetic lecithin, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, polyethylene glycol 400, cetyl pyridinium chloride, benzalkonium chloride, olive oil, glyceryl monolaurate, corn oil, cotton seed oil, and sunflower seed oil.

It should be appreciated that while in some embodiments the stabilizer used for milling forms a coating on a particle surface, which coating renders particle mucus penetrating, in other embodiments, the stabilizer may be exchanged with one or more other surface-altering agents after the particle has been formed. For example, in one set of methods, a first stabilizer/surface-altering agent may be used during a milling process and may coat a surface of a core particle, and then all or portions of the first stabilizer/surface-altering agent may be exchanged with a second stabilizer/surface-altering agent to coat all or portions of the core particle surface. In some cases, the second stabilizer/surface-altering agent may render the particle mucus penetrating more than the first stabilizer/surface-altering agent. In some embodiments, a core particle having a coating including multiple surface-altering agents may be formed.

Any suitable grinding medium can be used for milling. In some embodiments, a ceramic and/or polymeric material and/or a metal can be used. Examples of suitable materials may include zirconium oxide, silicon carbide, silicon oxide, silicon nitride, zirconium silicate, yttrium oxide, glass, alumina, alpha-alumina, aluminum oxide, polystyrene, poly(methyl methacrylate), titanium, steel. A grinding medium may have any suitable size. For example, the grinding medium may have an average diameter of at least about 0.1 mm, at least about 0.2 mm, at least about 0.5 mm, at least about 0.8 mm, at least about 1 mm, at least about 2 mm, or at least about 5 mm. In some cases, the grinding medium may have an average diameter of less than or equal to about 5 mm, less than or equal to about 2 mm, less than or equal to about 1 mm, less than or equal to about 0.8, less than or equal to about 0.5 mm, or less than or equal to about 0.2 mm. Combinations of the above-referenced ranges are also possible (e.g., an average diameter of at least about 0.5 millimeters and less than or equal to about 1 mm). Other ranges are also possible.

Any suitable solvent may be used for milling. The choice of solvent may depend on factors such as the solid material (e.g., pharmaceutical agent) being milled, the particular type of stabilizer/surface-altering agent being used (e.g., one that may render the particle mucus penetrating), the grinding material be used, among other factors. Suitable solvents may be ones that do not substantially dissolve the solid material or the grinding material, but dissolve the stabilizer/surface-altering agent to a suitable degree. Non-limiting examples of solvents may include water, buffered solutions, other aqueous solutions, alcohols (e.g., ethanol, methanol, butanol), and mixtures thereof that may optionally include other components such as pharmaceutical excipients, polymers, pharmaceutical agents, salts, preservative agents, viscosity modifiers, tonicity modifier, taste masking agents, antioxidants, pH modifier, and other pharmaceutical excipients. In other embodiments, an organic solvent can be used. A pharmaceutical agent may have any suitable solubility in these or other solvents, such as a solubility in one or more of the ranges described above for aqueous solubility or for solubility in a coating solution.

In other embodiments, core particles may be formed by a precipitation technique. Precipitation techniques (e.g., microprecipitation techniques, nanoprecipitation techniques) may involve forming a first solution comprising the material to be used as the core (e.g., a pharmaceutical agent) and a solvent, wherein the material is substantially soluble in the solvent. The solution may be added to a second solution comprising another solvent in which the material is substantially insoluble, thereby forming a plurality of particles comprising the material. In some cases, one or more surface-altering agents, surfactants, materials, and/or bioactive agents may be present in the first and/or second solutions. A coating may be formed during the process of precipitating the core (e.g., the precipitating and coating steps may be performed substantially simultaneously). In other embodiments, the particles are first formed using a precipitation technique, following by coating of the particles with a surface-altering agent.

In some embodiments, a precipitation technique may be used to form particles (e.g., nanocrystals) of a salt of a pharmaceutical agent. Generally, a precipitation technique involves dissolving the material to be used as the core in a solvent, which is then added to a miscible anti-solvent with or without excipients to form the core particle. This technique may be useful for preparing particles of pharmaceutical agents that are soluble in aqueous solutions (e.g., agents having a relatively high aqueous solubility). In some embodiments, pharmaceutical agents having one or more charged or ionizable groups can interact with a counter ion (e.g., a cation or an anion) to form a salt complex. For example, the pharmaceutical agent tenofovir (TFV) interacts very strongly with zinc cations via the phosphonate group and the purine ring structure. This interaction with zinc causes TFV precipitation into crystals that can be stabilized with the coatings described herein, halting aggregation.

A variety of counter ions can be used to form salt complexes, including metals (e.g., alkali metals, alkali earth metals and transition metals). Non-limiting examples of cationic counter ions include zinc, calcium, aluminum, zinc, barium, magnesium, and copper. Non-limiting examples of anionic counter ions include phosphate, carbonate, and fatty acids. Counter ions may be, for example, monovalent, divalent, or trivalent. Other counter ions are known in the art and can be used in the embodiments described herein.

A variety of different acids may be used in a precipitation process. In some embodiments, a suitable acid may include deconoic acid, hexanoic acid, mucic acid, octanoic acid. In other embodiments, a suitable acid may include acetic acid, adipic acid, L-ascorbic acid, L-aspartic acid, capric acid (decanoic acid), carbonic acid, citric acid, fumaric acid, galactaric acid, D-glucoheptonic acid, D-gluconic acid, D-glucuronic acid, glutamic acid, glutaric acid, glycerophosphoric acid, glycolic acid, hippuric acid, hydrochloric acid, DL-lactic acid, lauric acid, maleic acid, (−)-L-malic acid, palmitic acid, phosphoric acid, sebacic acid, stearic acid, succinic acid, sulfuric acid, (+)-L-tartaric acid, or thiocyanic acid. In other embodiments, a suitable acid may include alginic acid, benzenesulfonic acid, benzoic acid, (+)-camphoric acid, caprylic acid (octanoic acid), cyclamic acid, dodecylsulfuric acid, ethane-1,2-disulfonic acid, ethanesulfonic acid, ethanesulfonic acid, 2-hydroxy-, gentisic acid, glutaric acid, 2-oxo-, isobutyric acid, lactobionic acid, malonic acid, methanesulfonic acid, naphthalene-1,5-disulfonic acid, naphthalene-2-sulfonic acid, 2-naphthoic acid, 1-hydroxy-, nicotinic acid, oleic acid, orotic acid, oxalic acid, pamoic acid, (embonic acid), propionic acid, (−)-L-pyroglutamic acid, or p-toluenesulfonic acid. In yet other embodiments, a suitable acid may include acetic acid, 2,2-dichloro-, benzoic acid, 4-acetamido-, (+)-camphor-10-sulfonic acid, caproic acid (hexanoic acid), cinnamic acid, formic acid, hydrobromic acid, DL-mandelic acid, nitric acid, salicylic acid, salicylic acid, 4-amino-, or undecylenic acid (undec-10-enoic acid). Mixtures of one or more such acids can also be used.

A variety of different bases may be used in a precipitation process. In some embodiments, a suitable base includes ammonia, L-arginine, calcium hydroxide, choline, glucamine, N-methyl-, lysine, magnesium hydroxide, potassium hydroxide, or sodium hydroxide. In other embodiments, a suitable base may include benethamine, benzathine, betaine, deanol, diethylamine, ethanol, 2-(diethylamino)-, hydrabamine, morpholine, 4-(2-hydroxyethyl)-, pyrrolidine, 1-(2-hyroxyethyl)-, or tromethamine. In other embodiments, a suitable base may include diethanolamine (2,2'-iminobis(ethanol)), ethanolamine (2-aminoethanol), ethylenediamine, 1H-imidazole, piperazine, triethanolamine (2,2',2"-nitrilotris(ethanol)), or zinc hydroxide. Mixtures of one or more such bases can also be used.

Any suitable solvent can be used for precipitation, including the solvents described herein that may be used for milling. In one set of embodiments, an aqueous solution is used (e.g., water, buffered solutions, other aqueous solutions, alcohols (e.g., ethanol, methanol, butanol), and mixtures thereof that may optionally include other components such as pharmaceutical excipients, polymers, and pharmaceutical agents.

In the precipitation process, the salt may have a lower aqueous solubility (or solubility in the solvent containing the salt) than the pharmaceutical agent in the non-salt form. The aqueous solubility (or solubility in the solvent) of the salt may be, for example, less than about or equal to about 5 mg/mL, less than or equal to about 2 mg/mL, less than or equal to about 1 mg/mL, less than or equal to about 0.5 mg/mL, less than or equal to about 0.1 mg/mL, less than or equal to about 0.05 mg/mL, or less than or equal to about 0.01 mg/mL, less than or equal to about 1 µg/mL, less than or equal to about 0.1 µg/mL, less than or equal to about 0.01 µg/mL, less than or equal to about 1 ng/mL, less than or equal to about 0.1 ng/mL, or less than or equal to about 0.01 ng/mL at 25° C. In some embodiments, the salt may have an aqueous solubility (or solubility in the solvent) of at least about 1 pg/mL, at least about 10 pg/mL, at least about 0.1 ng/mL, at least about 1 ng/mL, at least about 10 ng/mL, at least about 0.1 µg/mL, at least about 1 µg/mL, at least about 5 µg/mL, at least about 0.01 mg/mL, at least about 0.05 mg/mL, at least about 0.1 mg/mL, at least about 0.5 mg/mL, at least about 1.0 mg/mL, at least about 2 mg/mL. Combinations of the above-noted ranges are possible (e.g., an aqueous solubility (or solubility in the solvent) of at least about 0.001 mg/mL and less than about or equal to about 1 mg/mL). Other ranges are also possible. The salt may have these or other ranges of aqueous solubilities at any point throughout the pH range (e.g., from pH 1 to pH 14).

In some embodiments, the solvent used for precipitation includes one or more surface-altering agents as described herein, and a coating of the one or more surface-altering agents may be formed around the particle as it precipitates out of solution. The surface-altering agent may be present in the solvent at any suitable concentration, such as a concentration of at least about 0.001% (w/v), at least about 0.005% (w/v), at least about 0.01% (w/v), at least about 0.05% (w/v), at least about 0.1% (w/v), at least about 0.5% (w/v), at least about 1% (w/v), or at least about 5% (w/v) in the aqueous solution. In some instances, the surface-altering agent is present in the solvent at a concentration of less than or equal to about 5% (w/v), less than or equal to about 1% (w/v), less than or equal to about 0.5% (w/v), less than or equal to about 0.1% (w/v), less than or equal to about 0.05% (w/v), less than or equal to about 0.01% (w/v), or less than or equal to about 0.005% (w/v). Combinations of the above-referenced ranges are also possible (e.g., a concentration of at least about 0.01 (w/v) and less than or equal to about 1% (w/v). Other ranges are also possible.

Another exemplary method of forming a core particle includes a freeze-drying technique. In this technique, a pharmaceutical agent or salt thereof may be dissolved in an aqueous solution, optionally containing a surface-altering agent. A counter ion may be added to the solution, and the solution may be immediately flash frozen and freeze dried. Dry powder can be reconstituted in a suitable solvent (e.g., an aqueous solution such as water) at a desired concentration.

A counter ion may be added to a solvent for freeze-drying in any suitable range. In some cases, the ratio of counter ion to pharmaceutical agent (e.g., salt) may be at least 0.1:1 (weight ratio or molar ratio), at least 1:1, at least 2:1, at least 3:1, at least 5:1, at least 10:1, at least 25:1, at least 50:1, or at least 100:1. In some cases, the ratio of counter ion to pharmaceutical agent (e.g., salt) may be less than or equal to 100:1 (weight ratio or molar ratio), less than or equal to 75:1, less than or equal to 50:1, less than or equal to 25:1, less than or equal to 10:1, less than or equal to 5:1, less than or equal to 3:1, less than or equal to 2:1, less than or equal to 1:1, or less than or equal to 0.1:1. Combinations of the above-referenced ranges are possible (e.g., a ratio of at least 5:1 and less than or equal to 50:1). Other ranges are also possible.

If the surface-altering agent is present in the solvent prior to freeze drying, it may be present at any suitable concentration, such as a concentration of at least about 0.001% (w/v), at least about 0.005% (w/v), at least about 0.01% (w/v), at least about 0.05% (w/v), at least about 0.1% (w/v), at least about 0.5% (w/v), at least about 1% (w/v), or at least about 5% (w/v) in the aqueous solution. In some instances, the surface-altering agent is present in the solvent at a concentration of less than or equal to about 5% (w/v), less than or equal to about 1% (w/v), less than or equal to about 0.5% (w/v), less than or equal to about 0.1% (w/v), less than or equal to about 0.05% (w/v), less than or equal to about 0.01% (w/v), or less than or equal to about 0.005% (w/v). Combinations of the above-referenced ranges are also possible (e.g., a concentration of at least about 0.01% (w/v) and less than or equal to about 1% (w/v). Other ranges are also possible.

The concentration of surface-altering agent present in the solvent may be above or below the critical micelle concentration (CMC) of the surface-altering agent, depending on the particular surface-altering agent used. For example, as described in the Examples section, F127 concentrations both above (1%) and below (0.08%) the CMC of F127 can be used to coat stable nanocrystal particles of the pharmaceutical agent tenofovir. However, nanocrystal particles of acyclovir monophosphate were much more sensitive to surfactant concentration, and stable nanocrystal particles could only be formed when using F127 concentrations below the CMC (~0.1%).

In other embodiments, stable particles can be formed by adding excess counter ion to a solution containing a pharmaceutical agent. The precipitate can then be washed by various methods such as centrifugation. The resultant slurry may be sonicated. One or more surface-altering agents may be added to stabilize the resultant particles.

Other methods of forming particles of a pharmaceutical agent are also possible. So called top-down techniques include, for example, milling techniques and high pressure homogenization. In high pressure homogenization, a suspension of the material to be used as the core is forced under pressure through a gap, valve, or aperture in order to reduce particle size. So called bottom-up techniques include, for example, precipitation, emulsification, wherein the material to be used as the core dissolved in a solvent is added to an immiscible anti-solvent with or without excipients to form the core particle; and spray drying, wherein a solution of the material to be used as the core in sprayed into a gas phase anti-solvent to form the core particle. Combinations of the methods described herein and other methods are also possible. For example, in some embodiments, a core of a pharmaceutical agent is first formed by precipitation, and then the size of the core is further reduced by a milling process.

Following formation of particles of a pharmaceutical agent, the particles may be optionally exposed to a solution comprising a (second) surface-altering agent that may associate with and/or coat the particles. In embodiments in which the pharmaceutical agent already includes a coating of a first surface-altering agent, all or portions of a second surface-altering agent may be exchanged with a second stabilizer/surface-altering agent to coat all or portions of the particle surface. In some cases, the second surface-altering agent may render the particle mucus penetrating more than the first surface-altering agent. In other embodiments, a particle having a coating including multiple surface-altering agents may be formed (e.g., in a single layer or in multiple layers). In other embodiments, a particle having multiple coatings (e.g., each coating optionally comprising different surface-altering agents) may be formed. In some cases, the coating is in the form of a monolayer of a surface-altering agent. Other configurations are also possible.

In any of the methods described herein, a particle may be coated with a surface-altering agent by incubating the particle in a solution with the surface-altering agent for a period of at least about 1 minutes, at least about 2 minutes, at least about 5 min., at least about 10 min., at least about 15 min., at least about 20 min., at least about 30 min., at least about 60 min., or more. In some cases, incubation may take place for a period of less than or equal to about 10 hours, less than or equal to about 5 hours, or less than or equal to about 60 min. Combinations of the above referenced ranges are also possible (e.g., an incubation period of less than or equal to 60 min. and at least about 2 min.).

Particle Coatings

As shown in the embodiment illustrated in FIG. 1, core 16 may be surrounded by coating 20 comprising one or more surface-altering agents. The particular chemical makeup and/or components of the coating and surface-altering agent(s) can be chosen so as to impart certain functionality to the particles, such as enhanced transport through mucosal barriers.

It should be understood that a coating which surrounds a core need not completely surround the core, although such embodiments may be possible. For example, the coating may surround at least about 10%, at least about 30%, at least about 50%, at least about 60%, at least about 70%, at least about 80%, at least about 90%, or at least about 99% of the surface area of a core. In some cases, the coating substantially surrounds a core. In other cases, the coating completely surrounds a core. In other embodiments, a coating surrounds less than or equal to about 100%, less than or equal to about 90%, less than or equal to about 80%, less than or equal to about 70%, less than or equal to about 60%, or less than or equal to about 50% of the surface area of a core. Combinations of the above-referenced ranges are also possible (e.g., surrounding greater than 80% and less than 100% of the surface area of a core).

The components of the coating may be distributed evenly across a surface of the core in some cases, and unevenly in other cases. For example, the coating may include portions (e.g., holes) that do not include any material in some cases. If desired, the coating may be designed to allow penetration and/or transport of certain molecules and components into or out of the coating, but may prevent penetration and/or transport of other molecules and components into or out of the coating. The ability of certain molecules to penetrate and/or be transported into and/or across a coating may depend on, for example, the packing density of the surface-altering agents forming the coating and the chemical and physical properties of the components forming the coating. As described herein, the coating may include one layer of material, or multilayers of materials in some embodiments. A single type of surface-altering agent may be present, or multiple types of surface-altering agent.

A coating of a particle can have any suitable thickness. For example, a coating may have an average thickness of at least about 1 nm, at least about 5 nm, at least about 10 nm, at least about 30 nm, at least about 50 nm, at least about 100 nm, at least about 200 nm, at least about 500 nm, at least about 1 μm, or at least about 5 μm. In some cases, the average thickness of a coating is less than or equal to about 5 μm, less than or equal to about 1 μm, less than or equal to about 500 nm, less than or equal to about 200 nm, less than or equal to about 100 nm, less than a to about 50 nm, less than or equal to about 30 nm, less than or equal to about 10 nm, or less than or equal to about 5 nm. Combinations of the above-referenced ranges are also possible (e.g., an average thickness of at least about 1 nm and less than or equal to about 100 nm). Other ranges are also possible. For particles having multiple coatings, each coating layer may have one of the thicknesses described above.

In some embodiments, the compositions and methods described herein may allow for the coating of a core particle with hydrophilic surface-alternating moieties without requiring covalent linking of the surface-altering moieties to the core surface. In some such embodiments, a core having a hydrophobic surface may be coated with a polymer described herein, thereby causing a plurality of surface-altering moieties to be on the core surface without substantially altering the characteristics of the core itself. In other embodiments, however, a surface-altering agent is covalently linked to a core particle.

The coating and/or surface-altering agent of a particle described herein may comprise any suitable material, such as a hydrophobic material, a hydrophilic material, and/or an amphiphilic material. In some embodiments, the coating includes a polymer. In certain embodiments, the polymer is a synthetic polymer (i.e., a polymer not produced in nature). In other embodiments, the polymer is a natural polymer (e.g., a protein, polysaccharide, rubber). In certain embodiments, the polymer is a surface active polymer. In certain embodiments, the polymer is a non-ionic polymer. In certain embodiments, the polymer is a non-ionic block copolymer. In some embodiments, the polymer may be a diblock copolymer, a triblock copolymer, e.g., e.g., where one block is a hydrophobic polymer and another block is a hydrophilic polymer. The polymer may be charged or uncharged.

In some embodiments, the particles described herein include a coating comprising a block copolymer having a relatively hydrophilic block and a relatively hydrophobic block. In some cases, the hydrophilic blocks may be substantially present at the outer surface of the particle. For example, the hydrophilic blocks may form a majority of the outer surface of the coating and may help stabilize the particle in an aqueous solution containing the particle. The hydrophobic block may be substantially present in the interior of the coating and/or at the surface of the core particle, e.g., to facilitate attachment of the coating to the core. In some instances, the coating comprises a surface-altering agent including a triblock copolymer, wherein the triblock copolymer comprises a hydrophilic block-hydrophobic block-hydrophilic block configuration.

The molecular weight of the hydrophilic blocks and the hydrophobic blocks of the triblock copolymers may be selected so as to reduce the mucoadhesion of a core and to ensure sufficient association of the triblock copolymer with the core, respectively. As described herein, the molecular weight of the hydrophobic block of the triblock copolymer may be chosen such that adequate association of the triblock copolymer with the core occurs, thereby increasing the likelihood that the triblock copolymer remains adhered to the core. Surprisingly, it was discovered that in certain embodiments, too low of a molecular weight of the hydrophobic blocks of the triblock copolymer (e.g., less than about 2 kDa) does not allow for sufficient adhesion between a hydrophobic core and the triblock copolymer, and thus, particles with such hydrophobic blocks may not exhibit sufficient reduced mucoadhesion.

In certain embodiments, the molecular weight of a hydrophobic block of a triblock copolymer (e.g., the PPO block of the triblock copolymer PEG-PPO-PEG, where the PEG block may be interchanged with PEO block) is at least about 2 kDa, at least about 3 kDa, at least about 4 kDa, at least about 5 kDa, at least about 6 kDa, at least about 10 kDa, at least about 20 kDa, or at least about 50 kDa. In some embodiments, the molecular weight of the hydrophobic block is less than or equal to about 100 kDa, less than or equal to about 80 kDa, less than or equal to about 50 kDa, less than or equal to about 20 kDa, less than or equal to about 15 kDa, less than or equal to about 13 kDa, less than or equal to about 12 kDa, less than or equal to about 10 kDa, less than or equal to about 8 kDa, or less than or equal to about 6 kDa. Combinations of the above-mentioned ranges are also possible (e.g., at least about 3 kDa and less than or equal to about 15 kDa). Other ranges are also possible.

It was also discovered that in certain embodiments, a sufficient amount of the hydrophilic blocks (as a function of the total weight of the polymer) was needed for the particles to exhibit sufficient reduced mucoadhesion. For example, in certain embodiments, hydrophilic blocks making up at least about 15 wt % (e.g., at least about 20 wt %, at least about 25 wt %, or at least about 30 wt %) of the triblock copolymer rendered the particles mucus penetrating, whereas mucoadhesion was generally observed with particles having weight percentages of hydrophilic blocks below this limit. In some embodiments, the hydrophilic blocks of a triblock copolymer constitute at least about 15 wt %, at least about 20 wt %, at least about 25 wt %, at least about 30 wt %, at least about 35 wt %, at least about 40 wt %, at least about 45 wt %, at least about 50 wt %, at least about 55 wt %, at least about 60 wt %, at least about 65 wt %, or at least about 70 wt % of the triblock copolymer. In some embodiments, the hydrophilic blocks of a triblock copolymer constitute less than or equal to about 90 wt %, less than or equal to about 80 wt %, less than or equal to about 60 wt %, less than or equal to about 50 wt %, or less than or equal to about 40 wt % of the triblock copolymer. Combinations of the above-referenced ranges are also possible (e.g., at least about 30 wt % and less than or equal to about 80 wt %). Other ranges are also possible.

In some embodiments, the molecular weight of a hydrophilic block (e.g., a PEG (or PEO) block of the triblock copolymer PEG-PPO-PEG, where a PEG block may be interchanged with a PEO block) may be at least about 0.05 kDa, at least about 0.1 kDa, at least about 0.2 kDa, at least about 0.3 kDa, at least about 0.4 kDa, at least about 0.5 kDa, at least about 1 kDa, at least about 2 kDa, at least about 3 kDa, at least about 4 kDa, at least about 5 kDa, or at least about 6 kDa, at least about 8 kDa, at least about 10 kDa, at least about 20 kDa, or at least about 50 kDa. In certain embodiments, the molecular weight of a hydrophilic block may be less than or equal to about 100 kDa, less than or equal to about 80 kDa, less than or equal to about 50 kDa, less than or equal to about 20 kDa, less than or equal to about 15 kDa, less than or equal to about 10 kDa, less than or equal to about 9 kDa, less than or equal to about 8 kDa, less than or equal to about 7 kDa, less than or equal to about 6 kDa, less than or equal to about 5 kDa, less than or equal to about 3 kDa, less than or equal to about 2 kDa, or less than or equal to about 1 kDa. Combinations of the above-mentioned ranges are also possible (e.g., at least about 0.1 kDa and less than or equal to about 3 kDa). Other ranges are also possible. In embodiments in which two hydrophilic blocks flank a hydrophobic block, the molecular weights of the two hydrophilic blocks may be substantially the same or different.

In certain embodiments, the polymer of a surface-altering agent includes a polyether portion. In certain embodiments, the polymer includes a polyalkylether portion. In certain embodiments, the polymer includes polyethylene glycol tails. In certain embodiments, the polymer includes a polypropylene glycol central portion. In certain embodiments, the polymer includes polybutylene glycol as the central portion. In certain embodiments, the polymer includes polypentylene glycol as the central portion. In certain embodiments, the polymer includes polyhexylene glycol as the central portion. In certain embodiments, the polymer is a triblock copolymer of one of the polymers described herein. As disclosed herein, any recitation of PEG may be replaced with polyethylene oxide (PEO), and any recitation of PEO may be replaced with PEG.

In certain embodiments, the polymer is a triblock copolymer of a polyalkyl ether (e.g., polyethylene glycol, polypropylene glycol) and another polymer. In certain embodiments, the polymer is a triblock copolymer of a polyalkyl ether and another polyalkyl ether. In certain embodiments, the polymer is a triblock copolymer of polyethylene glycol and another polyalkyl ether. In certain embodiments, the polymer is a triblock copolymer of polypropylene glycol and another polyalkyl ether. In certain embodiments, the polymer is a triblock copolymer with at least one unit of polyalkyl ether. In certain embodiments, the polymer is a triblock copolymer of two different polyalkyl ethers. In certain embodiments, the polymer is a triblock copolymer including a polyethylene glycol unit. In certain embodiments, the polymer is a triblock copolymer including a polypropylene glycol unit. In certain embodiments, the polymer is a triblock copolymer of a more hydrophobic unit flanked by two more hydrophilic units. In certain embodiments, the hydrophilic units are the same type of polymer. In certain embodiments, the polymer includes a polypropylene glycol unit flanked by two more hydrophilic units. In certain embodiments, the polymer includes two polyethylene glycol units flanking a more hydrophobic unit. In certain embodiments, the polymer is a triblock copolymer with a polypropylene glycol unit flanked by two polyethylene glycol units. The molecular weights of the two blocks flanking the central block may be substantially the same or different.

In certain embodiments, the polymer is of the formula:

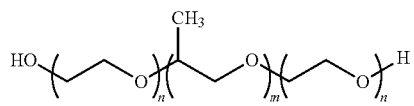

wherein n is an integer between 2 and 1140, inclusive; and m is an integer between 2 and 1730, inclusive. In certain embodiments, n is an integer between 10 and 170, inclusive. In certain embodiments, m is an integer between 5 and 70 inclusive. In certain embodiments, n is at least 2 times m, 3 times m, or 4 times m.

In certain embodiments, the coating includes a surface-altering agent comprising a (poly(ethylene glycol))-(poly(propylene oxide))-(poly(ethylene glycol)) triblock copolymer (hereinafter "PEG-PPO-PEG triblock copolymer"). As described herein, the PEG blocks may be interchanged with PEO blocks in some embodiments. The molecular weights of the PEG (or PEO) and PPO segments of the PEG-PPO-PEG triblock copolymer may be selected so as to reduce the mucoadhesion of the particle, as described herein. Without wishing to be bound by theory, a particle having a coating comprising a PEG-PPO-PEG triblock copolymer may have reduced mucoadhesion as compared to a control particle due to, at least in part, the display of a plurality of PEG (or PEO) segments on the particle surface. The PPO segment may be adhered to the core surface (e.g., in the case of the core surface being hydrophobic), thus allowing for a strong association between the core and the triblock copolymer. In some cases, the PEG-PPO-PEG triblock copolymer is associated with the core through non-covalent interactions. For purposes of comparison, the control particle may be, for example, a carboxylate-modified polystyrene particle of similar size as the coated particle in question.

In certain embodiments, a surface-altering agent includes a polymer comprising a poloxamer, having the trade name Pluronic®. Pluronic® polymers that may be useful in the embodiments described herein include, but are not limited to, F127, F38, F108, F68, F77, F87, F88, F98, L101, L121, L31, L35, L43, L44, L61, L62, L64, L81, L92, N3, P103, P104, P105, P123, P65, P84, and P85.

Examples of molecular weights of certain Pluronic® molecules are shown in Table 1.

TABLE 1

Molecular Weights of Pluronic ® molecules

| Pluronic ® | Average MW | MW PPO | PEO wt % | MW PEO |
|---|---|---|---|---|
| L31 | 1000 | 900 | 10 | 100 |
| L44 | 2000 | 1200 | 40 | 800 |
| L81 | 2667 | 2400 | 10 | 267 |
| L101 | 3333 | 3000 | 10 | 333 |
| P65 | 3600 | 1800 | 50 | 1800 |
| L121 | 4000 | 3600 | 10 | 400 |
| P103 | 4286 | 3000 | 30 | 1286 |
| F38 | 4500 | 900 | 80 | 3600 |
| P123 | 5143 | 3600 | 30 | 1543 |
| P105 | 6000 | 3000 | 50 | 3000 |
| F87 | 8000 | 2400 | 70 | 5600 |
| F68 | 9000 | 1800 | 80 | 7200 |
| F127 | 12000 | 3600 | 70 | 8400 |
| P123 | 5750 | 4030 | 30 | 1730 |

Although other ranges may be possible and useful in certain embodiments described herein, in some embodiments, the hydrophobic block of the PEG-PPO-PEG triblock copolymer has one of the molecular weights described above (e.g., at least about 3 kDa and less than or equal to about 15 kDa), and the combined hydrophilic blocks have a weight percentage with respect to the polymer in one of the ranges described above (e.g., at least about 15 wt %, at least about 20 wt %, at least about 25 wt %, or at least about 30 wt %, and less than or equal to about 80 wt %). Certain Pluronic polymers that fall within these criteria include, for example, F127, F108, P105 and P103. Surprisingly, and as described in more detail in the Examples, it was found that these particular Pluronic® polymers rendered particles mucus penetrating more than other Pluronic® polymers tested that did not fall within this criteria. Additionally, other agents that did not render particles mucus penetrating included certain polymers such as polyvinylpyrrolidones (PVP/Kollidon), polyvinyl alcohol-polyethylene glycol graft-copolymer (Kollicoat IR), hydroxypropyl methylcellulose (Methocel); oligomers such as Tween 20, Tween 80, solutol HS 15, Triton X100, tyloxapol, cremophor RH 40; small molecules such as Span 20, Span 80, octyl glucoside, cetytrimethylammonium bromide (CTAB), sodium dodecyl sulfate (SDS).

Although much of the description herein involves coatings comprising a hydrophilic block-hydrophobic block-hydrophilic block configuration (e.g., a PEG-PPO-PEG triblock copolymer), it should be appreciated that the coatings are not limited to this configuration and that other configurations and materials are possible. For example, a particle may include more than one coating (e.g., at least two, three, four, five, or more coatings), and each coating need not be formed of or comprise a mucus penetrating material. In some cases, an intermediate coating (i.e., a coating between the core surface and an outer coating) may include a polymer that facilitates attachment of an outer coating to the core surface. In many embodiments, an outer coating of a particle includes a polymer comprising a material that facilitates the transport of the particle through mucus.

As such, a coating (e.g., an inner coating, an intermediate coating, and/or an outer coating) may include any suitable polymer. In some cases, the polymer may be biocompatible and/or biodegradable. In some cases, the polymeric material may comprise more than one type of polymer (e.g., at least two, three, four, five, or more, polymers). In some cases, a polymer may be a random copolymer or a block copolymer (e.g., a diblock copolymer, a triblock copolymer) as described herein.

Non-limiting examples of suitable polymers may include polyamines, polyethers, polyamides, polyesters, polycarbamates, polyureas, polycarbonates, polystyrenes, polyimides, polysulfones, polyurethanes, polyacetylenes, polyethylenes, polyethyeneimines, polyisocyanates, polyacrylates, polymethacrylates, polyacrylonitriles, and polyarylates. Non-limiting examples of specific polymers include poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacrylate, polyurethane, poly-L-lysine (PLL), hydroxypropyl methacrylate (HPMA), poly(ethylene glycol), poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth)acrylate), poly(butyl(meth)acrylate), poly(isobutyl(meth)acrylate), poly(hexyl(meth)acrylate), poly(isodecyl(meth)acrylate), poly(lauryl(meth)acrylate), poly(phenyl(meth)acrylate), poly(methyl acrylate), poly(isopropyl acrylate), poly(isobutyl acrylate), poly(octadecyl acrylate) (jointly referred to herein as "polyacrylic acids"), and copolymers and mixtures thereof, polydioxanone and its copolymers, polyhydroxyalkanoates, polypropylene fumarate), polyoxymethylene, poloxamers, poly(ortho)esters, poly(butyric acid), poly(valeric acid), poly(lactide-co-caprolactone), and trimethylene carbonate, polyvinylpyrrolidone.

The molecular weight of a polymer may vary. In some embodiments, the molecular weight may be at least about 0.5 kDa, at least about 1 kDa, at least about 2 kDa, at least about 3 kDa, at least about 4 kDa, at least about 5 kDa, at least about 6 kDa, at least about 8 kDa, at least about 10 kDa, at least about 12 kDa, at least about 15 kDa, at least about 20 kDa, at least about 30 kDa, at least about 40 kDa, or at least about 50 kDa. In some embodiments, the molecular weight may be less than or equal to about 50 kDa, less than or equal to about 40 kDa, less than or equal to about 30 kDa, less than or equal to about 20 kDa, less than or equal to about 12 kDa, less than or equal to about 10 kDa, less than or equal to about 8 kDa, less than or equal to about 6 kDa, less than or equal to about 5 kDa, or less than or equal to about 4 kDa. Combinations of the above-referenced ranges are possible (e.g., a molecular weight of at least about 2 kDa and less than or equal to about 15 kDa). Other ranges are also possible. The molecular weight may be determined using any known technique such as light-scattering and gel permeation chromatography. Other methods are known in the art.

In certain embodiments, the polymer is biocompatible, i.e., the polymer does not typically induce an adverse response when inserted or injected into a living subject; for example, it does not include significant inflammation and/or acute rejection of the polymer by the immune system, for instance, via a T-cell-mediated response. It will be recognized, of course, that "biocompatibility" is a relative term, and some degree of immune response is to be expected even for polymers that are highly compatible with living tissue. However, as used herein, "biocompatibility" refers to the acute rejection of material by at least a portion of the immune system, i.e., a non-biocompatible material implanted into a subject provokes an immune response in the subject that is severe enough such that the rejection of the material by the immune system cannot be adequately controlled, and often is of a degree such that the material must be removed from the subject. One simple test to determine biocompatibility is to expose a polymer to cells in vitro; biocompatible polymers are polymers that typically does not result in significant cell death at moderate concentrations, e.g., at concentrations of about 50 micrograms/$10^6$ cells. For instance, a biocompatible polymer may cause less than about 20% cell death when exposed to cells such as fibroblasts or epithelial cells, even if phagocytosed or otherwise uptaken by such cells. In some embodiments, a substance is "biocompatible" if its addition to cells in vitro results in less than or equal to 20% cell death, and their administration in vivo does not induce unwanted inflammation or other such adverse effects.

In certain embodiments, a biocompatible polymer may be biodegradable, i.e., the polymer is able to degrade, chemically and/or biologically (e.g., by the cellular machinery or by hydrolysis), within a physiological environment, such as within the body or when introduced to cells. For instance, the polymer may be one that hydrolyzes spontaneously upon exposure to water (e.g., within a subject), and/or the polymer may degrade upon exposure to heat (e.g., at temperatures of about 37° C.). Degradation of a polymer may occur at varying rates, depending on the polymer or copolymer used. For example, the half-life of the polymer (the time at which 50% of the polymer is degraded into monomers and/or other nonpolymeric moieties) may be on the order of days, weeks, months, or years, depending on the polymer. The polymer may be biologically degraded, e.g., by enzymatic activity or cellular machinery, in some cases, for example, through exposure to a lysozyme (e.g., having relatively low pH). In some cases, the polymer may be broken down into monomers and/or other nonpolymeric moieties that cells can either reuse or dispose of without significant toxic effect on the cells (i.e., fewer than about 20% of the cells are killed when the components are added to cells in vitro). For example, polylactide may be hydrolyzed to form lactic acid, polyglycolide may be hydrolyzed to form glycolic acid, etc.).

Examples of biodegradable polymers include, but are not limited to, poly(ethylene glycol)-poly(propylene oxide)- poly(ethylene glycol) triblock copolymers, poly(lactide) (or poly(lactic acid)), poly(glycolide) (or poly(glycolic acid)), poly(orthoesters), poly(caprolactones), polylysine, poly(ethylene imine), poly(acrylic acid), poly(urethanes), poly(anhydrides), poly(esters), poly(trimethylene carbonate), poly (ethyleneimine), poly(acrylic acid), poly(urethane), poly (beta amino esters) or the like, and copolymers or derivatives of these and/or other polymers, for example, poly(lactide-co-glycolide) (PLGA).

In certain embodiments, a polymer may biodegrade within a period that is acceptable in the desired application. In certain embodiments, such as in vivo therapy, such degradation occurs in a period usually less than about five years, one year, six months, three months, one month, fifteen days, five days, three days, or even one day or less (e.g., 1-4 hours, 4-8 hours, 4-24 hours, 1-24 hours) on exposure to a physiological solution with a pH between 6 and 8 having a temperature of between 25 and 37° C. In other embodiments, the polymer degrades in a period of between about one hour and several weeks, depending on the desired application.

Although coatings and particles described herein may include polymers, in some embodiments, the particles described herein comprise a hydrophobic material that is not a polymer (e.g., a non-polymer) and is not a pharmaceutical agent. For example, all or portions of a particle may be coated with a passivating layer in some embodiments. Non-limiting examples of non-polymeric materials may include certain metals, waxes, and organic materials (e.g., organic silanes, perfluorinated or fluorinated organic materials).

Particles with Reduced Mucoadhesion

As described herein, in some embodiments, a method involves identifying a material such as a particle to which it is desired that its mucoadhesiveness be reduced. Materials in need of increased diffusivity through mucus may be, for example, hydrophobic, have many hydrogen bond donors or acceptors, and/or may be highly charged. In some cases, the material may include a crystalline or amorphous solid material. The material, which may serve as a core, may be coated with a suitable polymer described herein, thereby forming a particle with a plurality of surface-altering moieties on the surface, resulting in reduced mucoadhesion. Particles herein described as having reduced mucoadhesion may alternatively be characterized as having increased transport through mucus, being mobile in mucus, or mucus-penetrating (i.e., mucus-penetrating particles), meaning that the particles are transported through mucus faster than a (negative) control particle. The (negative) control particle may be a particle that is known to be mucoadhesive, e.g., an unmodified particle or core that is not coated with a coating described herein, such as a 200 nm carboxylated polystyrene particle.

In certain embodiments, methods herein include preparing a pharmaceutical composition or formulation of the modified substance, e.g., in a formulation adapted for delivery (e.g., topical delivery) to mucus or a mucosal surface of a subject. The pharmaceutical composition with surface-altering moieties may be delivered to the mucosal surface of a subject, may pass through the mucosal barrier in the subject, and/or prolonged retention and/or increased uniform distribution of the particles at mucosal surfaces, e.g., due to reduced mucoadhesion. As will be known by those of ordinary skill in the art, mucus is a viscoelastic and adhesive substance that traps most foreign particles. Trapped particles are not able to reach the underlying epithelium and/or are quickly eliminated by mucus clearance mechanisms. For a particle to reach the underlying epithelium and/or for a particle to have prolonged retention in the mucosal tissue, the particle must quickly penetrate mucus secretions and/or avoid the mucus clearance mechanisms. If a particle does not adhere substantially to the mucus, the particle may be able to diffuse in the interstitial fluids between mucin fibers and reach the underlying epithelium and/or not be eliminated by the mucus clearance mechanisms. Accordingly, modifying mucoadhesive materials, (e.g., pharmaceutical agents that are hydrophobic) with a material to reduce the mucoadhesion of the particle may allow for efficient delivery of the particles to the underlying epithelium and/or prolonged retention at mucosal surfaces.

Furthermore, in some embodiments, the particles described herein having reduced mucoadhesion facilitate better distribution of the particles at a tissue surface, and/or have a prolonged presence at the tissue surface, compared to particles that are more mucoadhesive. For example, in some cases a luminal space such as the gastrointestinal tract is surrounded by a mucus-coated surface. Mucoadhesive particles delivered to such a space are typically removed from the luminal space and from the mucus-coated surface by the body's natural clearance mechanisms. The particles described herein with reduced mucoadhesion may remain in the luminal space for relatively longer periods compared to the mucoadhesive particles. This prolonged presence may prevent or reduce clearance of the particles, and/or may allow for better distribution of the particles on the tissue surface. The prolonged presence may also affect the particle transport through the luminal space, e.g., the particles may distribute into the mucus layer and may reach the underlying epithelium.

In certain embodiments, a material (e.g., a core) coated with a polymer described herein may pass through mucus or a mucosal barrier in a subject, and/or exhibit prolonged retention and/or increase uniform distribution of the particles at mucosal surfaces, e.g., such substances are cleared more slowly (e.g., at least 2 times, 5 times, 10 times, or even at least 20 times more slowly) from a subject's body as compared to a (negative) control particle. The (negative) control particle may be a particle that is known to be mucoadhesive, e.g., an unmodified particle or core that is not coated with a coating described herein, such as a 200 nm carboxylated polystyrene particle.

In certain embodiments, a particle described herein has certain a relative velocity, $<V_{mean}>_{rel}$, which is defined as follows:

$$<V_{mean}>_{rel} = \frac{<V_{mean}>_{Sample} - <V_{mean}>_{Negative\ control}}{<V_{mean}>_{Positive\ control} - <V_{mean}>_{Negative\ control}} \quad \text{(Equation 1)}$$

where $<V_{mean}>$ is the ensemble average trajectory-mean velocity, $V_{mean}$ is the velocity of an individual particle averaged over its trajectory, the sample is the particle of interest, the negative control is a 200 nm carboxylated polystyrene particle, and the positive control is a 200 nm polystyrene particle densely PEGylated with 2 kDa-5 kDa PEG.

The relative velocity can be measured by a multiple particle tracking technique. For instance, a fluorescent microscope equipped with a CCD camera can be used to capture 15 s movies at a temporal resolution of 66.7 ms (15 frames/s) under 100× magnification from several areas within each sample for each type of particles: sample, negative control, and positive control. The sample, negative and positive controls may be fluorescent particles to observe tracking. Alternatively non-fluorescent particles may be coated with a fluorescent molecule, a fluorescently tagged surface agent or a fluorescently tagged polymer. An advanced image processing software (e.g., Image Pro or MetaMorph) can be used to measure individual trajectories of multiple particles over a time-scale of at least 3.335 s (50 frames).

In some embodiments, a particle described herein has a relative velocity of greater than about 0.3, greater than about 0.4, greater than about 0.5, greater than about 0.6, greater than about 0.7, greater than about 0.8, greater than about 0.9, greater than about 1.0, greater than about 1.1, greater than about 1.2, greater than about 1.3, greater than about 1.4, greater than about 1.5, greater than about 1.6, greater than about 1.7, greater than about 1.8, greater than about 1.9 or greater than about 2.0 in mucus. In some embodiments, a particle described herein has a relative velocity of less than or equal to about 10.0, less than or equal to about 8.0, less than or equal to about 6.0, less than or equal to about 4.0, less than or equal to about 3.0, less than or equal to about 2.0, less than or equal to about 1.9, less than or equal to about 1.8, less than or equal to about 1.7, less than or equal to about 1.6, less than or equal to about 1.5, less than or equal to about 1.4, less than or equal to about 1.3, less than or equal to about 1.2, less than or equal to about 1.1, less than or equal to about 1.0, less than or equal to about 0.9, less than or equal to about 0.8, or less than or equal to about 1.7 in mucus. Combinations of the above-noted ranges are possible (e.g., a relative velocity of greater than about 0.5 and less than or equal to about 6.0). Other ranges are also possible. The mucus may be, for example, human cervicovaginal mucus.

In certain embodiments, a particle described herein can diffuse through mucus or a mucosal barrier at a greater rate or diffusivity than a control particle or a corresponding particle (e.g., a corresponding particle that is unmodified and/or is not coated with a coating described herein). In some cases, a particle described herein may pass through mucus or a mucosal barrier at a rate of diffusivity that is at least about 10 times, 20 times, 30 times, 50 times, 100 times, 200 times, 500 times, 1000 times, 2000 times, 5000 times, 10000 times, or more, higher than a control particle or a corresponding particle. In some cases, a particle described herein may pass through mucus or a mucosal barrier at a rate of diffusivity that is less than or equal to about 10000 times higher, less than or equal to about 5000 times higher, less than or equal to about 2000 times higher, less than or equal to about 1000 times higher, less than or equal to about 500 times higher, less than or equal to about 200 times higher, less than or equal to about 100 times higher, less than or equal to about 50 times higher, less than or equal to about 30 times higher, less than or equal to about 20 times higher, or less than or equal to about 10 times higher than a control particle or a corresponding particle. Combinations of the above-referenced ranges are also possible (e.g., at least about 10 times and less than or equal to about 1000 times higher than a control particle or a corresponding particle). Other ranges are also possible.

For the purposes of the comparisons described herein, the corresponding particle may be approximately the same size, shape, and/or density as the test particle but lacking the coating that makes the test particle mobile in mucus. In some cases, the measurement is based on a time scale of about 1 second, or about 0.5 second, or about 2 seconds, or about 5 seconds, or about 10 seconds. Those of ordinary skill in the art will be aware of methods for determining the geometric mean square displacement and rate of diffusivity.

In addition, a particle described herein may pass through mucus or a mucosal barrier with a geometric mean squared displacement that is at least about 10 times, 20 times, 30 times, 50 times, 100 times, 200 times, 500 times, 1000 times, 2000 times, 5000 times, 10000 times, or more, higher than a corresponding particle or control particle. In some cases, a particle described herein may pass through mucus or a mucosal barrier with a geometric mean squared displacement that is less than or equal to about 10000 times higher, less than or equal to about 5000 times higher, less than or equal to about 2000 times higher, less than or equal to about 1000 times higher, less than or equal to about 500 times higher, less than or equal to about 200 times higher, less than or equal to about 100 times higher, less than or equal to about 50 times higher, less than or equal to about 30 times higher, less than or equal to about 20 times higher, or less than or equal to about 10 times higher than a control particle or a corresponding particle. Combinations of the above-referenced ranges are also possible (e.g., at least about 10 times and less than or equal to about 1000 times higher than a control particle or a corresponding particle). Other ranges are also possible.

In some embodiments, a particle described herein diffuses through a mucosal barrier at a rate approaching the rate or diffusivity at which said particles can diffuse through water. In some cases, a particle described herein may pass through a mucosal barrier at a rate or diffusivity that is less than or equal to about $\frac{1}{2}$, less than or equal to about $\frac{1}{4}$, less than or equal to about $\frac{1}{8}$, less than or equal to about $\frac{1}{16}$, less than or equal to about $\frac{1}{32}$, less than or equal to about $\frac{1}{50}$, less than or equal to about $\frac{1}{100}$, less than or equal to about $\frac{1}{200}$, less than or equal to about $\frac{1}{300}$, less than or equal to about $\frac{1}{400}$, less than or equal to about $\frac{1}{500}$, less than or equal to about $\frac{1}{600}$, less than or equal to about $\frac{1}{700}$, less than or equal to about $\frac{1}{800}$, less than or equal to about $\frac{1}{900}$, less than or equal to about $\frac{1}{1000}$, less than or equal to about $\frac{1}{2000}$, less than or equal to about $\frac{1}{5000}$, less than or equal to about $\frac{1}{10,000}$ the diffusivity that the particle diffuse through water under identical conditions. In some cases, a particle described herein may pass through a mucosal barrier at a rate or diffusivity that is greater than about $\frac{1}{10,000}$, greater than about $\frac{1}{5000}$, greater than about $\frac{1}{2000}$, greater than about $\frac{1}{1000}$, greater than about $\frac{1}{900}$, greater than about $\frac{1}{800}$, greater than about $\frac{1}{700}$, greater than about $\frac{1}{600}$, greater than about $\frac{1}{500}$, greater than about $\frac{1}{400}$, greater than about $\frac{1}{300}$, greater than about $\frac{1}{200}$, greater than about $\frac{1}{100}$, greater than about $\frac{1}{50}$, greater than about $\frac{1}{32}$, greater than about $\frac{1}{16}$, greater than about $\frac{1}{8}$, greater than about $\frac{1}{4}$, or greater than about $\frac{1}{2}$ the diffusivity that the particle diffuse through water under identical conditions. Combinations of the above-referenced ranges are also possible (e.g., greater than about $\frac{1}{5000}$ and less than $\frac{1}{500}$ the diffusivity that the particle diffuse through water under identical conditions). Other ranges are also possible. The measurement may be based on a time scale of about 1 second, or about 0.5 second, or about 2 seconds, or about 5 seconds, or about 10 seconds.

In a particular embodiment, a particle described herein may diffuse through human cervicovaginal mucus at a diffusivity that is less than about $\frac{1}{500}$ the diffusivity that the particle diffuses through water. In some cases, the measurement is based on a time scale of about 1 second, or about 0.5 second, or about 2 seconds, or about 5 seconds, or about 10 seconds.

In certain embodiments, the present invention provides particles that travel through mucus, such as human cervicovaginal mucus, at certain absolute diffusivities. For example, the particles of described herein may travel at diffusivities of at least about $1\times10^{-4}$ µm/s, $2\times10^{-4}$ µm/s, $5\times10^{-4}$ µm/s, $1\times10^{-3}$ µm/s, $2\times10^{-3}$ µm/s, $5\times10^{-3}$ µm/s, $1\times10^{-2}$ µm/s, $2\times10^{-2}$ µm/s, $4\times10^{-2}$ µm/s, $5\times10^{-2}$ µm/s, $6\times10^{-2}$ µm/s, $8\times10^{-2}$ µm/s, $1\times10^{-1}$ µm/s, $2\times10^{-1}$ µm/s, $5\times10^{-1}$ µm/s, 1 µm/s, or 2 µm/s. In some cases, the particles may travel at diffusivities of less than or equal to about 2 µm/s, less than or equal to about 1 µm/s, less than or equal to about $5\times10^{-1}$ µm/s, less than or equal to about $2\times10^{-1}$ µm/s, less than or equal to about $1\times10^{-1}$ µm/s, less than or equal to about $8\times10^{-2}$ µm/s, less than or equal to about $6\times10^{-2}$ µm/s, less than or equal to about $5\times10^{-2}$ µm/s, less than or equal to about $4\times10^{-2}$ µm/s, less than or equal to about $2\times10^{-2}$ µm/s, less than or equal to about $1\times10^{-2}$ µm/s, less than or equal to about $5\times10^{-3}$ µm/s, less than or equal to about $2\times10^{-3}$ µm/s, less than or equal to about $1\times10^{-3}$ µm/s, less than or equal to about $5\times10^{-4}$ µm/s, less than or equal to about $2\times10^{-4}$ µm/s, or less than or equal to about $1\times10^{-4}$ µm/s. Combinations of the above-referenced ranges are also possible (e.g., greater than about $2\times10^{-4}$ µm/s and less than or equal to about $1\times10^{-1}$ µm/s). Other ranges are also possible. In some cases, the measurement is based on a time scale of about 1 second, or about 0.5 second, or about 2 seconds, or about 5 seconds, or about 10 seconds.

It should be appreciated that while many of the mobilities (e.g., relative velocities, diffusivities) described here may be measured in human cervicovaginal mucus, they may be measured in other types of mucus as well.

In certain embodiments, a particle described herein comprises surface-altering moieties at a given density. The surface-altering moieties may be the portions of a surface-altering agent that are, for example, exposed to the solvent containing the particle. As an example, the PEG segments may be surface-altering moieties of the surface-altering agent PEG-PPO-PEG. In some cases, the surface-altering moieties and/or surface-altering agents are present at a density of at least about 0.001 units or molecules per $nm^2$, at least about 0.002, at least about 0.005, at least about 0.01, at least about 0.02, at least about 0.05, at least about 0.1, at least about 0.2, at least about 0.5, at least about 1, at least about 2, at least about 5, at least about 10, at least about 20, at least about 50, at least about 100 units or molecules per $nm^2$, or more units or molecules per $nm^2$. In some cases, the surface-altering moieties and/or surface-altering agents are present at a density of less than or equal to about 100 units or molecules per $nm^2$, less than or equal to about 50, less than or equal to about 20, less than or equal to about 10, less than or equal to about 5, less than or equal to about 2, less than or equal to about 1, less than or equal to about 0.5, less than or equal to about 0.2, less than or equal to about 0.1, less than or equal to about 0.05, less than or equal to about 0.02, or less than or equal to about 0.01 units or molecules per $nm^2$. Combinations of the above-referenced ranges are possible (e.g., a density of at least about 0.01 and less than or equal to about 1 units or molecules per $nm^2$). Other ranges are also possible.

Those of ordinary skill in the art will be aware of methods to estimate the average density of surface-altering moieties (see, for example, S. J. Budijono et al., Colloids and Surfaces A: Physicochem. Eng. Aspects 360 (2010) 105-110; Joshi, et al. Anal. Chim. Acta 104 (1979) 153-160, each of which is incorporated herein by reference). For example, as described herein, the average density of surface-altering moieties can be determined using HPLC quantitation and DLS analysis. A suspension of particles for which surface density determination is of interest is first sized using DLS: a small volume is diluted to an appropriate concentration (~100 µg/mL, for example), and the z-average diameter is taken as a representative measurement of particle size. The remaining suspension is then divided into two aliquots. Using HPLC, the first aliquot is assayed for the total concentration of core material and for the total concentration of surface-altering moiety. Again using HPLC the second aliquot is assayed for the concentration of free or unbound surface-altering moiety. In order to get only the free or unbound surface-altering moiety from the second aliquot, the particles, and therefore any bound surface-altering moiety, are removed by ultracentrifugation. By subtracting the concentration of the unbound surface-altering moiety from the total concentration of surface-altering moiety, the concentration of bound surface-altering moiety can be determined. Since the total concentration of core material was also determined from the first aliquot, the mass ratio between the core material and the surface-altering moiety can be determined. Using the molecular weight of the surface-altering moiety the number of surface-altering moiety to mass of core material can be calculated. To turn this number into a surface density measurement, the surface area per mass of core material needs to be calculated. The volume of the particle is approximated as that of a sphere with the diameter obtained from DLS allowing for the calculation of the surface area per mass of core material. In this way the number of surface-altering moieties per surface area can be determined.

Density may also be measured by quantifying or estimating the core material surface area by methods such as electron microscopy, light scattering, or surface interaction measurements and then quantifying the adhered surface agent(s) by methods such as liquid chromatography or mass spectrometry. (See, for example, Wang et al., Angew Chem Int Ed Engl, 2008, 47(50), 9726-9, which is incorporated herein by reference).

In certain embodiments, the particles described herein comprise surface-altering moieties and/or agents that affect the zeta-potential of the particle. The zeta potential of the coated particle may be, for example, at least about −100 mV, at least about −75 mV, at least about −50 mV, at least about −40 mV, at least about −30 mV, at least about −20 mV, at least about −10 mV, at least about −5 mV, at least about 5 mV, at least about 10 mV, at least about 20 mV, at least about 30 mV, at least about 40 mV, at least about 50 mV, at least about 75 mV, or at least about 100 mV. Combinations of the above-referenced ranges are possible (e.g., a zeta-potential of at least about −50 mV and less than or equal to about 50 mV). Other ranges are also possible.

The coated particles described herein may have any suitable shape and/or size. In some embodiments, a coated particle has a shape substantially similar to the shape of the core. In some cases, a coated particle described herein may be a nanoparticle, i.e., the particle has a characteristic dimension of less than about 1 micrometer, where the characteristic dimension of the particle is the diameter of a perfect sphere having the same volume as the particle. In other embodiments, larger sizes are possible (e.g., about 1-10 microns). A plurality of particles, in some embodiments, may also be characterized by an average size (e.g., an average largest cross-sectional dimension, or an average smallest cross-sectional dimension for the plurality of particles). A plurality of particles may have an average size of, for example, less than or equal to about 10 µm, less than or equal to about 5 µm, less than or equal to about 1 µm, less than or equal to about 800 nm, less than or equal to about 700 nm, less than or equal to 400 nm, less than or equal to 300 nm, less than or equal to about 200 nm, less than or equal to about 100 nm, less than or equal to about 75 nm, less than or equal to about 50 nm, less than or equal to about 40 nm, less than or equal to about 35 nm, less than or equal to about 30 nm, less than or equal to about 25 nm, less than or equal to about 20 nm, less than or equal to about 15 nm, or less than or equal to about 5 nm. In some cases, a plurality of particles may have an average size of, for example, at least about 5 nm, at least about 20 nm, at least about 50 nm, at least about 100 nm, at least about 200 nm, at least about 300 nm, at least about 400 nm, at least about 500 nm, at least about 1 µm, at least or at least about 5 µm. Combinations of the above-referenced ranges are also possible (e.g., an average size of at least about 50 nm and less than about 500 nm). Other ranges are also possible. In some embodiments, the sizes of the cores formed by a process described herein have a Gaussian-type distribution.

Pharmaceutical Agents

In some embodiments, a coated particle comprises at least one pharmaceutical agent. The pharmaceutical agent may be present in the core of the particle and/or present in a coating of the particle (e.g., dispersed throughout the core and/or coating). In some cases, a pharmaceutical agent may be disposed on the surface of the particle (e.g., on an outer surface of a coating, the inner surface of a coating, on a surface of the core). The pharmaceutical agent may be contained within a particle and/or disposed in a portion of the particle using commonly known techniques (e.g., by coating, adsorption, covalent linkage, or other process). In some cases, the pharmaceutical agent may be present in the core of the particle prior to or during coating of the particle. In some cases, the pharmaceutical agent is present during the formation of the core of the particle, as described herein.

Non-limiting examples of pharmaceutical agents include imaging agents, diagnostic agents, therapeutic agents, agents with a detectable label, nucleic acids, nucleic acid analogs, small molecules, peptidomimetics, proteins, peptides, lipids, vaccines, viral vectors, virus, and surfactants.

In some embodiments, a pharmaceutical agent contained in a particle described herein has a therapeutic, diagnostic, or imaging effect in a mucosal tissue to be targeted. Non-limiting examples of mucosal tissues include oral (e.g., including the buccal and esophagal membranes and tonsil surface), ophthalmic, gastrointestinal (e.g., including stomach, small intestine, large intestine, colon, rectum), nasal, respiratory (e.g., including nasal, pharyngeal, tracheal and bronchial membranes), and genital (e.g., including vaginal, cervical and urethral membranes) tissues.

Any suitable number of pharmaceutical agents may be present in a particle described herein. For example, at least 1, at least 2, at least 3, at least 4, at least 5, or more, but generally less than 10, pharmaceutical agents may be present in a particle described herein.

A number of drugs that are mucoadhesive are known in the art and may be used as pharmaceutical agents in the particles described herein (see, for example, Khanvilkar K, et al. Adv Drug Del Rev 48:173-193, 2001; Bhat P G et al. J Pharm Sci 85:624-30, 1996). Additional non-limiting examples of pharmaceutical agents include imaging and diagnostic agents (such as radioopaque agents, labeled antibodies, labeled nucleic acid probes, dyes, such as colored or fluorescent dyes, etc.) and adjuvants (radiosensitizers, transfection-enhancing agents, chemotactic agents and chemoattractants, peptides that modulate cell adhesion and/or cell mobility, cell permeabilizing agents, vaccine potentiators, inhibitors of multidrug resistance and/or efflux pumps, etc.).

Additional non-limiting examples of pharmaceutical agents include aloxiprin, auranofin, azapropazone, benorylate, diflunisal, etodolac, fenbufen, fenoprofen calcim, flurbiprofen, furosemide, ibuprofen, indomethacin, ketoprofen, loteprednol etabonate, meclofenamic acid, mefenamic acid, nabumetone, naproxen, oxyphenbutazone, phenylbutazone, piroxicam, sulindac, albendazole, bephenium hydroxynaphthoate, cambendazole, dichlorophen, ivermectin, mebendazole, oxamniquine, oxfendazole, oxantel embonate, praziquantel, pyrantel embonate, thiabendazole, amiodarone HCl, disopyramide, flecainide acetate, quinidine sulphate. Anti-bacterial agents: benethamine penicillin, cinoxacin, ciprofloxacin HCl, clarithromycin, clofazimine, cloxacillin, demeclocycline, doxycycline, erythromycin, ethionamide, imipenem, nalidixic acid, nitrofurantoin, rifampicin, spiramycin, sulphabenzamide, sulphadoxine, sulphamerazine, sulphacetamide, sulphadiazine, sulphafurazole, sulphamethoxazole, sulphapyridine, tetracycline, trimethoprim, dicoumarol, dipyridamole, nicoumalone, phenindione, amoxapine, maprotiline HCl, mianserin HCL, nortriptyline HCl, trazodone HCL, trimipramine maleate, acetohexamide, chlorpropamide, glibenclamide, gliclazide, glipizide, tolazamide, tolbutamide, beclamide, carbamazepine, clonazepam, ethotoin, methoin, methsuximide, methylphenobarbitone, oxcarbazepine, paramethadione, phenacemide, phenobarbitone, phenytoin, phensuximide, primidone, sulthiame, valproic acid, amphotericin, butoconazole nitrate, clotrimazole, econazole nitrate, fluconazole, flucytosine, griseofulvin, itraconazole, ketoconazole, miconazole, natamycin, nystatin, sulconazole nitrate, terbinafine HCl, terconazole, tioconazole, undecenoic acid, allopurinol, probenecid, sulphin-pyrazone, amlodipine, benidipine, darodipine, dilitazem HCl, diazoxide, felodipine, guanabenz acetate, isradipine, minoxidil, nicardipine HCl, nifedipine, nimodipine, phenoxybenzamine HCl, prazosin HCL, reserpine, terazosin HCL, amodiaquine, chloroquine, chlorproguanil HCl, halofantrine HCl, mefloquine HCl, roguanil HCl, pyrimethamine, quinine sulphate, dihydroergotamine mesylate, ergotamine tartrate, methysergide maleate, pizotifen maleate, sumatriptan succinate, atropine, benzhexol HCl, biperiden, ethopropazine HCl, hyoscyamine, mepenzolate bromide, oxyphencylcimine HCl, tropicamide, aminoglutethimide, amsacrine, azathioprine, busulphan, chlorambucil, cyclosporin, dacarbazine, estramustine, etoposide, lomustine, melphalan, mercaptopurine, methotrexate, mitomycin, mitotane, mitozantrone, procarbazine HCl, tamoxifen citrate, testolactone, benznidazole, clioquinol, decoquinate, diiodohydroxyquinoline, diloxanide furoate, dinitolmide, furzolidone, metronidazole, nimorazole, nitrofurazone, ornidazole, tinidazole, carbimazole, propylthiouracil, alprazolam, amylobarbitone, barbitone, bentazepam, bromazepam, bromperidol, brotizolam, butobarbitone, carbromal, chlordiazepoxide, chlormethiazole, chlorpromazine, clobazam, clotiazepam, clozapine, diazepam, droperidol, ethinamate, flunanisone, flunitrazepam, fluopromazine, flupenthixol decanoate, fluphenazine decanoate, flurazepam, haloperidol, lorazepam, lormetazepam, medazepam, meprobamate, methaqualone, midazolam, nitrazepam, oxazepam, pentobarbitone, perphenazine pimozide, prochlorperazine, sulpiride, temazepam, thioridazine, triazolam, zopiclone, acebutolol, alprenolol, atenolol, labetalol, metoprolol, nadolol, oxprenolol, pindolol, propranolol, amrinone, digitoxin, digoxin, enoximone, lanatoside C, medigoxin, beclomethasone, betamethasone, budesonide, cortisone acetate, desoxymethasone, dexamethasone, fludrocortisone acetate, flunisolide, flucortolone, fluticasone propionate, hydrocortisone, methylprednisolone, prednisolone, prednisone, triamcinolone, acetazolamide, amiloride, bendrofluazide, bumetanide, chlorothiazide, chlorthalidone, ethacrynic acid, frusemide, metolazone, spironolactone, triamterene, bromocriptine mesylate, lysuride maleate, bisacodyl, cimetidine, cisapride, diphenoxylate HCl, domperidone, famotidine, loperamide, mesalazine, nizatidine, omeprazole, ondansetron HCL, ranitidine HCl, sulphasalazine, acrivastine, astemizole, cinnarizine, cyclizine, cyproheptadie HCl, dimenhydrinate, flunarizine HCl, loratadine, meclozine HCl, oxatomide, terfenadine, bezafibrate, clofibrate, fenofibrate, gemfibrozil, probucol, amyl nitrate, glyceryl trinitrate, isosorbide dinitrate, isosorbide mononitrate, pentaerythritol tetranitrate, betacarotene, vitamin A, vitamin B 2, vitamin D, vitamin E, vitamin K, codeine, dextropropyoxyphene, diamorphine, dihydrocodeine, meptazinol, methadone, morphine, nalbuphine, pentazocine, clomiphene citrate, danazol, ethinyl estradiol, medroxyprogesterone acetate, mestranol, methyltestosterone, norethisterone, norgestrel, estradiol, conjugated oestrogens, progesterone, stanozolol, stibestrol, testosterone, tibolone, amphetamine, dexamphetamine, dexfenfluramine, fenfluramine, and mazindol.

Uses and Pharmaceutical Compositions

The particles described herein may be employed in any suitable application. In some cases, the particles are part of pharmaceutical compositions (e.g., as described herein), for example, those used to deliver a pharmaceutical agent (e.g., a drug, therapeutic agent, diagnostic agent, imaging agent) through or to mucus or a mucosal surface. A pharmaceutical composition may comprise at least one particle described herein and one or more pharmaceutically acceptable excipients or carriers. The composition may be used in treating, preventing, and/or diagnosing a condition in a subject, wherein the method comprises administering to a subject the pharmaceutical composition. A subject or patient to be treated by the articles and methods described herein may mean either a human or non-human animal, such as primates, mammals, and vertebrates.

Methods involving treating a subject may include preventing a disease, disorder or condition from occurring in the subject which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected (e.g., such treating the pain of a subject by administration of an analgesic agent even though such agent does not treat the cause of the pain).

In some embodiments, a pharmaceutical composition described herein is delivered to a mucosal surface in a subject and may pass through a mucosal barrier in the subject (e.g., mucus), and/or may exhibit prolonged retention and/or increased uniform distribution of the particles at mucosal surfaces, e.g., due to reduced mucoadhesion. Non-limiting examples of mucosal tissues include oral (e.g., including the buccal and esophageal membranes and tonsil surface), ophthalmic, gastrointestinal (e.g., including stomach, small intestine, large intestine, colon, rectum), nasal, respiratory (e.g., including nasal, pharyngeal, tracheal and bronchial membranes), genital (e.g., including vaginal, cervical and urethral membranes).

Pharmaceutical compositions described herein and for use in accordance with the articles and methods described herein may include a pharmaceutically acceptable excipient or carrier. A pharmaceutically acceptable excipient or pharmaceutically acceptable carrier may include a non-toxic, inert solid, semi-solid or liquid filler, diluent, encapsulating material or formulation auxiliary of any suitable type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. As would be appreciated by one of skill in this art, the excipients may be chosen based on the route of administration as described below, the pharmaceutical agent being delivered, time course of delivery of the agent, etc.

Pharmaceutical compositions containing the particles described herein may be administered to a subject via any route known in the art. These include, but are not limited to, oral, sublingual, nasal, intradermal, subcutaneous, intramuscular, rectal, vaginal, intravenous, intraarterial, intracisternally, intraperitoneal, intravitreal, periocular, topical (as by powders, creams, ointments, or drops), bucal and inhalational administration. In some embodiments, compositions described herein may be administered parenterally as injections (intravenous, intramuscular, or subcutaneous), drop infusion preparations, or suppositories. As would be appreciated by one of skill in this art, the route of administration and the effective dosage to achieve the desired biological effect may be determined by the agent being administered, the target organ, the preparation being administered, time course of administration, disease being treated, intended use, etc.

As an example, the particles may be included in a pharmaceutical composition to be formulated as a nasal spray, such that the pharmaceutical composition is delivered across a nasal mucus layer. As another example, the particles may be included in a pharmaceutical composition to be formulated as an inhaler, such that the pharmaceutical compositions is delivered across a pulmonary mucus layer. As another example, if compositions are to be administered orally, it may be formulated as tablets, capsules, granules, powders, or syrups. Similarly, the particles may be included in a pharmaceutical composition that is to be delivered via ophthalmic, gastrointestinal, nasal, respiratory, rectal, urethral and/or vaginal tissues.

For application by the ophthalmic mucous membrane route, subject compositions may be formulated as eye drops or eye ointments. These formulations may be prepared by conventional means, and, if desired, the subject compositions may be mixed with any conventional additive, such as buffering or pH-adjusting agents, tonicity adjusting agents, viscosity modifiers, suspension stabilizers, preservatives, and other pharmaceutical excipients. In addition, in certain embodiments, subject compositions described herein may be lyophilized or subjected to another appropriate drying technique such as spray drying.

In some embodiments, particles described herein that may be administered in inhalant or aerosol formulations comprise one or more pharmaceutical agents, such as adjuvants, diagnostic agents, imaging agents, or therapeutic agents useful in inhalation therapy. The particle size of the particulate medicament should be such as to permit inhalation of substantially all of the medicament into the lungs upon administration of the aerosol formulation and may be, for example, less than about 20 microns, e.g., in the range of about 1 to about 10 microns, e.g., about 1 to about 5 microns, although other ranges are also possible. The particle size of the medicament may be reduced by conventional means, for example by milling or micronisation. Alternatively, the particulate medicament can be administered to the lungs via nebulization of a suspension. The final aerosol formulation may contain, for example, between 0.005-90% w/w, between 0.005-50%, between 0.005-10%, between about 0.005-5% w/w, or between 0.01-1.0% w/w, of medicament relative to the total weight of the formulation. Other ranges are also possible.

It is desirable, but by no means required, that the formulations described herein contain no components which may provoke the degradation of stratospheric ozone. In particular, in some embodiments, propellants are selected that do not contain or do not consist essentially of chlorofluorocarbons such as $CCl_3F$, $CCl_2F_2$, and $CF_3CCl_3$.

The aerosol may comprise propellant. The propellant may optionally contain an adjuvant having a higher polarity and/or a higher boiling point than the propellant. Polar adjuvants which may be used include (e.g., $C_{2-6}$) aliphatic alcohols and polyols such as ethanol, isopropanol, and propylene glycol, preferably ethanol. In general, only small quantities of polar adjuvants (e.g., 0.05-3.0% w/w) may be required to improve the stability of the dispersion-the use of quantities in excess of 5% w/w may tend to dissolve the medicament. Formulations in accordance with the embodiments described herein may contain less than 1% w/w, e.g., about 0.1% w/w, of polar adjuvant. However, the formulations described herein may be substantially free of polar adjuvants, especially ethanol. Suitable volatile adjuvants include saturated hydrocarbons such as propane, n-butane, isobutane, pentane and isopentane and alkyl ethers such as dimethyl ether. In general, up to 50% w/w of the propellant may comprise a volatile adjuvant, for example 1 to 30% w/w of a volatile saturated $C_1$-$C_6$ hydrocarbon. Optionally, the aerosol formulations according to the invention may further comprise one or more surfactants. The surfactants can be physiologically acceptable upon administration by inhalation. Within this category are included surfactants such as L-α-phosphatidylcholine (PC), 1,2-dipalmitoylphosphatidycholine (DPPC), oleic acid, sorbitan trioleate, sorbitan mono-oleate, sorbitan monolaurate, polyoxyethylene sorbitan monolaurate, polyoxyethylene sorbitan monooleate, natural lecithin, oleyl polyoxyethylene ether, stearyl polyoxyethylene ether, lauryl polyoxyethylene ether, block copolymers of oxyethylene and oxypropylene, synthetic lecithin, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, polyethylene glycol 400, cetyl pyridinium chloride, benzalkonium chloride, olive oil, glyceryl monolaurate, corn oil, cotton seed oil, and sunflower seed oil.

The formulations described herein may be prepared by dispersal of the particles in the selected propellant and/or co-propellant in an appropriate container, e.g., with the aid of sonication. The particles may be suspended in co-propellant and filled into a suitable container. The valve of the container is then sealed into place and the propellant introduced by pressure filling through the valve in the conventional manner. The particles may be thus suspended or dissolved in a liquefied propellant, sealed in a container with a metering valve and fitted into an actuator. Such metered dose inhalers are well known in the art. The metering valve may meter 10 to 500 μL and preferably 25 to 150 μL. In certain embodiments, dispersal may be achieved using dry powder inhalers (e.g., spinhaler) for the particles (which remain as dry powders). In other embodiments, nanospheres, may be suspended in an aqueous fluid and nebulized into fine droplets to be aerosolized into the lungs.

Sonic nebulizers may be used because they minimize exposing the agent to shear, which may result in degradation of the particles. Ordinarily, an aqueous aerosol is made by formulating an aqueous solution or suspension of the particles together with conventional pharmaceutically acceptable carriers and stabilizers/surface-altering agents. The carriers and stabilizers/surface-altering agents vary with the requirements of the particular composition, but typically include non-ionic surfactants (Tweens, Pluronic®, or polyethylene glycol), innocuous proteins like serum albumin, sorbitan esters, oleic acid, lecithin, amino acids such as glycine, buffers, salts, sugars, or sugar alcohols. Aerosols generally are prepared from isotonic solutions.

Liquid dosage forms for oral administration include pharmaceutically acceptable emulsions, microemulsions, solutions, suspensions, syrups, and elixirs. In addition to the active ingredients (i.e., microparticles, nanoparticles, liposomes, micelles, polynucleotide/lipid complexes), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In certain embodiments, the particles are suspended in a carrier fluid comprising 1% (w/v) sodium carboxymethyl cellulose and 0.1% (v/v) Tween 80.

The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration can be suppositories which can be prepared by mixing the particles with suitable non-irritating excipients or carriers such as cocoa butter, polyethylene glycol, or a suppository wax which are solid at ambient temperature but liquid at body temperature and therefore melt in the rectum or vaginal cavity and release the particles.

Solid dosage forms for oral administration include capsules, tablets, pills, powders, and granules. In such solid dosage forms, the particles are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

Dosage forms for topical or transdermal administration of an inventive pharmaceutical composition include ointments, pastes, creams, lotions, gels, powders, solutions, sprays, inhalants, or patches. The particles are admixed under sterile conditions with a pharmaceutically acceptable carrier and any needed preservatives or buffers as may be required. Ophthalmic formulation, ear drops, and eye drops are also contemplated as being within the scope of this invention.

The ointments, pastes, creams, and gels may contain, in addition to the particles described herein, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the particles described herein, excipients such as lactose, talc, silicic acid, aluminum hydroxide, calcium silicates, and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the microparticles or nanoparticles in a proper medium. Absorption enhancers can also be used to increase the flux of the compound across the skin. The rate can be controlled by either providing a rate controlling membrane or by dispersing the particles in a polymer matrix or gel.

The particles described herein comprising a pharmaceutical agent may be administered to a subject to be delivered in an amount sufficient to deliver to a subject a therapeutically effective amount of an incorporated pharmaceutical agent as part of a diagnostic, prophylactic, or therapeutic treatment. In general, an effective amount of a pharmaceutical agent or component refers to the amount necessary to elicit the desired biological response. The desired concentration of pharmaceutical agent in the particle will depend on numerous factors, including, but not limited to, absorption, inactivation, and excretion rates of the drug as well as the delivery rate of the compound from the subject compositions, the desired biological endpoint, the agent to be delivered, the target tissue, etc. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

The concentration and/or amount of any pharmaceutical agent to be administered to a subject may be readily determined by one of ordinary skill in the art. Known methods are also available to assay local tissue concentrations, diffusion rates from particles and local blood flow before and after administration of the therapeutic formulation.

The compositions and/or formulations described herein may have any suitable osmolarity. In some embodiments, a composition and/or formulation described herein may have an osmolarity of at least about 0 mOsm/L, at least about 5 mOsm/L, at least about 25 mOsm/L, at least about 50 mOsm/L, at least about 75 mOsm/L, at least about 100 mOsm/L, at least about 150 mOsm/L, at least about 200 mOsm/L, at least about 250 mOsm/L, or at least about 310 mOsm/L. In certain embodiments, a composition and/or formulation described herein may have an osmolarity of less than or equal to about 310 mOsm/L, less than or equal to about 250 mOsm/L, less than or equal to about 200 mOsm/L, less than or equal to about 150 mOsm/L, less than or equal to about 100 mOsm/L, less than or equal to about 75 mOsm/L, less than or equal to about 50 mOsm/L, less than or equal to about 25 mOsm/L, or less than or equal to about 5 mOsm/L. Combinations of the above-referenced ranges are also possible (e.g., an osmolarity of at least about 0 mOsm/L and less than or equal to about 50 mOsm/L). Other ranges are also possible. The osmolarity of the composition and/or formulation can be varied by changing, for example, the concentration of salts present in the solvent of the composition and/or formulation.

These and other aspects of the present invention will be further appreciated upon consideration of the following Examples, which are intended to illustrate certain particular embodiments of the invention but are not intended to limit its scope, as defined by the claims.

EXAMPLES

Example 1

The following describes a non-limiting example of a method of forming non-polymeric solid particles into mucus-penetrating particles. Pyrene, a hydrophobic naturally fluorescent compound, was used as the core particle and was prepared by a nanomilling process in the presence of various stabilizers. The stabilizers acted as surface-altering agents and formed coatings around the core particles. Different stabilizers/surface-altering agents were evaluated to determine effectiveness of the coated particles in penetrating mucus.

Pyrene was nanomilled in aqueous dispersions in the presence of various stabilizers/surface-altering agents to determine whether certain stabilizers/surface-altering agents can: 1) aid particle size reduction to several hundreds of nanometers and 2) physically (non-covalently) coat the surface of generated nanoparticles with a mucoinert coating that would minimize particle interactions with mucus constituents and prevent mucus adhesion. In these experiments, the stabilizers/surface-altering agents acted as a coating around the core particles, and the resulting particles were tested for their mobility in mucus, although in other embodiments, the stabilizers/surface-altering agents may be exchanged with other surface-altering agents that can increase mobility of the particles in mucus. The stabilizers/surface-altering agents tested included a variety of polymers, oligomers, and small molecules listed in Table2, including pharmaceutically relevant excipients such as poly(ethylene oxide)-poly(propylene oxide)-poly(ethylene oxide) block copolymers (Pluronics®), polyvinylpyrrolidones (Kollidon), and hydroxypropyl methylcellulose (Methocel), etc.

TABLE 2

Stabilizers/surface-altering agents tested with Pyrene as a model compound.

Polymeric Stabilizers/surface-altering agents

| Stabilizer | Acronym or Trade Name | Grade or Molecular Weight | Chemical Structure |
|---|---|---|---|
| Poly(ethylene oxide)-poly(propylene oxide)-poly(ethylene oxide) block copolymers | Pluronic ® | F127, F108, F68, F87, F38, P123, P105, P103, P65, L121, L101, L81, L44, L31 | 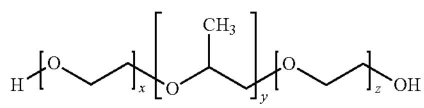 |
| Polyvinylpyrrolidone | PVP | Kollidon 17 (9K), Kollidon 25 (26K), Kollindon 30 (43K) | 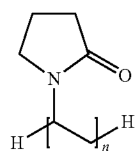 |
| PVA-poly(ethylene glycol) graft-copolymer | | Kollicoat IR | 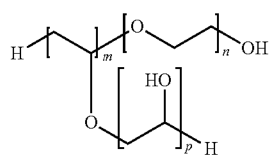 |
| Hydroxypropyl methylcellulose | HPMC | Methocel E50, Methocel K100 | 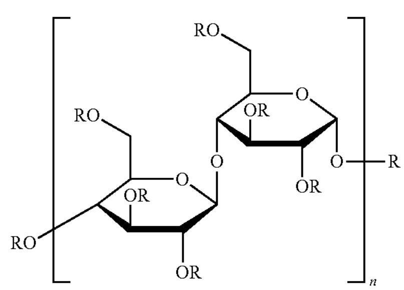 |

Oligomeric Stabilizers/surface-altering agents

Tween 20

$w + x + y + z = 20$

TABLE 2-continued
Stabilizers/surface-altering agents tested with Pyrene as a model compound.
Tween 80
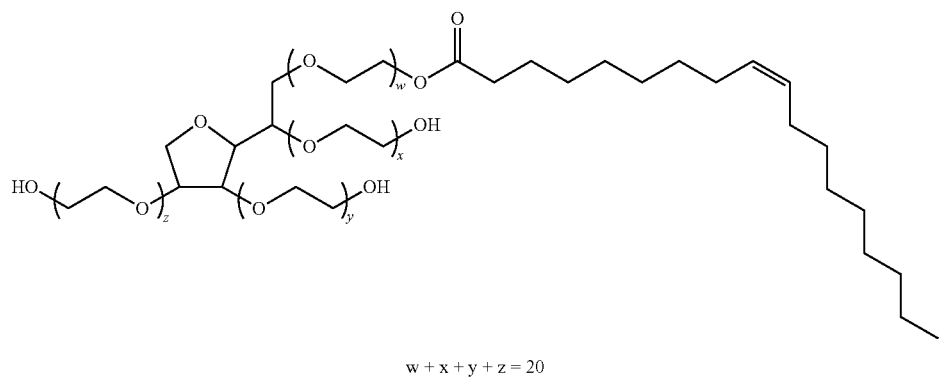
w + x + y + z = 20
Solutol HS 15
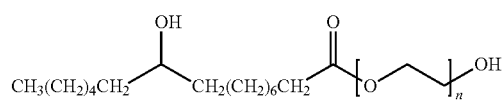
Triton X100
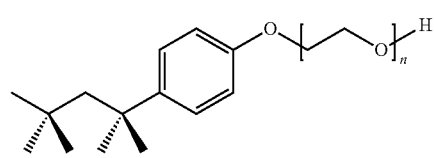
Tyloxapol
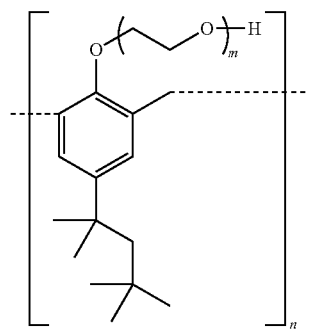
Cremophor RH 40
Small Molecule Stabilizers/surface-altering agents
Span 20
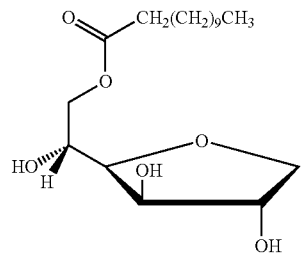
Span 80
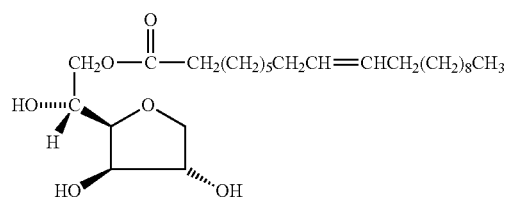

TABLE 2-continued

Stabilizers/surface-altering agents tested with Pyrene as a model compound.

Octyl glucoside

Cetytrimethylammonium bromide (CTAB)

Sodium dodecyl sulfate (SDS)

An aqueous dispersion containing pyrene and one of the stabilizers/surface-altering agents listed above was milled with milling media until particle size was reduced below 500 nm. Table 3 lists particle size characteristics of pyrene particles obtained by nanomilling in the presence of the various stabilizers/surface-altering agents. Particle size was measured by dynamic light scattering. When Pluronics® L101, L81, L44, L31, Span 20, Span 80, or Octyl glucoside were used as stabilizers/surface-altering agents, stable nanosuspensions could not be obtained. Therefore, these stabilizers/surface-altering agents were excluded from further investigation due to their inability to effectively aid particle size reduction.

TABLE 3

Particle size measured by DLS in nanosuspensions obtained by milling of Pyrene with various stabilizers/surface-altering agents.

| Stabilizer | N-Ave. D (nm) |
| --- | --- |
| Pluronic ® F127 | 239 |
| Pluronic ® F108 | 267 |
| Pluronic ® P105 | 303 |
| Pluronic ® P103 | 319 |
| Pluronic ® P123 | 348 |
| Pluronic ® L121 | 418 |
| Pluronic ® F68 | 353 |
| Pluronic ® P65 | 329 |
| Pluronic ® F87 | 342 |
| Pluronic ® F38 | 298 |
| Pluronic ® L101 | not measurable* |
| Pluronic ® L81 | not measurable* |
| Pluronic ® L44 | not measurable* |
| Pluronic ® L31 | not measurable* |
| PVA 13K | 314 |
| PVA 31K | 220 |
| PVA 85K | 236 |
| Kollicoat IR | 192 |
| Kollidon 17 (PVP 9K) | 163 |
| Kollidon 25 (PVP 26K) | 210 |
| Kollindon 30 (PVP 43K) | 185 |
| Methocel E50 | 160 |
| Methocel K100 | 216 |
| Tween 20 | 381 |
| Tween 80 | 322 |
| Solutol HS | 378 |
| Triton X100 | 305 |
| Tyloxapol | 234 |
| Cremophor RH40 | 373 |
| SDS | 377 |
| CTAB | 354 |

TABLE 3-continued

Particle size measured by DLS in nanosuspensions obtained by milling of Pyrene with various stabilizers/surface-altering agents.

| Stabilizer | N-Ave. D (nm) |
| --- | --- |
| Span 20 | not measurable* |
| Span 80 | not measurable* |
| Octyl glucoside | not measurable* |

*milling with Pluronics ® L101, L81, L44, L31, Span 20, Span 80, Octyl glucoside failed to effectively reduce pyrene particle size and produce stable nanosuspensions.

The mobility and distribution of pyrene nanoparticles from the produced nanosuspensions in human cervicovaginal mucus (CVM) were characterized using fluorescence microscopy and multiple particle tracking software. In a typical experiment, ≤0.5 uL of a nanosuspension (diluted if necessary to the surfactant concentration of ~1%) was added to 20 μl of fresh CVM along with controls. Conventional nanoparticles (200 nm yellow-green fluorescent carboxylate-modified polystyrene microspheres from Invitrogen) were used as a negative control to confirm the barrier properties of the CVM samples. Red fluorescent polystyrene nanoparticles covalently coated with PEG 5 kDa were used as a positive control with well-established MPP behavior. Using a fluorescent microscope equipped with a CCD camera, 15 s movies were captured at a temporal resolution of 66.7 ms (15 frames/s) under 100× magnification from several areas within each sample for each type of particles: sample (pyrene), negative control, and positive control (natural blue fluorescence of pyrene allowed observing of pyrene nanoparticles separately from the controls). Next, using an advanced image processing software, individual trajectories of multiple particles were measured over a time-scale of at least 3.335 s (50 frames). Resulting transport data are presented here in the form of trajectory-mean velocity $V_{mean}$, i.e., velocity of an individual particle averaged over its trajectory, and ensemble-average velocity $<V_{mean}>$, i.e., $V_{mean}$ averaged over an ensemble of particles. To enable easy comparison between different samples and normalize velocity data with respect to natural variability in penetrability of CVM samples, relative sample velocity $<V_{mean}>_{rel}$, was determined according to the formula shown in Equation 1.

Prior to quantifying mobility of the produced pyrene nanoparticles, their spatial distribution in the mucus sample was assessed by microscopy at low magnifications (10×, 40×). It was found that pyrene/Methocel nanosuspensions did not achieve uniform distribution in CVM and strongly aggregated into domains much larger than the mucus mesh size (data not shown). Such aggregation is indicative of mucoadhesive behavior and effectively prevents mucus penetration. Therefore, further quantitative analysis of particle mobility was deemed unnecessary. Similarly to the positive control, all other tested pyrene/stabilizer systems achieved a fairly uniform distribution in CVM. Multiple particle tracking confirmed that in all tested samples the negative controls were highly constrained, while the positive controls were highly mobile as demonstrated by $<V_{mean}>$ for the positive controls being significantly greater than those for the negative controls (Table 4).

ticles. These histograms illustrate muco-diffusive behavior of samples stabilized with Pluronic® F127 and Pluronic® F108 (similar histograms were obtained for samples stabilized with Pluronic® P123, P105, and P103, but are not shown here) as opposed to muco-adhesive behavior of samples stabilized with Pluronic® 87, and Kollidon 25 (chosen as representative muco-adhesive samples).

To identify the characteristics of Pluronics® that render pyrene nanocrystals mucus penetrating, $<V_{mean}>_{rel}$ of the Pyrene/Pluronic® nanocrystals was mapped with respect to molecular weight of the PPO block and the PEO weight

TABLE 4

Ensemble-average velocity $<V_{mean}>$ (um/s) and relative sample velocity $<V_{mean}>_{rel}$ for pyrene/stabilizer nanoparticles (sample) and controls in CVM.

| Stabilizer | Negative Control | | Positive Control | | Sample | | Sample (relative) | |
|---|---|---|---|---|---|---|---|---|
| | $<V_{mean}>$ | SD | $<V_{mean}>$ | SD | $<V_{mean}>$ | SD | $<V_{mean}>_{rel}$ | SD |
| Pluronic F127 | 0.58 | 0.18 | 5.97 | 0.54 | 6.25 | 0.72 | 1.05 | 0.18 |
| Pluronic F108 | 0.43 | 0.64 | 5.04 | 1.88 | 4.99 | 1.47 | 0.99 | 0.55 |
| Pluronic P105 | 0.56 | 0.52 | 4.38 | 1.36 | 4.47 | 2.11 | 1.02 | 0.69 |
| Pluronic P103 | 0.58 | 0.77 | 4.5 | 2.01 | 4.24 | 1.95 | 0.93 | 0.74 |
| Pluronic P123 | 0.56 | 0.44 | 4.56 | 1.44 | 3.99 | 1.66 | 0.86 | 0.54 |
| Pluronic L121 | 0.42 | 0.3 | 4.27 | 2.04 | 0.81 | 0.51 | 0.10 | 0.16 |
| Pluronic F68 | 0.56 | 0.52 | 4.38 | 1.36 | 0.81 | 0.7 | 0.07 | 0.23 |
| Pluronic P65 | 0.26 | 0.25 | 4.52 | 2.15 | 0.53 | 0.56 | 0.06 | 0.15 |
| Pluronic F87 | 0.95 | 1.6 | 5.06 | 1.34 | 0.74 | 0.78 | −0.05 | −0.43 |
| Pluronic F38 | 0.26 | 0.1 | 5.73 | 0.84 | 0.54 | 0.29 | 0.05 | 0.06 |
| Pluronic L101* | | | | | | | | |
| Pluronic L81* | | | | | | | | |
| Pluronic L44* | | | | | | | | |
| Pluronic L31* | | | | | | | | |
| Kollicoat IR | 0.62 | 0.62 | 5.39 | 0.55 | 0.92 | 0.81 | 0.06 | 0.22 |
| Kollidon 17 | 1.69 | 1.8 | 5.43 | 0.98 | 0.82 | 0.59 | −0.23 | −0.52 |
| Kollidon 25 | 0.41 | 0.34 | 5.04 | 0.64 | 1.29 | 1.09 | 0.19 | 0.25 |
| Kollindon 30 | 0.4 | 0.2 | 4.28 | 0.57 | 0.35 | 0.11 | −0.01 | 0.06 |
| Methocel E50** | | | | | | | | |
| Methocel K100** | | | | | | | | |
| Tween 20 | 0.77 | 0.93 | 5.35 | 1.76 | 1.58 | 2.02 | 0.18 | 0.49 |
| Tween 80 | 0.46 | 0.34 | 3.35 | 1.89 | 0.94 | 0.5 | 0.17 | 0.24 |
| Solutol HS | 0.42 | 0.13 | 3.49 | 0.5 | 0.8 | 0.6 | 0.12 | 0.20 |
| Triton X100 | 0.26 | 0.13 | 4.06 | 1.11 | 0.61 | 0.19 | 0.09 | 0.07 |
| Tyloxapol | 0.5 | 0.5 | 3.94 | 0.58 | 0.42 | 0.23 | −0.02 | −0.16 |
| Cremophor RH40 | 0.48 | 0.21 | 3.2 | 0.97 | 0.49 | 0.24 | 0.00 | 0.12 |
| Span 20* | | | | | | | | |
| Span 80* | | | | | | | | |
| Octyl glucoside* | | | | | | | | |
| SDS | 0.3 | 0.12 | 5.99 | 0.84 | 0.34 | 0.15 | 0.01 | 0.03 |
| CTAB | 0.39 | 0.09 | 4.75 | 1.79 | 0.32 | 0.31 | −0.02 | −0.07 |

*Did not produce stable nanosuspensions, hence not mucus-penetrating (velocity in CVM not measured)
**Aggregated in CVM, hence not mucus-penetrating (velocity in CVM not measured)

Figure 2A:
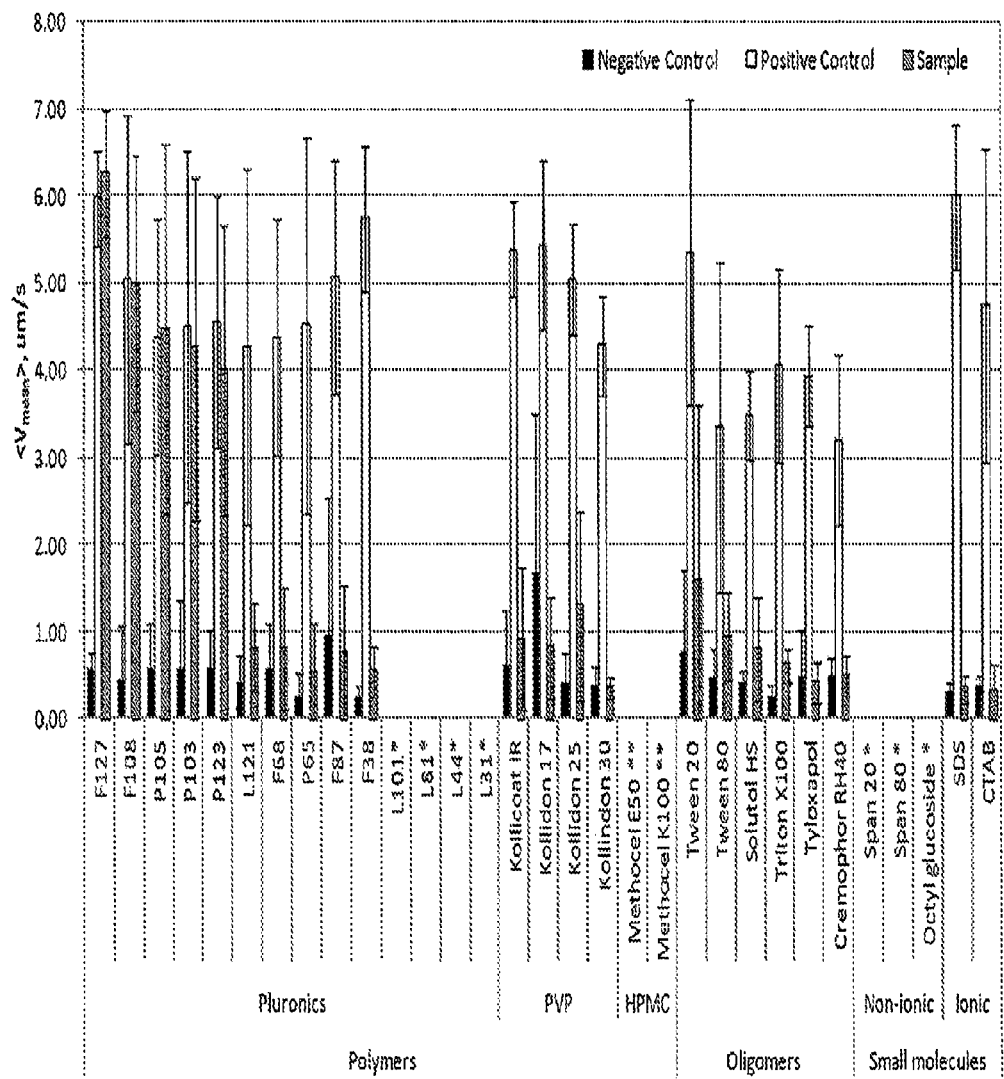
FIG. 2A is a plot showing the ensemble averaged velocity $<V_{mean}>$ in human cervicovaginal mucus (CVM) for 200 nm carboxylated polystyrene particles (negative control), 200 nm PEGylated polystyrene particles (positive control), and nanocrystal particles (sample) made by nanomilling and coated with different stabilizers/surface-altering agents according to one set of embodiments.

It was discovered that nanoparticles obtained in the presence of certain (but, importantly, not all) stabilizers/surface-altering agents migrate through CVM at the same rate or nearly the same velocity as the positive control. Specifically, pyrene nanoparticles stabilized with Pluronics® F127, F108, P123, P105, and P103 exhibited $<V_{mean}>$ that exceeded those of the negative controls by approximately an order of magnitude and were indistinguishable, within experimental error, from those of the positive controls, as shown in Table 4 and FIG. 2A. For these samples, $<V_{mean}>_{rel}$ values exceeded 0.5, as shown in FIG. 2B.

Figure 2B:
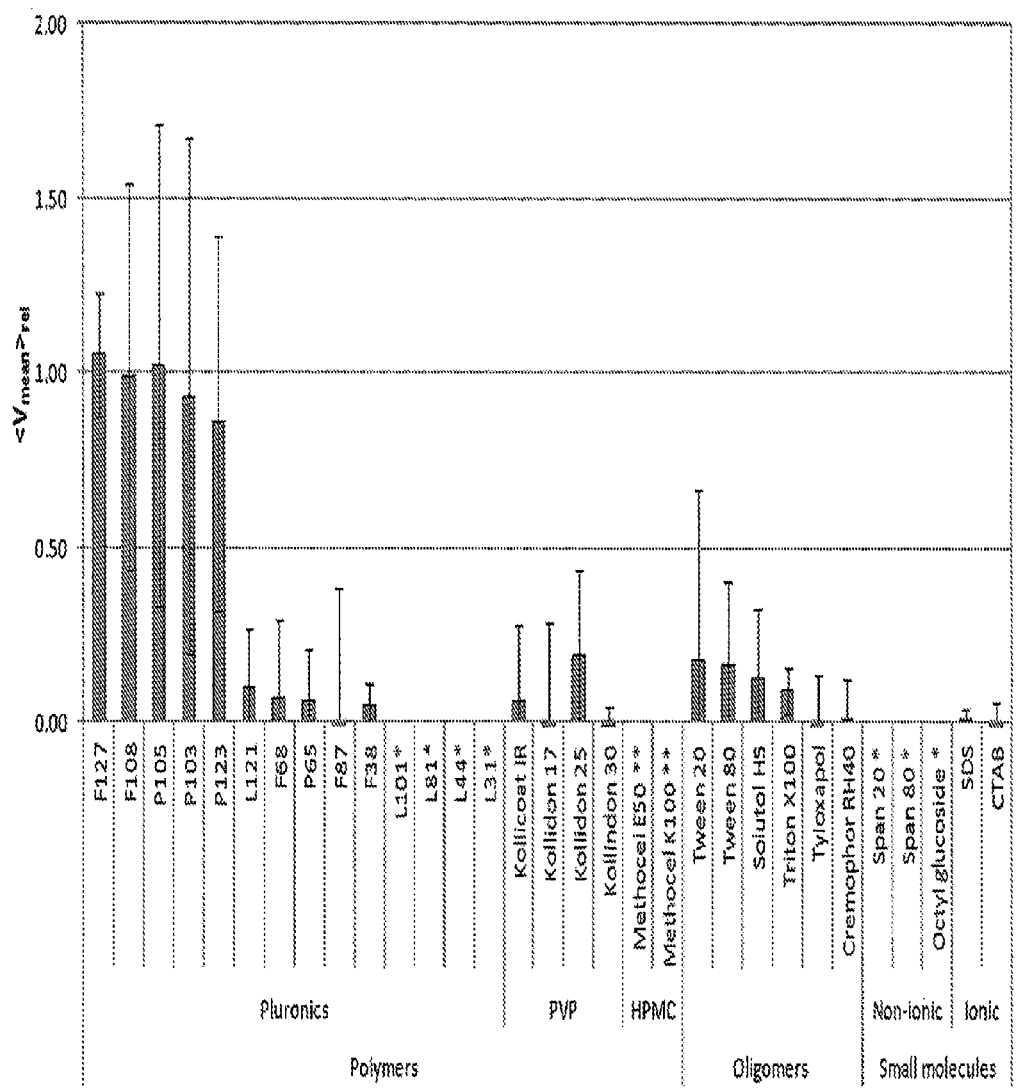
FIG. 2B is a plot showing the relative velocity $<V_{mean}>_{rel}$ in CVM for nanocrystal particles made by nanomilling and coated with different stabilizers/surface-altering agents according to one set of embodiments.
Figure 3A:
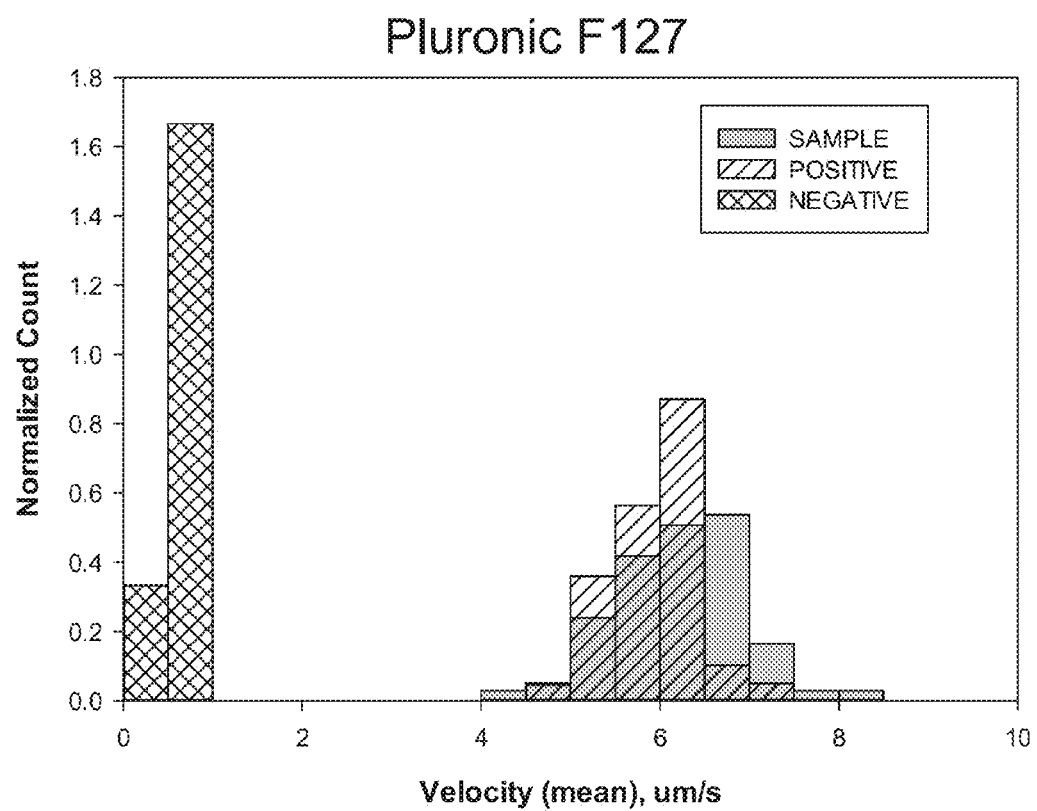
FIGS. 3A-3D are histograms showing distribution of trajectory-mean velocity $V_{mean}$ in CVM within an ensemble of nanocrystal particles coated with different surface-altering agents according to one set of embodiments.
Figure 3B:
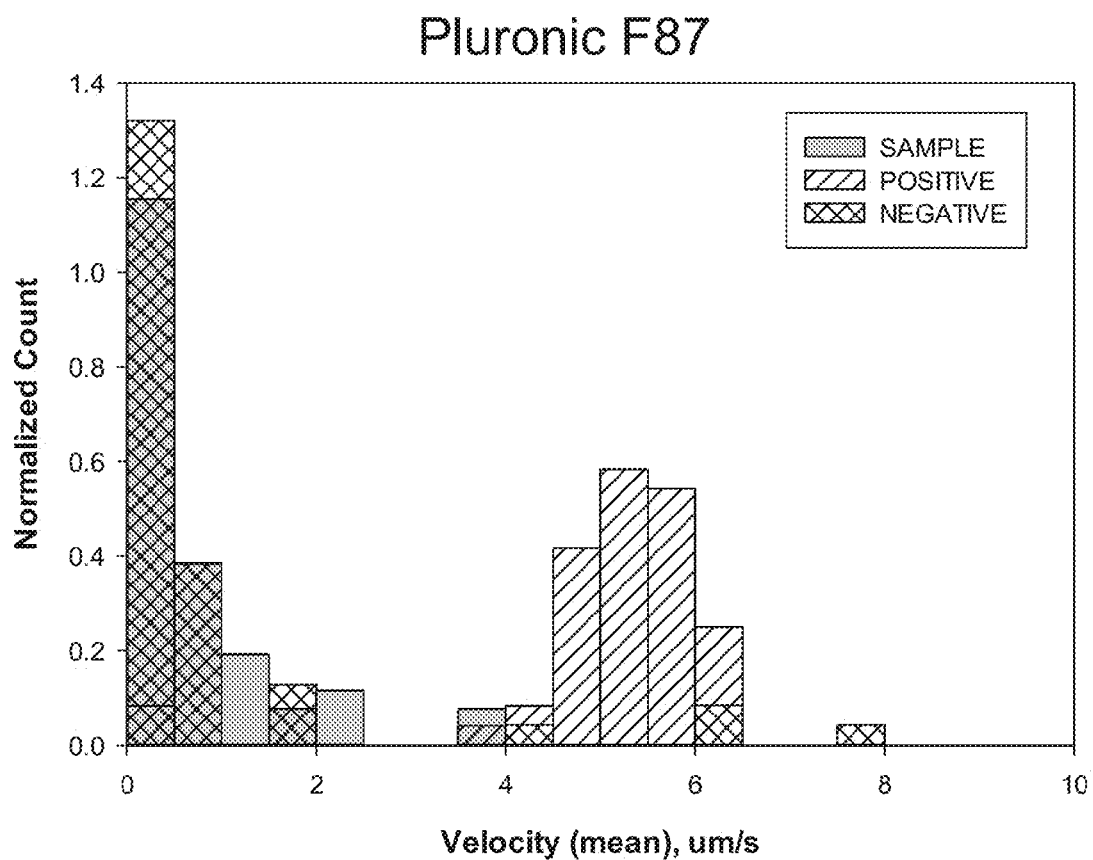
Figure 3C:
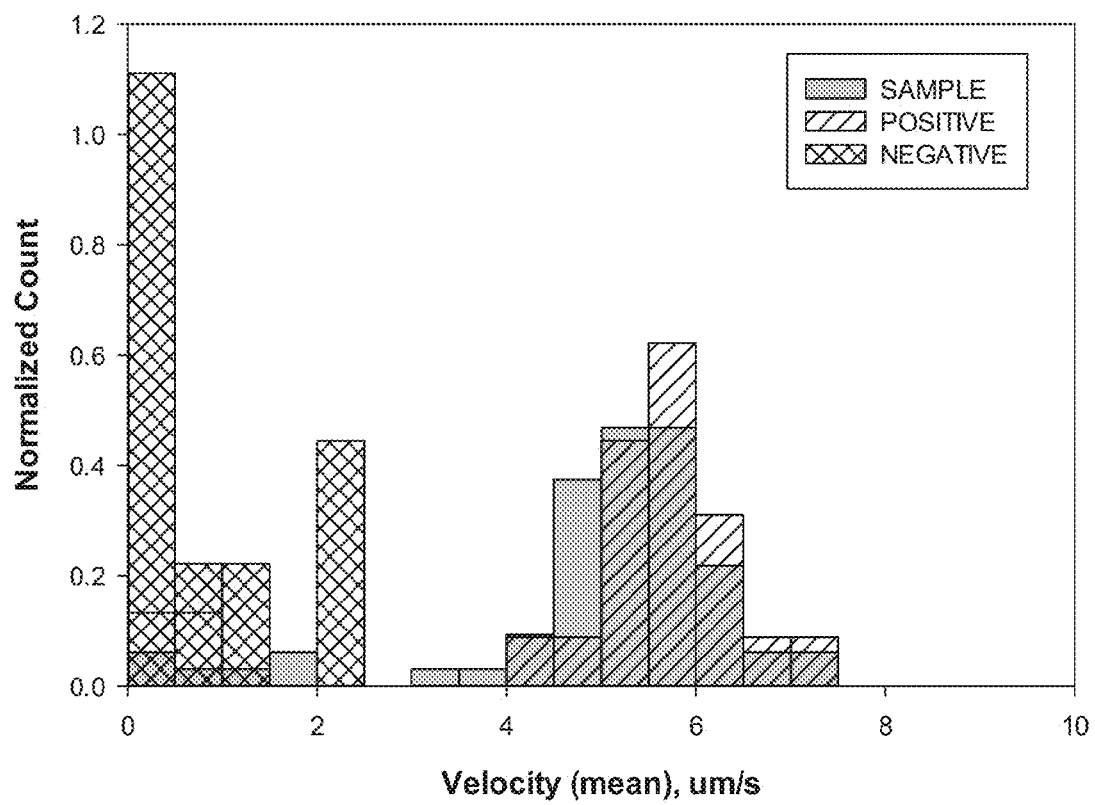
Figure 3D:
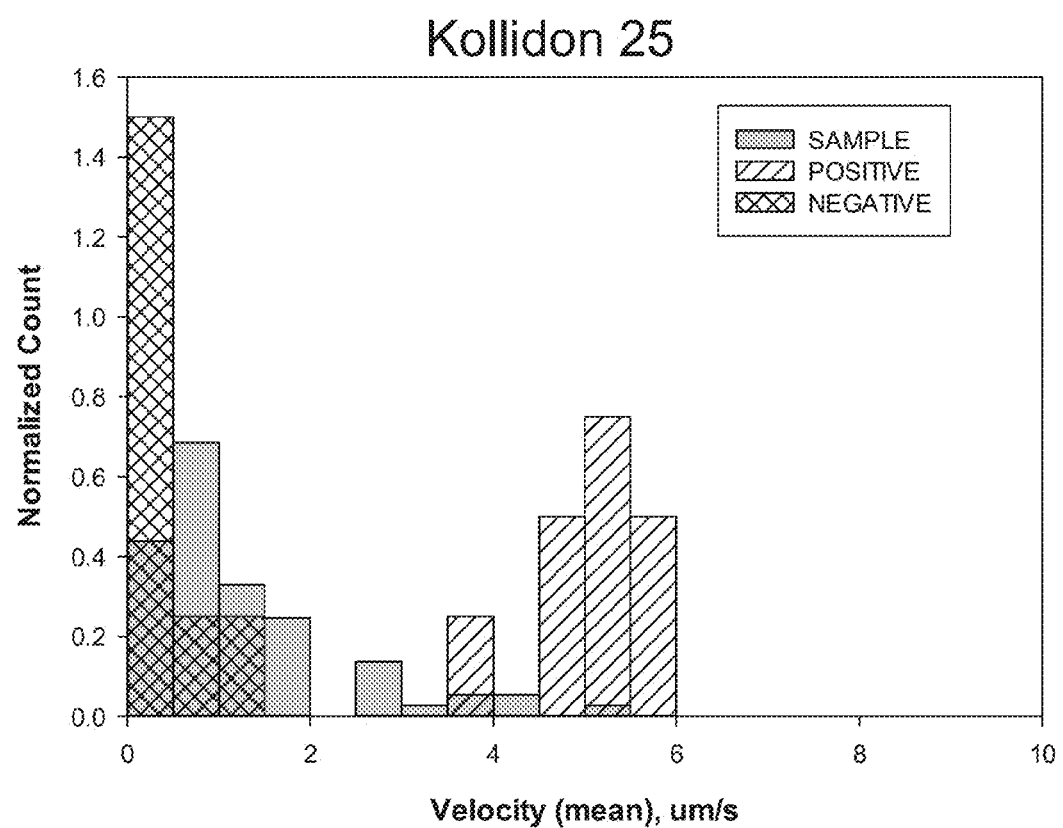
Figure 4:
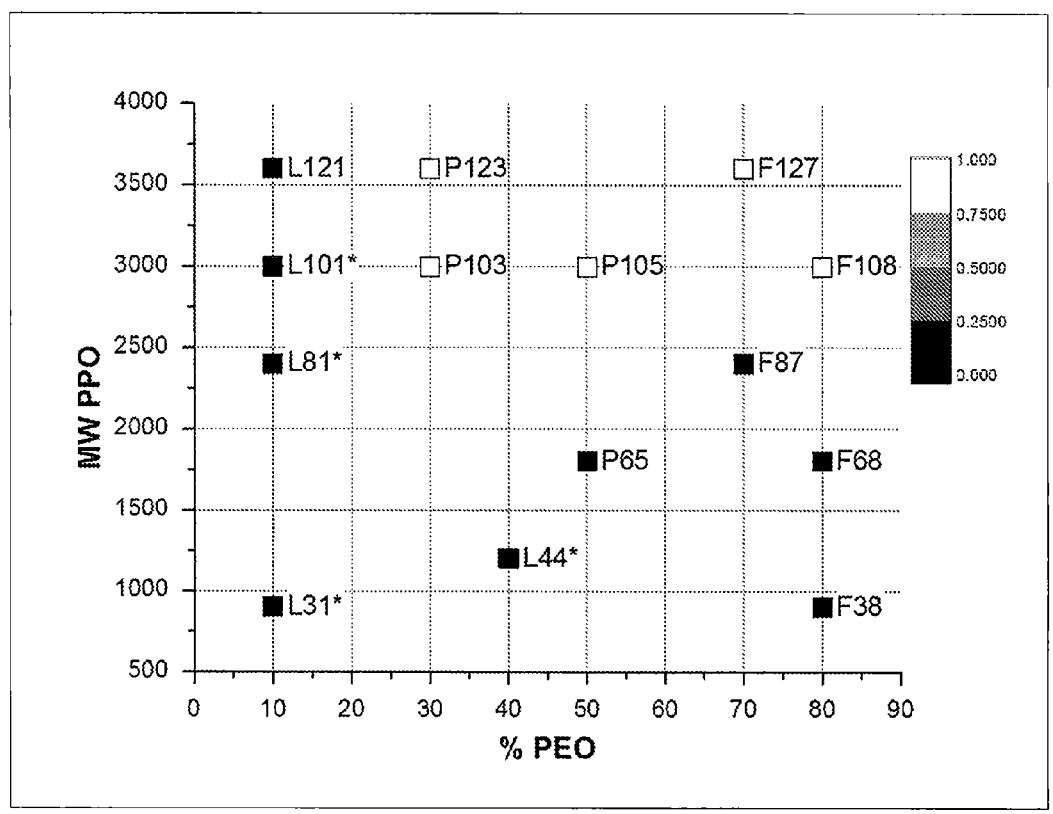
FIG. 4 is a plot showing $<V_{mean}>_{rel}$ in CVM for nanocrystal particles coated with different PEO-PPO-PEO Pluronic® triblock copolymers, mapped with respect to molecular weight of the PPO block and the PEO weight content (%), according to one set of embodiments.

On the other hand, pyrene nanoparticles obtained with the other stabilizers/surface-altering agents were predominantly or completely immobilized as demonstrated by respective $<V_{mean}>_{rel}$ values of no greater than 0.4 and, with most stabilizers/surface-altering agents, no greater than 0.1 (Table 4 and FIG. 2B). Additionally, FIGS. 3A-3D are histograms showing distribution of $V_{mean}$ within an ensemble of parcontent (%) of the Pluronics® used (FIG. 4). It was concluded that at least those Pluronics® that have the PPO block of at least 3 kDa and the PEO content of at least about 30 wt % rendered the nanocrystals mucus-penetrating. Without wishing to be bound by any theory, it is believed that the hydrophobic PPO block can provide effective association with the surface of the core particles if the molecular weight of that block is sufficient (e.g., at least about 3 kDa in some embodiments); while the hydrophilic PEO blocks are present at the surface of the coated particles and can shield the coated particles from adhesive interactions with mucin fibers if the PEO content of the Pluronic® is sufficient (e.g., at least 30 wt % in some embodiments). As described herein, in some embodiments the PEO content of the surface-altering agent may be chosen to be greater than about 10 wt % (e.g., at least about 15 wt %, or at least about 20 wt %), as a 10 wt % PEO portion rendered the particles mucoadhesive.

Example 2

This example describes the formation of mucus-penetrating particles using various non-polymeric solid particles.

The technique described in Example 1 was applied to other non-polymeric solid particles to show the versatility of the approach. F127 was used as the surface-altering agent for coating a variety of active pharmaceuticals used as core particles. Sodium dodecyl sulfate (SDS) was chosen as a negative control so that each drug was compared to a similarly sized nanoparticle of the same compound. An aqueous dispersion containing the pharmaceutical agent and Pluronic® F127 or SDS was milled with milling media until particle size was reduced below 300 nm. Table 5 lists the particle sizes for a representative selection of drugs that were milled using this method.

TABLE 5

Particle sizes for a representative selection of drugs milled in the presence of SDS and F127.

| Drug | Stabilizer | Z-Ave D (nm) | PDI |
| --- | --- | --- | --- |
| Fluticasone Propionate | F127 | 203 | 0.114 |
|  | SDS | 202 | 0.193 |
| Furosemide | F127 | 217 | 0.119 |
|  | SDS | 200 | 0.146 |
| Itraconazole | F127 | 155 | 0.158 |
|  | SDS | 168 | 0.163 |
| Prednisolone | F127 | 273 | 0.090 |
|  | SDS | 245 | 0.120 |
| Loteprednol Etabonate | F127 | 241 | 0.123 |
|  | SDS | 241 | 0.130 |
| Budesonide | F127 | 173 | 0.112 |
|  | SDS | 194 | 0.135 |
| Indomethacin | F127 | 225 | 0.123 |
|  | SDS | 216 | 0.154 |

Figure 5:
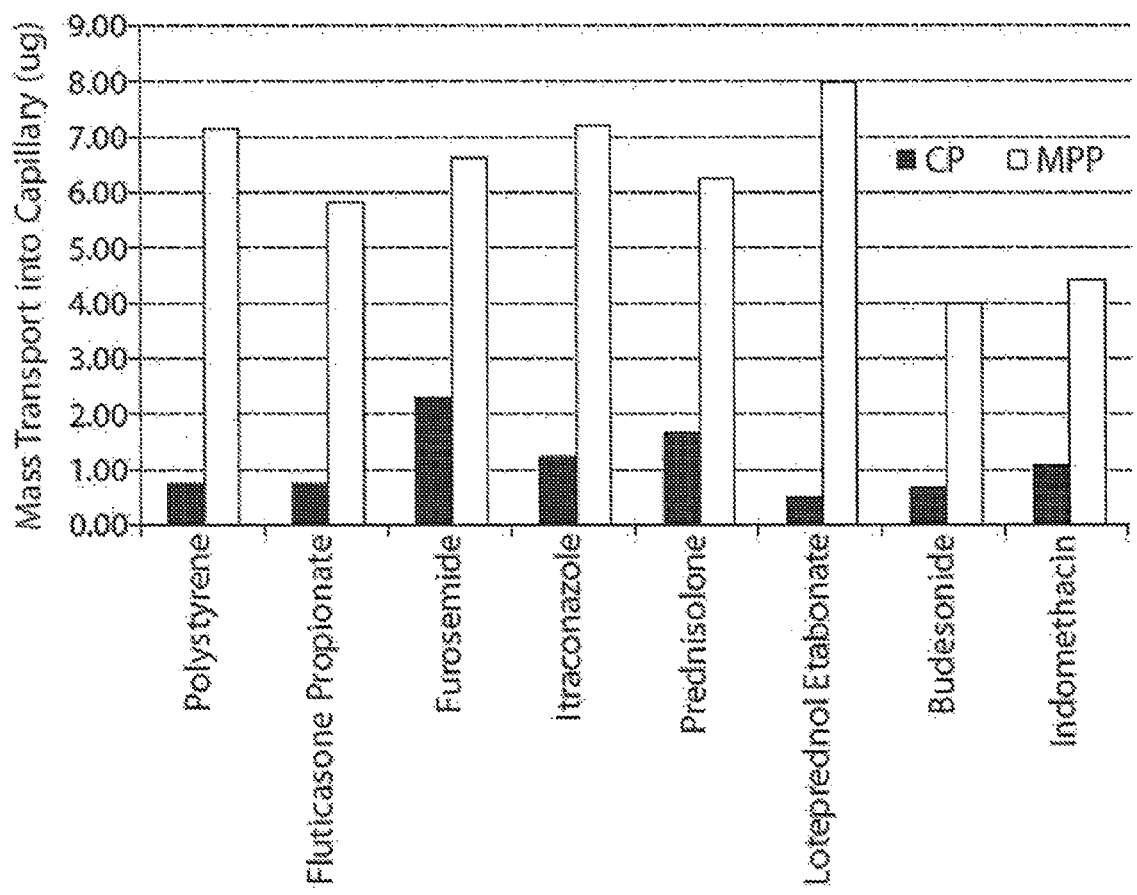
FIG. 5 is a plot showing the mass transport through CVM for solid particles having different core materials that are coated with either Pluronic® F127 (MPP) or sodium dodecyl sulfate (CP, a negative control), according to one set of embodiments.

In order to measure the ability of drug nanoparticles to penetrate mucus a new assay was developed which measures the mass transport of nanoparticles into a mucus sample. Most drugs are not naturally fluorescent and are therefore difficult to measure with particle tracking microscopy techniques. The newly-developed bulk transport assay does not require the analyzed particles to be fluorescent or labeled with dye. In this method, 20 μL of CVM is collected in a capillary tube and one end is sealed with clay. The open end of the capillary tube is then submerged in 20 μL of an aqueous suspension of particles which is 0.5% w/v drug. After the desired time, typically 18 hours, the capillary tube is removed from the suspension and the outside is wiped clean. The capillary containing the mucus sample is placed in an ultracentrifuge tube. Extraction media is added to the tube and incubated for 1 hour while mixing which removes the mucus from the capillary tube and extracts the drug from the mucus. The sample is then spun to remove mucins and other non-soluble components. The amount of drug in the extracted sample can then be quantified using HPLC. The results of these experiments are in good agreement with those of the microscopy method, showing clear differentiation in transport between mucus penetrating particles and conventional particles (CP). The transport results for a representative selection of drugs are shown in FIG. 5. These results corroborate microscopy/particle tracking findings with Pyrene and demonstrate the extension to common active pharmaceutical compounds; coating non-polymeric solid nanoparticles with F127 enhances mucus penetration.

In Examples 1-2, cervicovaginal mucus (CVM) samples were obtained from healthy females volunteers age 18 years or older. CVM was collected by inserting a Softcup® menstrual collection cup into the vaginal tract as described by the product literature for between 30 seconds and 2 minutes. After removal the CVM was then collected from the Softcup® by gentle centrifugation at ~30×G to ~120×G in a 50 mL centrifuge tube. In Example 1, CVM was used undiluted and fresh (stored for no longer than 7 days under refrigerated conditions). Barrier and transport of all CVM samples used in Example 1 were verified with negative (200 nm carboxylated polystyrene particles) and positive (200 nm polystyrene particles modified with PEG 5K) controls. In Example 2, CVM was lyophilized and reconstituted. In Example 2, mucus was frozen at −50° C. and then lyophilized to dryness. Samples were then stored at −50° C. Before use, the mucus was reconstituted by grinding the solid into a fine powder using a mortar and pestle followed by water addition to a final volume equal to the original volume to 2 times the original volume. The reconstituted mucus was then incubated at 4° C. for 12 hours and used as described in Example 2. Barrier and transport of all CVM samples used in Example 2 were verified with negative (200 nm carboxylated polystyrene particles) and positive (F127 coated 200 nm polystyrene particles) controls.

Example 3

This example describes the formation of mucus-penetrating particles using a core comprising the drug loteprednol etabonate (LE).

Figure 6A:
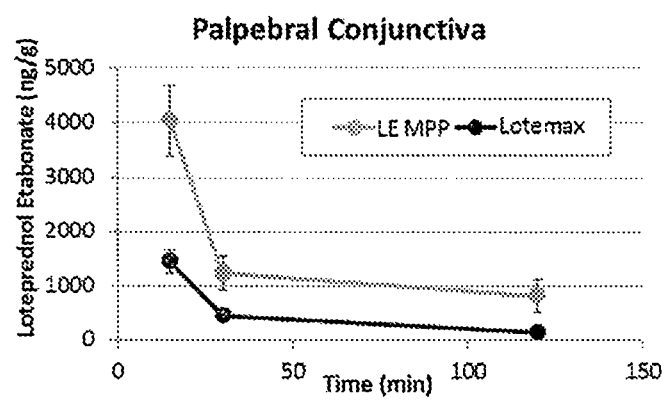
FIGS. 6A-6C show drug levels of loteprednol etabonate in the palpebral conjunctiva (FIG. 6A), bulbar conjunctiva (FIG. 6B), and cornea (FIG. 6C) of New Zealand white rabbits after administration of prescription loteprednol etabonate, Lotemax®, or particles of loteprednol etabonate that were coated with Pluronic® F127, according to one set of embodiments.
Figure 6B:
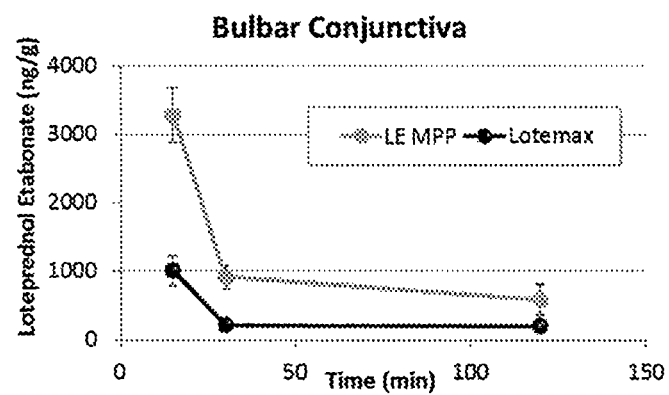
Figure 6C:
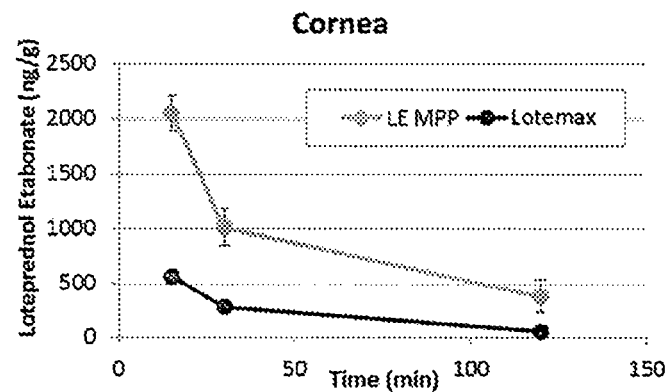

In order to demonstrate the value of enhanced mucus penetration in the delivery of non-polymeric solid particles, an MPP formulation of loteprednol etabonate (LE MPP; LE particles coated with Pluronic® F127 made by the method described in Example 2) was compared to the currently marketed formulation, Lotemax®. Lotemax® is a steroid eye drop approved for the treatment of surface ocular inflammation. Conventional particles, such as those in Lotemax®, are extensively trapped by the peripheral rapidly-cleared mucus layer in the eye and, hence, are also rapidly cleared. LE MPP are able to avoid adhesion to, and effectively penetrate through, mucus to facilitate sustained drug release directly to underlying tissues. Enhancing drug exposure at the target site would allow the overall dose to be reduced, increasing patient compliance and safety. In vivo, a single topical instillation of LE MPP to New Zealand white rabbits produced significantly higher drug levels in palpebral conjunctiva, bulbar conjunctiva, and cornea compared to an equivalent dose of Lotemax® (FIGS. 6A-6C). At 2 hours LE levels from MPP are 6, 3, and 8 times higher than from Lotemax® (palpebral, bulbar, and cornea, respectively). Notably, LE levels from MPP are approximately 2 times higher at 2 hours than levels from Lotemax® at 30 minutes. These results demonstrate the utility of the non-polymeric solid MPP approach.

Example 4

This example describes the formation of mucus-penetrating particles including a core comprising curcumin (CUR).

Molecules with various solubilities were selected as model therapeutic agents for forming particles having a core of a solid pharmaceutical agent. One of them, curcumin, is suggested to have antioxidant, antitumor and anti-inflammatory properties. It is an interesting candidate not only because of its broad potential medical applications, but also its high hydrophobicity and natural fluorescence. The former feature means that CUR is poorly soluble in aqueous solutions, while the latter allows rapid and label-free detection and characterization of the particles. The particles were coated with surfactants (e.g., Pluronic® F127, abbreviated as F127 in Examples 4 and 5) to render them mucus-penetrating.

A simple procedure based on ultrasonication was developed to formulate particles of CUR. Briefly, 5 mg CUR was dispersed in 2 mL aqueous solution containing F127 (or other surfactants) in a 7 mL scintillation vial. The suspension was sonicated in a water bath for 20 min. The curcumin suspension was then sonicated using an ultra-sonicator with a 3 mm stepped probe at 100% amplitude for 30 min. The suspension was centrifuged at 2000 rpm for 10 min to remove unbroken crystals. The supernatant was stored at 4 C for 2 hours. The supernatant was centrifuged at 16,500 rpm for 20 min, and then the pellet was collected. It was noticed that without sufficient incubation time before particle collection, the diffusivity of the coated particles was much lower (data not shown), suggesting the importance of a dense F127 coating in the generation of mucus-penetrating particles.

Figure 7A:
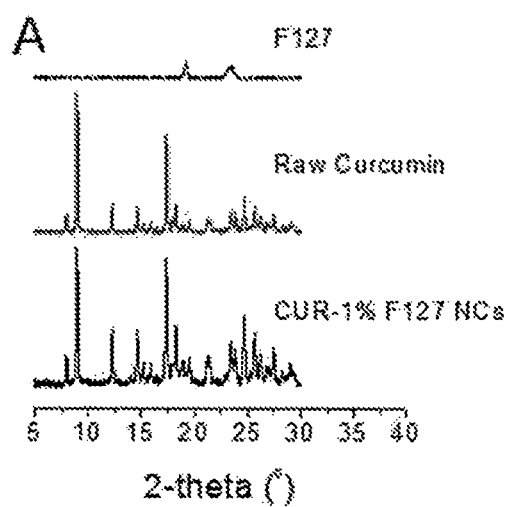
FIGS. 7A and 7B are physicochemical characterizations of CUR-1% F127 particles according to one set of embodiments.
Figure 7B:
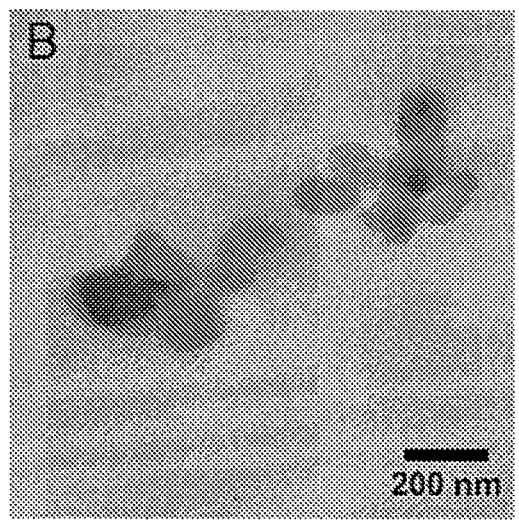

Table 6 and (FIGS. 7A-7B) summarize the physicochemical properties of the resulting coated CUR particles prepared using the above method. CUR particles formulated in 1% (w/v) F127 (CUR-1% F127 particles) possessed an average size of 133 nm, which was consistent with the observation through TEM images (FIG. 7B). The Zeta-potential was close to neutral. As F127 concentration in the CUR suspension during ultra-sonication was decreased, CUR particle size and polydispersity (PDI) each increased, likely as a result of reduced F127 coating density leading to weakened stabilizing effect on CUR particles (Table 6). There was little effect of F127 concentration on particle Zeta-potential, which is likely attributed to the deionization of curcumin at pH 4. Powder-XRD measurement on CUR-1% F127 particles indicated that the chemical structure and crystallinity of CUR were not altered by either ultrasonication or the incorporation of F127 (FIG. 7A).

TABLE 6

Size and Zeta-potential of CUR particles prepared in different concentrations of F127 and their diffusivity in human cervicovaginal mucus ($D_m$) compared to in water ($D_w$)

| Sample Description*** | Size (nm)* | Polydispersity Index | Zeta-potential (mV)* | $D_w/D_m$** |
|---|---|---|---|---|
| CUR-1% F127 particles | 133 ± 12 | 0.33 ± 0.05 | −0.8 ± 0.1 | 9 |
| CUR-0.1% F127 particles | 154 ± 4 | 0.50 ± 0.02 | −1.4 ± 0.4 | 11 |
| CUR-0.01% F127 particles | 176 ± 11 | 0.57 ± 0.03 | −1.6 ± 0.3 | 35 |
| CUR-0.001% F127 particles | 184 ± 30 | 0.72 ± 0.03 | −1.3 ± 0.5 | 10000 |

*Size and Zeta-potential were measured in 10 mM NaCl (pH = 4) via dynamic light scattering and laser Doppler anemometry, respectively. Data represent mean ± standard error (n = 3).
**$D_w$ is calculated from the Stokes-Einstein equation using average particle size and $D_m$ is the geometric ensemble average effective diffusivity (<Deff>) calculated at a time scale of 1 s.
***The percentage of F127 indicates its concentration (% w/v) during the preparation of CUR particles.

To examine the mucus-penetrating properties of CUR-F127 particles, the transport of CUR-1% F127 particles was studied using multiple particle tracking (MPT) in both human cervicovaginal mucus (CVM) and human cystic fibrosis sputum (CFS) samples. In brief, the particles were added to mucus samples and their motion was recorded using high resolution epi-fluorescence microscopy. Their trajectories and transport rates were then analyzed and quantified. FIGS. 8A-8B show the time-dependent ensemble averaged geometric mean square displacement (<MSD>) of CUR-1% F127 particles in both CVM and CFS. 200 nm PEGylated (PEG) and carboxylated (COOH) polystyrene (PS) particles were selected as muco-inert and muco-adhesive controls, respectively. For the entire range of studied time scales, the <MSD> of CUR-1% F127 particles was comparable to that of PSPEG in CVM, and significantly higher than that of PSCOOH in both types of mucus samples. At a time scale of 1s, the <MSD> of CUR-1% F127 particles was 4400-fold and 220-fold higher than that of PSCOOH in CVM and CFS, respectively. The geometric ensemble averaged effective diffusivity (<Deff>) of CUR-1% F127 particles at a time scale of is was only 9-fold lower than the calculated theoretical diffusivity in water (Table 6).

Figure 9:
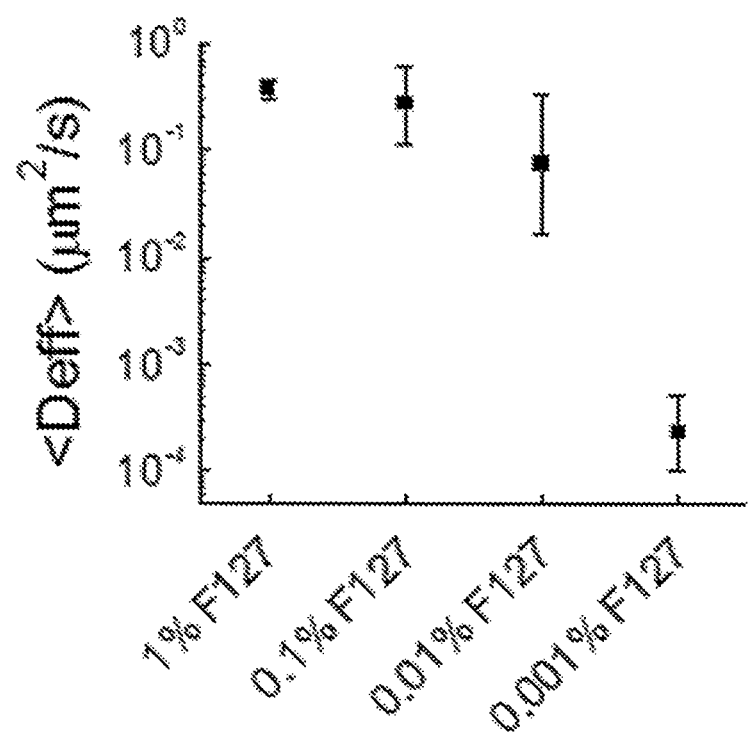
FIG. 9 is a plot showing geometric ensemble effective diffusivity (<Deff>) at a time scale of 1 s for CUR particles formulated in different concentrations of F127 in human CVM according to one set of embodiments. Data represents the ensemble average of at least 3 independent experiments, with n≥100 for each experiment. Error bars indicate geometric standard error.

To further investigate the effect of the coating density of F127 on the transport of CUR particles in mucus, the particles were formulated at various F127 concentrations and their diffusivities were characterized in human CVM (FIG. 9, Table 6). The <Deff> of CUR-0.1% and 0.01% F127 particles were either similar or slightly reduced as compared to that of CUR-1% F127 particles, but the transport of CUR-0.001% F127 particles was dramatically hindered (FIG. 9). The diffusivity of CUR-0.001% F127 particles was 10000-fold slower in human CVM as compared to in water, and about 1000-fold lower than that of CUR-1% F127 particles in CVM. In general, reducing the F127 concentration in the preparation of CUR particles resulted in a decrease of diffusivity, probably because the decreased F127 concentration lowered the surface density of F127 (and thereby the PEG brushes) at equilibrium. It was not obvious that this effect would become so pronounced when the F127 concentration dipped below 0.01% (w/v).

TABLE 7

Size and Zeta-potential of CUR particles prepared in different Pluronics ® and their diffusivity in human cervicovaginal mucus ($D_m$) compared to in water ($D_w$)

| Sample Description | Size (nm)* | Polydispersity Index | Zeta-potential (mV)* | $D_w/D_m$** |
|---|---|---|---|---|
| CUR-1% F38 particles | 232 ± 46 | 0.56 ± 0.01 | −1.2 ± 0.5 | 60 |
| CUR-1% P65 particles | 187 ± 34 | 0.48 ± 0.05 | −1.5 ± 0.3 | 1600 |
| CUR-1% P68 particles | 154 ± 20 | 0.53 ± 0.02 | −1.4 ± 0.5 | 150 |
| CUR-1% P84 particles | 138 ± 12 | 0.38 ± 0.02 | −1.3 ± 0.5 | 30 |
| CUR-1% P85 particles | 149 ± 16 | 0.43 ± 0.05 | −1.3 ± 0.3 | 30 |
| CUR-1% F88 particles | 130 ± 19 | 0.51 ± 0.04 | −0.5 ± 0.5 | 20 |
| CUR-1% F98 particles | 123 ± 34 | 0.50 ± 0.02 | −0.8 ± 0.1 | 12 |
| CUR-1% P103 particles | 141 ± 4 | 0.50 ± 0.02 | −1.4 ± 0.3 | 8 |
| CUR-1% P104 particles | 110 ± 18 | 0.45 ± 0.01 | −1.8 ± 0.6 | 12 |
| CUR-1% P105 particles | 90 ± 8 | 0.54 ± 0.02 | −1.0 ± 0.5 | 15 |
| CUR-1% F108 particles | 135 ± 21 | 0.52 ± 0.03 | −0.6 ± 0.1 | 11 |
| CUR-1% P123 particles | 123 ± 11 | 0.60 ± 0.06 | −2.3 ± 0.5 | 9 |

*Size and Zeta-potential of particles were measured in 10 mM NaCl (pH = 4) via dynamic light scattering and laser Doppler anemometry, respectively. Data represent mean ± standard error (n = 3).
**$D_w$ is calculated from the Stokes-Einstein equation using average particle diameter and $D_m$ is the ensemble average effective diffusivity calculated at a time scale of 1 s.

A variety of Pluronics®, in addition to F127, have been used for pharmaceutical applications. Different Pluronics® were tested to see if they would work equally well, or if only certain ones would transform CUR particles into mucus-penetrating particles. Twelve additional Pluronics®, as listed (in order of increasing PPO MW) in Table 7, were selected and the corresponding CUR particles were prepared. The resulting size ranged from 90 to 232 nm, while mostly staying between 100-150 nm. All the particle types showed a PDI larger than that of CUR-1% F127 particles (0.33), falling mostly between 0.4-0.6. These result implied that F127 may have the strongest stabilizing effect among all the tested Pluronics®. The Zeta-potential was uniformly neutral for all the studied CUR particles.

The transport rates of the CUR particles coated with various Pluronics® were characterized in human CVM (Table 7). By comparing their diffusivity to that of CUR-1% F127 particles (Dw/Dm=9), they could be clustered into three groups: particle motion strongly hindered (F65, F68; Dw/Dm>100), particle motion hindered (F38, F84, F85, F88; 20≤Dw/Dm≤100), and particles rapidly penetrating (F98, P103, P104, P105, F108, F123; Dw/Dm<20). The fact that the particles all possessed near neutral surface charge, but that only formulations with certain Pluronic® coatings exhibited strongly hindered diffusivity (e.g., F65 and F68), suggests that the adhesiveness between these CUR particles and mucus components is likely dominated by hydrophobic interactions.

Figure 10A:
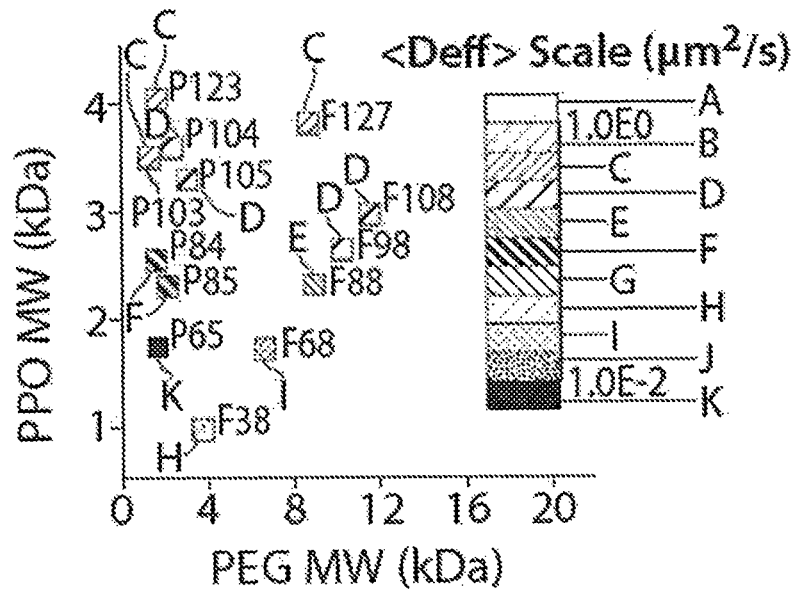
FIGS. 10A-10C are plots showing diffusivity of CUR particles formulated with different Pluronics® in human CVM according to one set of embodiments.
Figure 10B:
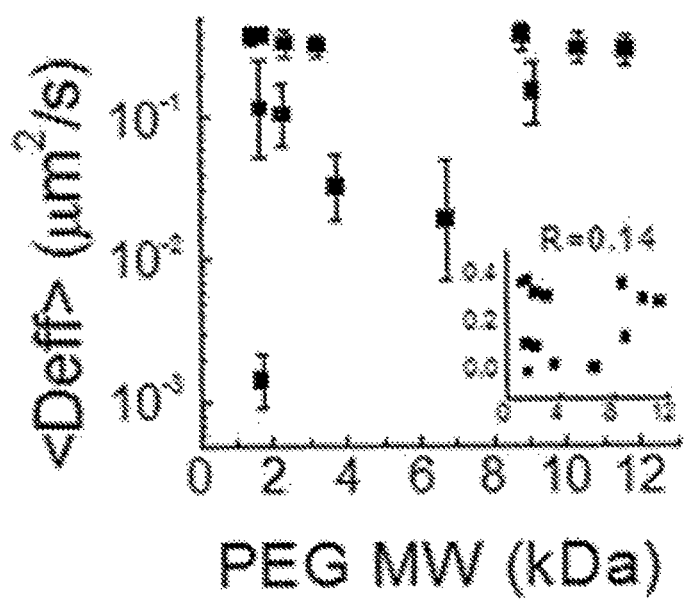
Figure 10C:
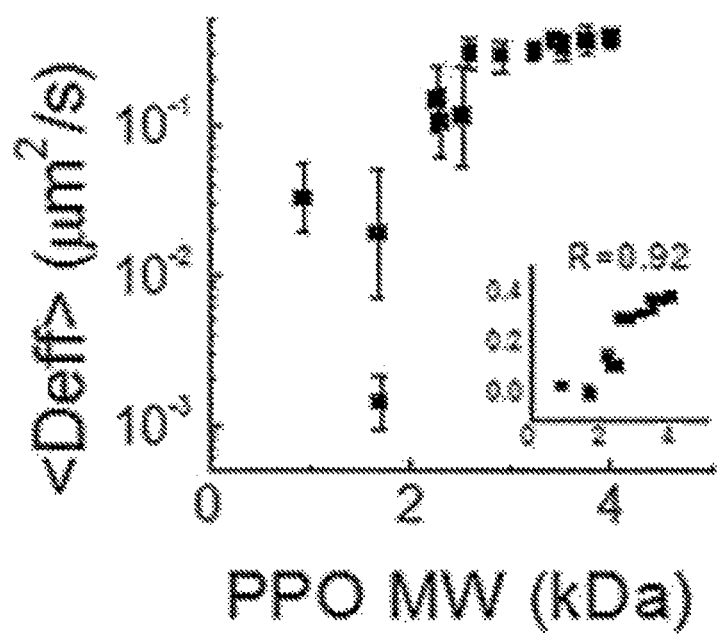

To identify the factors determining the diffusivity of CUR particles coated with different Pluronics®, <Deff> (at a time scale of 1 s) of the CUR particles was mapped with regards to the PPO and PEG MW of the used Pluronics® (FIG. 10A). A general increase of <Deff> was observed along with the growing length of PPO segment (Y-axis), yet no specific pattern between <Deff> and the PEG MW (X-axis). Surprisingly, this transition occurred at a PPO MW around 2000 Da, which is smaller than previous found for Pluronic® coated polystyrene particles. Particle diffusivity exhibited a strong correlation with the PPO MW (R=0.92), but little correlation with the PEG MW (R=0.14). It is likely that Pluronics® with longer PPO segments might have higher affinity to the hydrophobic surface of CUR particles, thus anchor more tightly and provide denser and more stable shielding on the surface.

To explore the capability of surfactants other than Pluronics® to potentially generate mucus-penetrating particles, Tween 20, Tween 80 and Vitamin E TPGS, all containing PEG segments, were tested. Characteristics of CUR particles prepared in these surfactants are listed in Table 8. Although all three groups demonstrated particle size around 150 nm and Zeta-potential close to neutral, their diffusivity was greatly reduced in human CVM compared to in water. The lower transport rates might indicate ineffective coating of surfactant molecules on the surface of CUR particles, which may be attributed to their shorter hydrophobic segments as compared to F127.

Figure 11:
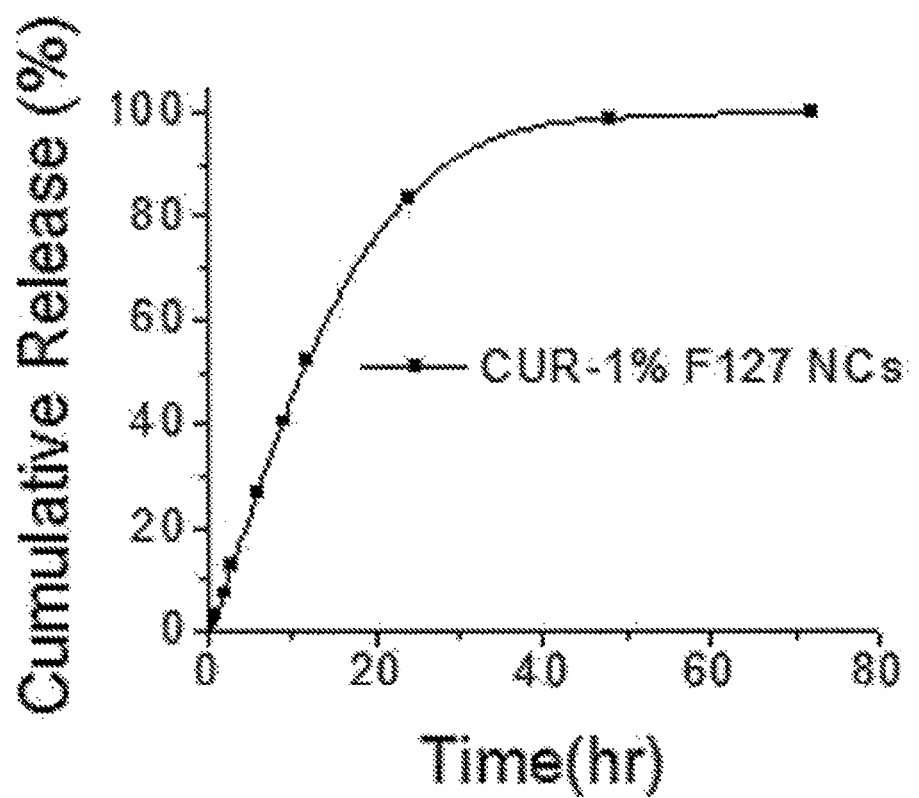
FIG. 11 is a plot showing cumulative release of CUR-1% F127 particles in phosphate buffered saline (pH=7.4) with octanol extraction according to one set of embodiments.
Figure 12:
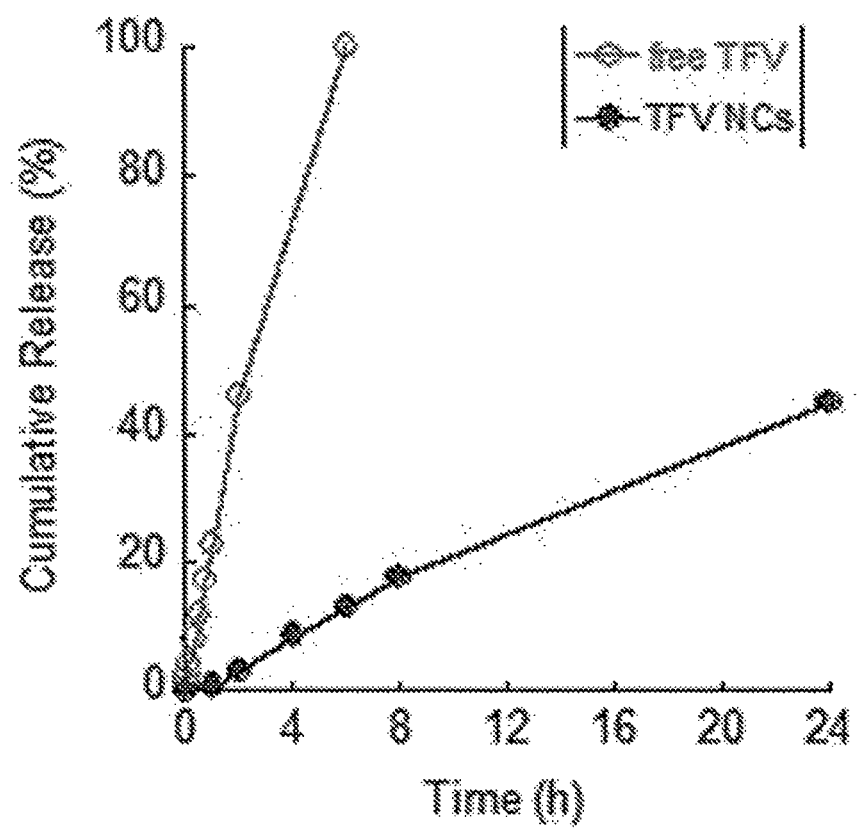
FIG. 12 is a plot showing cumulative release from a dialysis bag of free TFV in solution vs. TFV-Zn particles in suspension into normal phosphate buffered saline according to one set of embodiments.

In order to evaluate the ability of CUR particles to deliver CUR in a sustained fashion, the release profile of CUR-1% F127 particles was characterized. In brief, a known amount of CUR particles was suspended in phosphate buffered saline (PBS, pH 7.4) in a 50 mL tube with a layer of octanol added on top to extract the dissolved CUR. The suspension was incubated at 37° C. with agitation. Octanol was collected and replaced at each time point. The concentration of CUR in octanol was determined by fluorometry. As shown in FIG. 11, CUR-1% F127 particles provided continuous release for 24-48 hours in vitro. About 80% of the CUR content was released within the first 24 hours.

Example 5

This example describes the development of mucus-penetrating particles using a hydrophobic drug, 5,10,15,20-tetra (p-hydroxyphenyl)porphyrin (p-THPP).

In addition to CUR, the same method described in Example 4 was applied the hydrophobic drug, p-THPP. p-THPP is a therapeutic agent used for photodynamic therapy to treat cancer and has been selected as a model photosensitizer in previous studies. Basic properties of p-THPP-1% F127 particles, including size, Zeta-potential and diffusivity in human CVM were determined following the procedures described before (Table 9). Similar to CUR-1% F127 particles, p-THPP-1% F127 particles exhibited a size of 187 nm and a close-to-neutral surface charge. The diffusivity of p-THPP-1% F127 particles in human CVM was only 8-fold slower than that in water, indicating that the particles are not immobilized by the adhesive components in mucus and are able to diffuse through the mucus gel with a comparable rate to that of CUR particles-1% F127.

TABLE 9

Size and Zeta-potential of p-THPP particles prepared in Pluronic ® F127 and their diffusivity in human cervicovaginal mucus ($D_m$) compared to in water ($D_w$)

| Sample Description | Size (nm)* | Polydispersity Index | Zeta-potential (mV)* | $D_w/D_m$** |
|---|---|---|---|---|
| p-THPP-1% F127 particles | 187 ± 7 | 0.51 | 0.3 ± 0.4 | 8 |

*Size and Zeta-potential of particles were measured in 10 mM NaCl (pH = 4) via dynamic light scattering and laser Doppler anemometry, respectively. Data represent mean ± standard error (n = 3).
**$D_w$ is calculated from the Stokes-Einstein equation using average particle size and $D_m$ is the ensemble average effective diffusivity calculated at a time scale of 1 s.

TABLE 8

Size and Zeta-potential of CUR particles prepared in surfactants other than Pluronics ®, and their diffusivity in human cervicovaginal mucus ($D_m$) compared to in water ($D_w$)

| Sample Description | Diameter (nm)* | Polydispersity Index | Zeta-potential (mV)* | $D_w/D_m$** | $N_b$ ‡ | $N_m$ ‡ |
|---|---|---|---|---|---|---|
| CUR-1% Tween20 particles | 153 | 0.56 | −3.2 | 13000 | 1 | 1 |
| CUR-1% Tween80 particles | 155 | 0.60 | −2.9 | 480 | 1 | 1 |
| CUR-1% VitE-TPGS† particles | 135 | 0.68 | −2.5 | 1700 | 1 | 1 |

*Size and Zeta-potential of particles were measured in 10 mM NaCl (pH = 4) via dynamic light scattering and laser Doppler anemometry, respectively. Data represent mean ± standard error (n = 3).
**$D_w$ is calculated from the Stokes-Einstein equation using average particle size and $D_m$ is the ensemble average effective diffusivity calculated at a time scale of 1 s.
† VitE-TPGS: Vitamin-E TPGS (Vitamin-ETPGS (d-alpha tocopheryl polyethylene glycol 1000 succinate), from Antares Health Products, Inc. (Batavia, IL))
‡ $N_b$: number of batches of particles tested; $N_m$: number of human CVM samples tested.

Example 6

This example describes the development of mucus-penetrating particles using tenofovir (TFV) and acyclovir monophosphate (ACVp), highly water soluble drugs.

Tenofovir (TFV) is a potent antiviral drug used to treat infectious diseases. Due to the fact that tenofovir (TFV) is highly water soluble, a method was developed for formulating mucus-penetrating particles of tenofovir. The water solubility of TFV is at least 15 mg/mL, so conventional techniques for preparation of insoluble particles or, alternatively, encapsulation into hydrophobic polymeric nanoparticles, were not successful. In order to decrease the water solubility of TFV, interactions between cations and nucleotides/nucleotide analogs were exploited. TFV interacts very strongly with zinc cations (Zn), via the phosphonate group and the purine ring structure. This interaction with zinc causes TFV precipitation into crystals that can be stabilized with the coatings described herein, halting aggregation and determining the crystal surface properties. Additionally, Zn is naturally present in vaginal fluid and has known antimicrobial properties recently extended to include anti-HIV activity.

It was necessary to ensure that the TFV-Zn particles would exhibit extended release into buffer, because the crystal and coating are formed entirely of non-covalent interactions. When compared to a solution of free TFV, the particles exhibited much slower release (FIG. 12) from 100 kDa dialysis membranes (about 40% over 24 h).

Next, TFV-Zn particles were formulated using either F127 or PVA coatings. As seen in Table 10, the presence of the coatings stabilized the particles, as evidenced by the smaller average size and decreased polydispersity. The presence of the coatings on the surface is also implied by the change in zeta potential toward a more neutral charge. Additionally, these particles were fluorescently labeled for imaging purposes, via covalent attachment of an Alexa Fluor® dye to the free amine on TFV. Crystals were found to be unstable when made at a ratio of 1:50 labeled: unlabeled TFV, but were stable and visible via fluorescent microscopy at a ratio of 1:200 labeled:unlabeled TFV.

TABLE 10

Size and zeta potential of TFV particles

| Coating | MPP/CP | Size (nm) | ζ potential (mV) |
|---|---|---|---|
| 0.08% F127 | MPP | 154 ± 4 | −8.7 ± 1.6 |
| 0.1% PVA | CP | 165 ± 14 | −7.3 ± 0.4 |
| None | CP | 328 ± 91 | −21.5 ± 0.9 |

After obtaining stable, fluorescently labeled particles, it was determined whether the F127 coating would lead to improved particle distribution at a mucosal surface in animals, as was consistently seen with coated polymeric nanoparticles. TFV particles coated with either F127 or PVA were administered into the vaginas of mice, then the mice were sacrificed, their vaginas dissected out and flattened on a microscope slide, and imaged. As can be seen in FIGS. 13A-13B, F127-coated particles were well distributed over the entire vaginal surface, whereas the PVA-coated particles show incomplete coverage of the vaginal surface, evident as a "striping" behavior indicative of not entering the vaginal folds (rugae).

TABLE 11

HSV-2 Vaginal Challenge Results

| Group | Drug Form & Conc. | Vehicle | # Mice | # Infected | % Infected | p-value** |
|---|---|---|---|---|---|---|
| 1 | Placebo | PBS | 100 | 88 | 88.0 | <0.000001 |
| 2 | Soluble ACV(1 mg/mL) | PBS | 25 | 21 | 84.0 | 0.002 |
| 3 | Soluble ACV(10 mg/mL) | PBS | 100 | 62 | 62.0 | 0.10 |
| 4 | Soluble ACV(10 mg/mL) | Water | 75 | 52 | 69.3 | 0.02 |
| 5 | ACV-MPP(1 mg/mL)* | Water | 45 | 21 | 46.7 | N/A |

*Size 65.3 ± 10 nm, ζ potential −6.3 ± 1.0 mV.
**p-value vs. ACV-MPP.

Next MPP particles were produced using acyclovir monophosphate (ACVp) for use in testing the potential efficacy of MPP particles in preventing infection with the Herpes Simplex Virus Type 2 (HSV-2). ACVp is not dependent on viral thymidine kinase for the initial phosphorylation step that can lead to viral resistance. This also gives ACVp anti-HIV activity, although at low potency.

Female 6-8 week old CF-1 mice were subcutaneously injected with medroxyprogesterone acetate, and one week later received 20 μL of test agent or PBS intravaginally with a fire-polished positive displacement capillary pipette (Wiretrol, Drummond Scientific). Thirty minutes later, mice were challenged with 10 uL of inoculum containing HSV-2 strain G (ATCC #VR-734, $2.8\times10^7$ $TCID_{50}$ per mL). HSV-2 was diluted 10-fold with Bartel's medium to deliver 10 $ID_{50}$, a dose that typically infects ~85% of control mice. Mice were assessed for infection three days later after inoculation by culturing a PBS vaginal lavage on human foreskin fibroblasts (Diagnostic Hybrids, MRHF Lot #440318W), as described previously (Cone R A et al., BMC Infect Dis 6:90, 2006). In this model, input (challenge) virus is no longer detectable in lavage fluid if it is collected more than 12 hours after the challenge.

It was found that ACVp particles could be prepared in the presence of zinc, via similar interactions as TFV (phosphate group and purine ring). Soluble ACVp or ACVp in the form of MPP nanocrystals was administered to mice 30 min prior to challenge with live HSV. Both the drug and the virus were administered intravaginally. Soluble drug administered at the same concentration as the MPP-drug was ineffective (84% infected compared to 88% of controls), whereas only 46.7% of mice in the MPP-drug group were infected. Groups of mice given soluble drug at 10-times the dose given of MPP-drug were infected at a rate of 62% (drug in PBS) or 69.3% (drug in water). Comparing soluble drug to MPP-drug administered in the same vehicle (pure water), soluble drug was less protective (p=0.02) even at 10-times higher concentration than MPP-drug.

It is noted that stable nanocrystals of drugs with a free phosphate group can be formed with Zn using both freeze-drying approaches and sonication procedures. For freeze drying, the drug was dissolved in an aqueous solution of F127. An amount of zinc acetate was added in the range of 1:50 to 1:5 (Zn: drug), and the solution immediately flash frozen. The dried powder was reconstituted in water at the desired concentration. F127 concentrations both above (1%) and below (0.08%) the critical micelle concentration (CMC) of F127 can be used to make stable TFV nanocrystals. However, the ACVp nanocrystals were much more sensitive to surfactant concentration. Stable nanocrystals could only be formed when using F127 concentrations below the CMC (~0.1%). F127 concentrations above the CMC caused significant aggregation and sedimentation of the ACVp nanocrystals, regardless of the formulation method tested.

Additionally, stable nanocrystals can be formed by adding excess zinc acetate to drug solution. The precipitate is washed 3+ times by centrifugation. The resultant slurry is sonicated using a probe sonicator (without surfactant; bubbling causes aggregation and instability). Other methods, such as milling, may also work. Surfactant is then added to stabilize the resultant nanocrystals. Without the presence of surfactant, significant aggregation and sedimentation occurs. Using this formulation technique, stable TFV nanocrystals could be made using F127 concentrations up to, for example, 1%. Similarly, in these experiments, stable ACVp nanocrystals could only be formed using F127 concentrations below the CMC (typically using 0.08%).

In Examples 4-6, undiluted cervicovaginal secretions were collected from women with normal vaginal flora using a self-sampling menstrual collection device following a protocol approved by the Institutional Review Board of the Johns Hopkins University. The device was inserted into the vagina for ~30 s, removed, and placed into a 50 mL centrifuge tube. Samples were centrifuged at 1,000 rpm for 2 min to collect the mucus secretions.

In Examples 4-6, particle transport rates were measured by analyzing trajectories of fluorescent or fluorescently labeled particles, recorded using an electron multiplying charge coupled device (EMCCD) camera (Evolve 512, Photometrics, Tucson, Ariz.) mounted on an inverted epifluorescence microscope (Zeiss, Thornwood, N.Y.) equipped with a 100× oil-immersion objective (N.A., 1.46) and the appropriate filters. Experiments were carried out in custom-made chamber slides, where diluted particle solutions (0.0082% wt/vol) were added to 20 µL of fresh mucus to a final concentration of 3% v/v (final particle concentration, 8.25×10−7 wt/vol) and stablized at room temperature before microscopy. Trajectories of n≥100 particles were analyzed for each experiment, and at least three independent experiments were performed for each condition. Movies were captured with MetaMorph software (Universal Imaging, Glendale, Wis.) at a temporal resolution of 66.7 ms for 20 s. The tracking resolution was 10 nm, as determined by tracking the displacements of particles immobilized with a strong adhesive. The coordinates of nanoparticle centroids were transformed into time-averaged MSD, calculated as $<\Delta r2(\tau)>=[x(t+\tau)-x(t)]^2+[y(t+\tau)-y(t)]^2$, where x and y represent the nanoparticle coordinates at a given time and τ is the time scale or time lag. Distributions of MSDs and effective diffusivities were calculated from this data. Particle penetration into a mucus layer was modeled using Fick's second law and diffusion coefficients obtained from tracking experiments.

Example 7

This example describes the development of mucus-penetrating particles that improve drug delivery to the mucosal surface of the mouse vagina.

Improved methods for sustained and more uniform drug delivery to the vagina may provide more effective prevention and treatment of conditions that impact women's health, such as cervical cancer, bacterial vaginosis, and sexually transmitted infections. For example, women are disproportionately infected with HIV, partly owing to a lack of female-controlled prevention methods. An easily administered, discreet, and effective method for protecting women against vaginal HIV transmission could prevent millions of infections worldwide. However, vaginal folds, or "rugae", that accommodate expansion during intercourse and child birth, are typically collapsed by intra-abdominal pressure, making the surfaces of these folds less accessible to drugs and drug carriers. Poor distribution into the vaginal folds, even after simulated intercourse, has been cited as a critical factor for failure to protect susceptible vaginal surfaces from infection. Distribution over the entire susceptible target surface has been proven important for preventing and treating infections. Additionally, to increase user acceptability, drug delivered to the vagina should be retained in the vaginal tract at effective concentrations over extended periods of time. Achieving sustained local drug concentrations is challenging because the vaginal epithelium is highly permeable to small molecules and also because soluble drug dosage forms (gels, creams) can be expelled by intra-abdominal pressure and ambulation. Lastly, drug delivery methods must be safe and non-toxic to the vaginal epithelium. Improvements in the distribution, retention, and safety profile of vaginal dosage forms may lead to a substantial increase in efficacy and decrease in the side effects caused by largely ineffective systemic treatments for cervicovaginal infections and diseases.

Nanoparticles have received considerable attention owing to their ability to provide sustained local drug delivery to the vagina. However, the mucus layer coating the vaginal epithelium presents a barrier to achieving uniform distribution and prolonged retention in the vaginal tract. Mucus efficiently traps most particulates, including conventional polymeric nanoparticles (CPs), through both adhesive and steric interactions. The efficiency with which mucus traps foreign pathogens and particulates implies that CPs would become trapped immediately upon contact with the lumenal mucus layer, preventing penetration into and, thus protection of, the rugae. Particles and pathogens trapped in the superficial lumenal mucus layer would be expected to be rapidly cleared from the tissue, limiting the retention time of mucoadhesive materials, such as CP.

By mimicking viruses that have evolved to penetrate the mucus barrier to establish infection, mucus-penetrating particles (MPPs) were recently engineered for mucosal drug delivery by coating CPs with an exceptionally high density of low molecular weight poly(ethylene glycol) (PEG). MPPs diffuse through human cervicovaginal mucus (CVM) at speeds comparable to their theoretical diffusion through water. Here, it was sought to test the hypothesis that MPPs would provide enhanced distribution and increased retention in vivo in the vagina by penetrating into the deepest mucus layers, including the more slowly cleared mucus in the rugae, thereby releasing drug in the optimal location for efficient tissue uptake (FIG. 14E). In addition to the common progestin-induced diestrus phase (DP) mouse model, the use of an estradiol-induced estrus phase (IE) mouse model is introduced in which the mouse CVM (mCVM) more closely mimics human CVM (hCVM) and, therefore, provides a more human-like model for developing and translating MPPs for human use.

Carboxylic acid-coated, fluorescent polystyrene nanoparticles (PS-COOH) were made into MPPs by covalently attaching a dense coating of low molecular weight PEG, as previously reported (Wang Y Y et al. Angew Chem Int Ed Engl 47:9726-9729, 2008; Lai S K et al. Proc Natl Acad Sci USA 104:1482-1487, 2007). Additionally, biodegradable MPPs (BD-MPP) were formulated with a poly(lactic-co-glycolic acid) (PLGA) core and a physically adsorbed PEG coating, as previously reported (Yang M et al. Angew Chem Int Ed Engl 50:2597-2600, 2011), because biodegradable particles can be loaded with drugs and are suitable for dosing to humans. PS-COOH and PLGA nanoparticles have a highly negative surface charge, which is nearly neutralized when densely coated with PEG. Nanoparticles were determined to be well-coated by measuring zeta potential (Table 12) as described previously (Lai S K et al. 2007). A zeta potential more neutral than −10 mV was previously found to be necessary for mucus-penetrating properties in hCVM (Wang Y Y et al, 2008). To ensure that MPPs were mucus-penetrating in native estrus phase mCVM, the particles were administered intravaginally to mice in the estrus phase. The entire vagina was then excised and opened to visualize the motions of hundreds of individual particles with a multiple particle tracking (MPT) method (Suh J et al. Adv Drug Deliv Rev 57:63-78, 2005). Particle trajectories for MPPs were indicative of rapid diffusion through watery pores in the mCVM, whereas motions of uncoated PS-COOH nanoparticles (CPs) were smaller than the particle diameter (~100 nm) (FIG. 14A). The ensemble averaged mean squared displacement (<MSD>) of MPPs in mCVM was found to be comparable to that reported for MPPs in hCVM (Lai S K et al. Proc Natl Acad Sci USA 107:598-603, 2010) (FIG. 14B), corresponding to ensemble averaged effective diffusivity (<Deff>) only ~8-fold slower than the theoretical diffusion of 110 nm particles in water (~4 µm$^2$/s).

TABLE 12

Particle characterization. Size, zeta potential, and polydispersity index (PDI) for all particle formulations.

| Particle type | Size (nm) | ζ potential (mV) | PDI |
|---|---|---|---|
| PSPEG (MPP) | 112 ± 3 | −4.2 ± 0.6 | 0.03 |
| PS (CP) | 87 ± 4 | −39.0 ± 2.4 | 0.10 |
| PLGA/F127 (BD-MPP) | 152 ± 6 | −4.2 ± 0.3 | 0.06 |
| PLGA/PVA (BD-CP) | 161 ± 15 | −6.7 ± 0.1 | 0.06 |
| ACVp-MPP | 65.3 ± 10 | −6.3 ± 1.0 | 0.37 |

Based on the measured $D_{eff}$ for individual particles, it was estimated with Fick's Second Law of Diffusion that about half of the MPP would diffuse through a 100 µm-thick layer of mCVM in about 4 h (FIG. 14D), whereas even after 24 h there would be no appreciable penetration by CPs. $D_{eff}$ values for CPs at a time scale of 1 s corresponded to MSD values less than the particle diameter (dotted line, FIG. 14C), likely revealing thermal fluctuation of particles stuck to mucin fibers and not particle diffusion. Overall, the transport behavior of both MPPs and CPs in estrus phase mCVM was very similar to their transport behavior in hCVM.

Figure 15A:
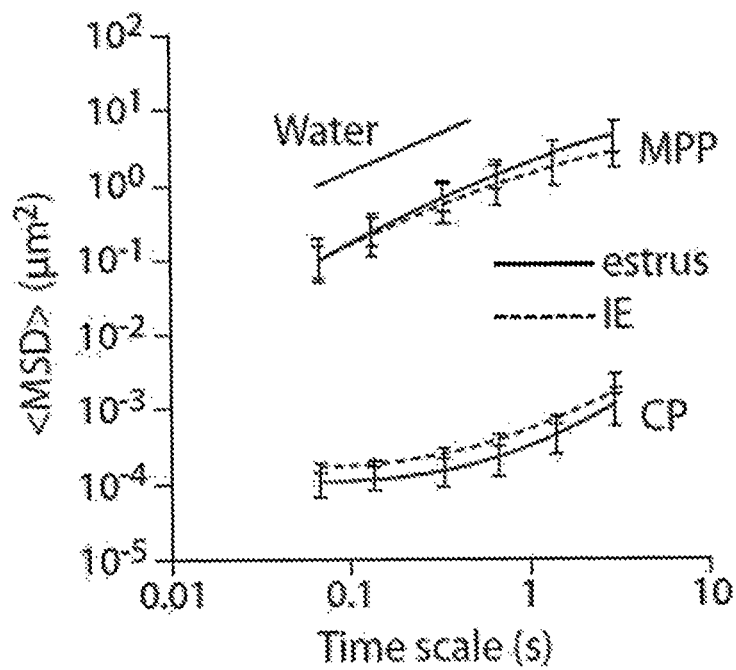
FIGS. 15A-15B are plots showing the transport of nanoparticles on IE mouse vaginal tissue. Ensemble-averaged geometric mean squared displacements (<MDS>) as a function of time scale.
Figure 15B:
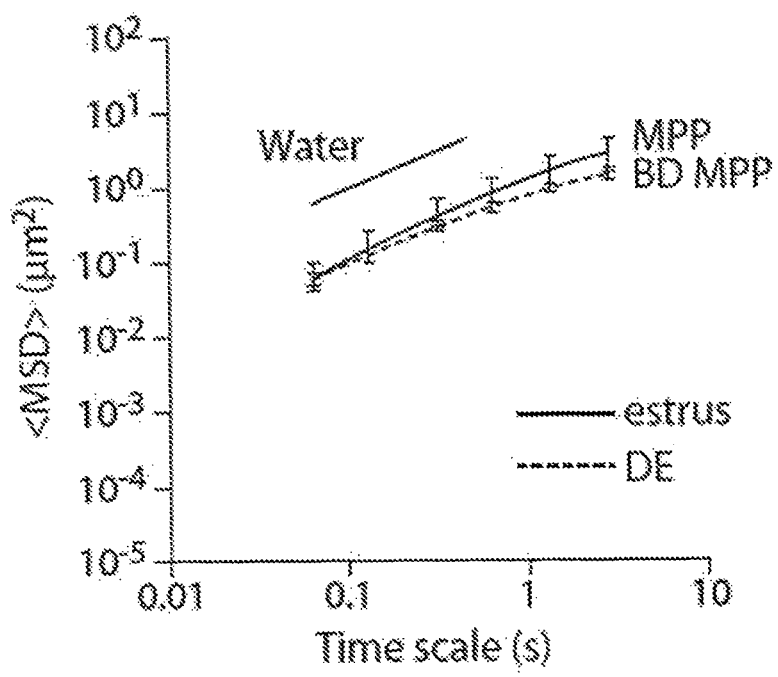

Synchronizing a large number of mice in the estrus phase for retention studies required hormonal treatment. Particle transport behavior was tested in IE mice to confirm that estradiol treatment, which has been used routinely for inducing estrus-like behavior in many animal models (Ring J R, Endocrinology 34:269-275, 1944; Rubio C A, Anat Rec 185:359-372, 1976), did not alter MPP and CP transport behavior prior to distribution and retention studies (FIG. 15A). Additionally, BD-MPP transport behavior was indistinguishable from MPP in IE mucus (FIG. 15B).

Figure 16:
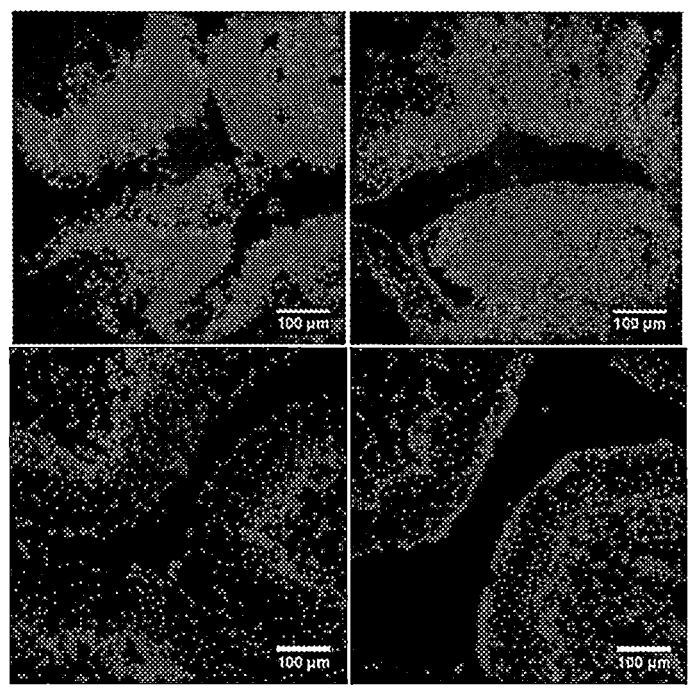
FIG. 16 includes images illustrating particle distribution in the mouse vagina. Distribution of red fluorescent non-biodegradable and biodegradable CPs and MPPs in transverse cryosections of estrus phase and IE mouse vaginal tissue. Images are representative of n≥3 mice.

It was next investigated in the estrus phase mouse and IE mouse whether the ability to rapidly penetrate mucus would lead to more rapid and uniform vaginal distribution of MPPs compared to CPs. MPPs and CPs were applied in hypotonic media to mimic the way osmotically driven water flux (advective transport) rapidly transports nutrients from the intestinal lumen to the brush border epithelial surface. Ten minutes after particle administration, the entire vagina was dissected out and stained for cell nuclei. CPs aggregated in the lumenal mucus and did not penetrate into the vaginal rugae (FIG. 16). In contrast, MPPs formed a continuous particle layer that coated the entire vaginal epithelium, including all the surfaces of the rugae. MPPs penetrated more than ~100 µm of mucus via advection within 10 min compared to the ~4 hours it would take them to diffuse that distance through mucus (FIG. 14D). This behavior was also consistent for BD-CPs and BD-MPPs, and CPs and MPPs administered to IE mice (FIG. 16). Videos illustrating the movement of MPPs through hCVM past muco-adhesive CPs can be found in Video 1 (no flow, diffusion) and Video 2 (with flow, advection).

Figure 17:
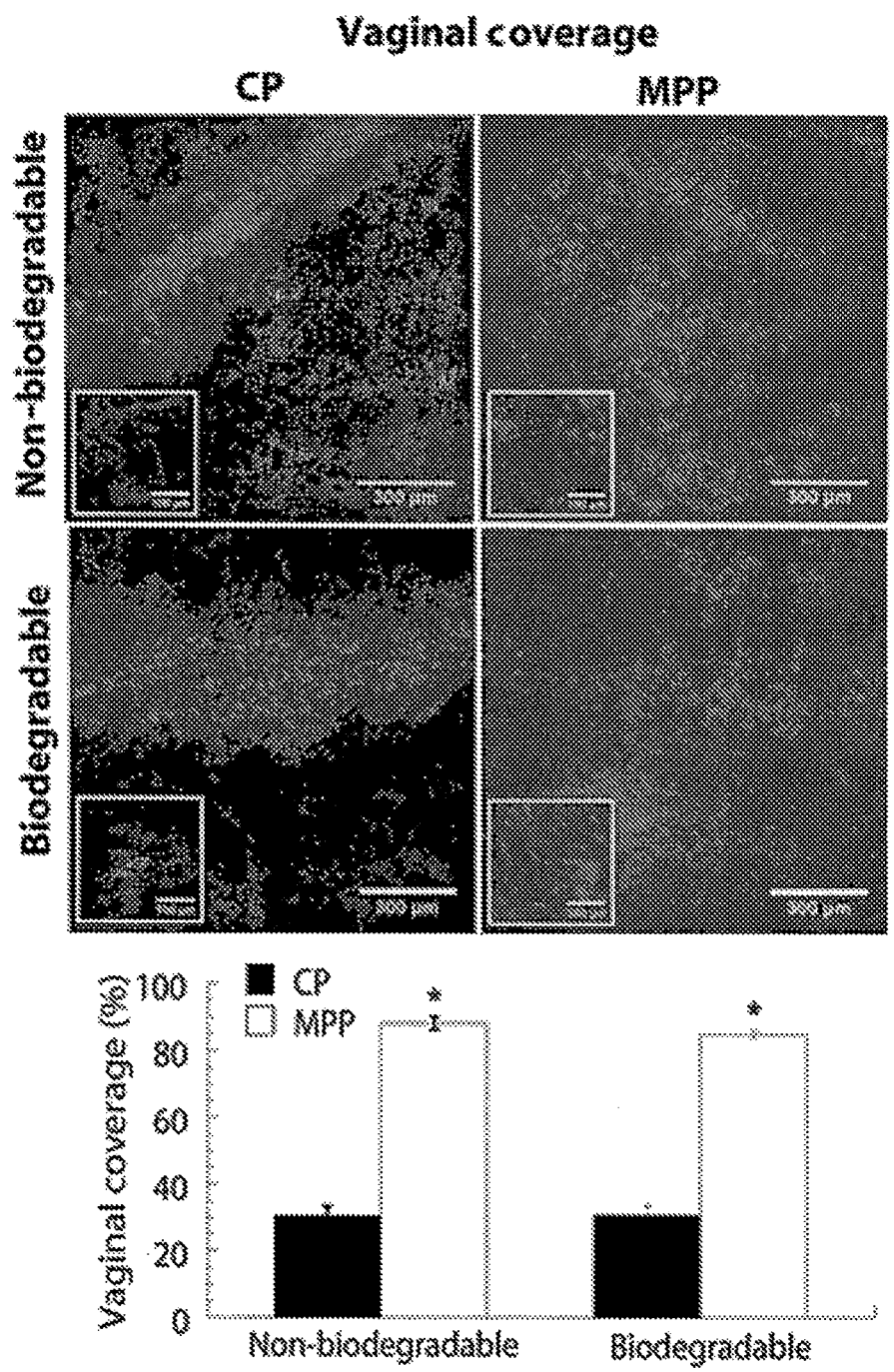
FIG. 17 includes images and plots showing the quantification of vaginal nanoparticle coverage. Distribution of red fluorescent non-biodegradable and biodegradable CPs and MPPs on flattened estrus phase mouse vaginal tissue. Insets are images of dark areas at higher magnification. Images are representative of the averages calculated for n≥3 mice. Data are means±SEM. *P<0.05, Student's t test.
Figure 18:
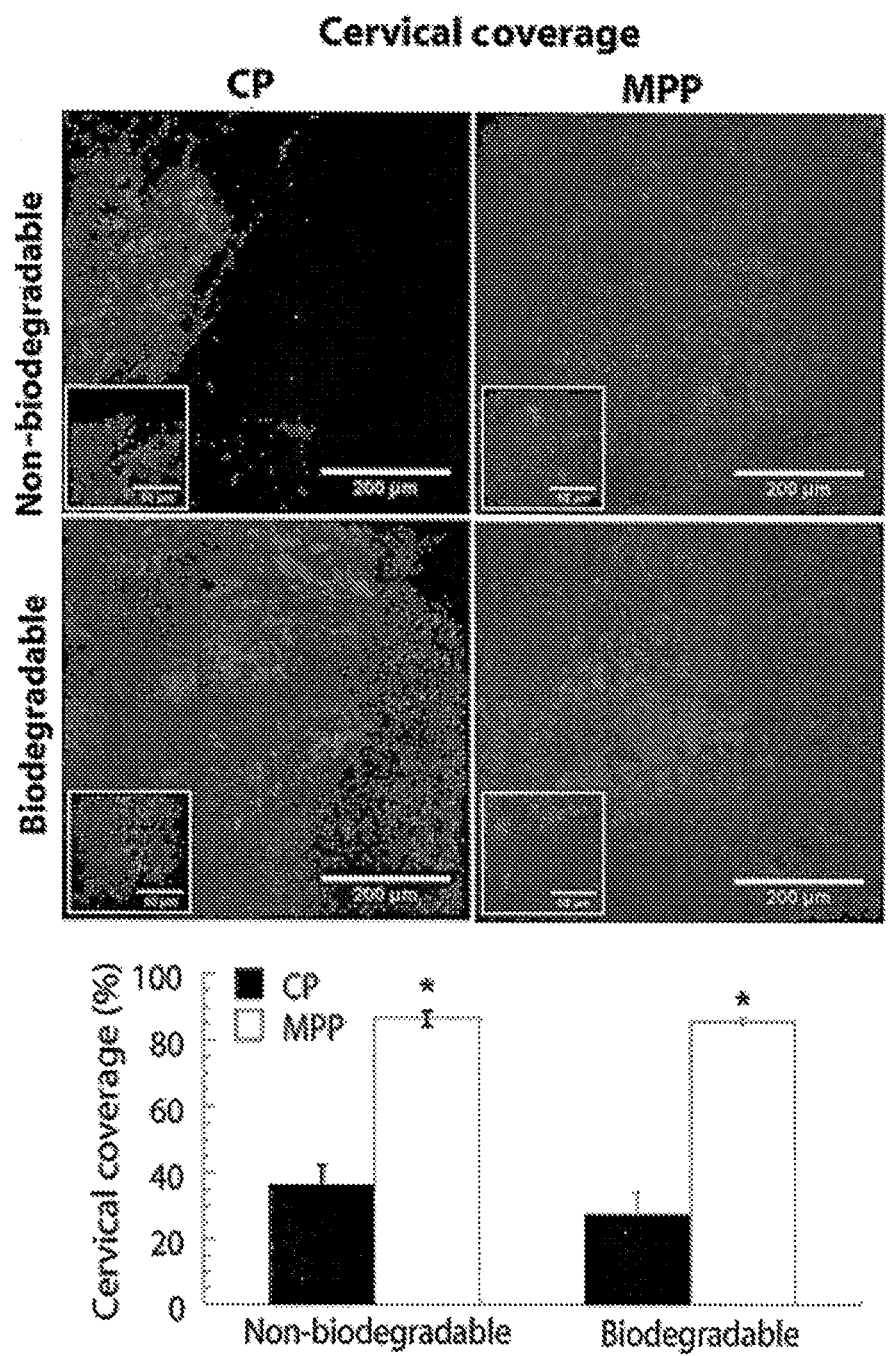
FIG. 18 includes images showing the cervical nanoparticle coverage. Cervical distribution of red fluorescent non-biodegradable and biodegradable CPs and MPPs on estrus phase mouse cervical tissue. Insets are images of dark areas at higher magnification. Images are representative of n≥3 mice. Data are means±SEM. *P<0.05, Student's t test.

To quantify the difference in distribution of MPPs and CPs, fluorescent images were obtained of freshly excised, opened, and flattened mouse vaginal tissue. As can be seen in FIG. 17, the adhesion of CPs to lumenal vaginal mucus layers created "stripes" of mucus with particles alternating with dark "stripes" of mucus without particles, the latter corresponding to the rugae that were opened when the vaginal tissue was flattened. In contrast, transport of MPPs toward the epithelium and into the rugae created a continuous particle coating on the flattened vaginal surface (FIG. 17). Quantification of the fluorescence on the vaginal and cervical tissue indicated that 88% of the flattened vaginal surface and 87% of the cervical surface were densely coated with MPPs, whereas only 30% of the vaginal surface and 36% of the cervical surface were coated with CPs. Upon further inspection at higher magnification of darker areas of the vaginal and cervical surfaces, a continuous less-concentrated coating of MPPs was seen (FIGS. 17-18, insets), implying that there was nearly complete coverage of the vaginal and cervical epithelium. For CPs, a less-concentrated coating was not found at higher magnification (FIGS. 17-18, insets). Similar trends were found with BD-MPPs, with 85% vaginal coverage and 86% cervical coverage, as well as BD-CPs with 31% vaginal coverage and 27% cervical coverage (FIGS. 17-18).

Figure 22:
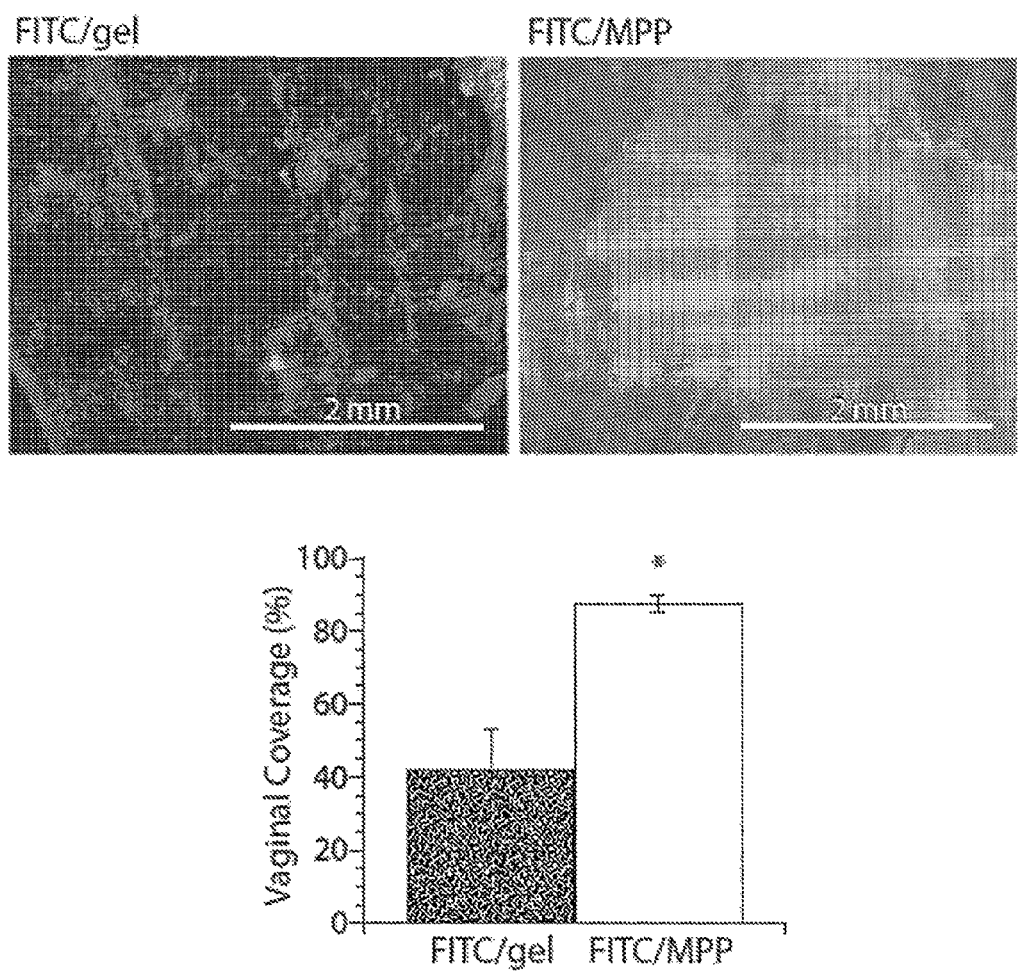
FIG. 22 includes images showing the distribution and retention of a model drug, FITC, in the estrus mouse vagina delivered in gel form or encapsulated in biodegradable MPPs. Fluorescent images were taken of flattened mouse vaginal tissue after 24 h. Images are representative of n≥3 mice. Data are means±SEM. *P<0.05, Student's t test.

It was then sought to determine whether the improved distribution of BD-MPP could improve the delivery of small molecules as compared to a gel dosage form. Lipophilic molecules are likely to enter the first epithelial surface they contact, failing to contact cells in the rugae. Conversely, hydrophilic molecules can diffuse rapidly through the vaginal epithelium and be carried away by blood and lymph circulation leading to brief periods of coverage. BD-MPP was loaded with a fluorescent, water-soluble small molecule, fluorescein isothiocyanate (FITC), as a model drug (FITC/MPP). To mimic conventional vaginal delivery, soluble FITC (FITC/gel) was administered in the universal vaginal placebo gel hydroxyethylcellulose (HEC). Twenty-four hours after administration to estrus phase mice, the vaginal tissues were excised and flattened to expose the vaginal folds. Patches of FITC coated 42% of the vaginal surface when administered as FITC/gel, whereas FITC/MPP provided a well-retained FITC coating of 87% of the vaginal surface (FIG. 22), even 24 h after particle administration.

Figure 19:
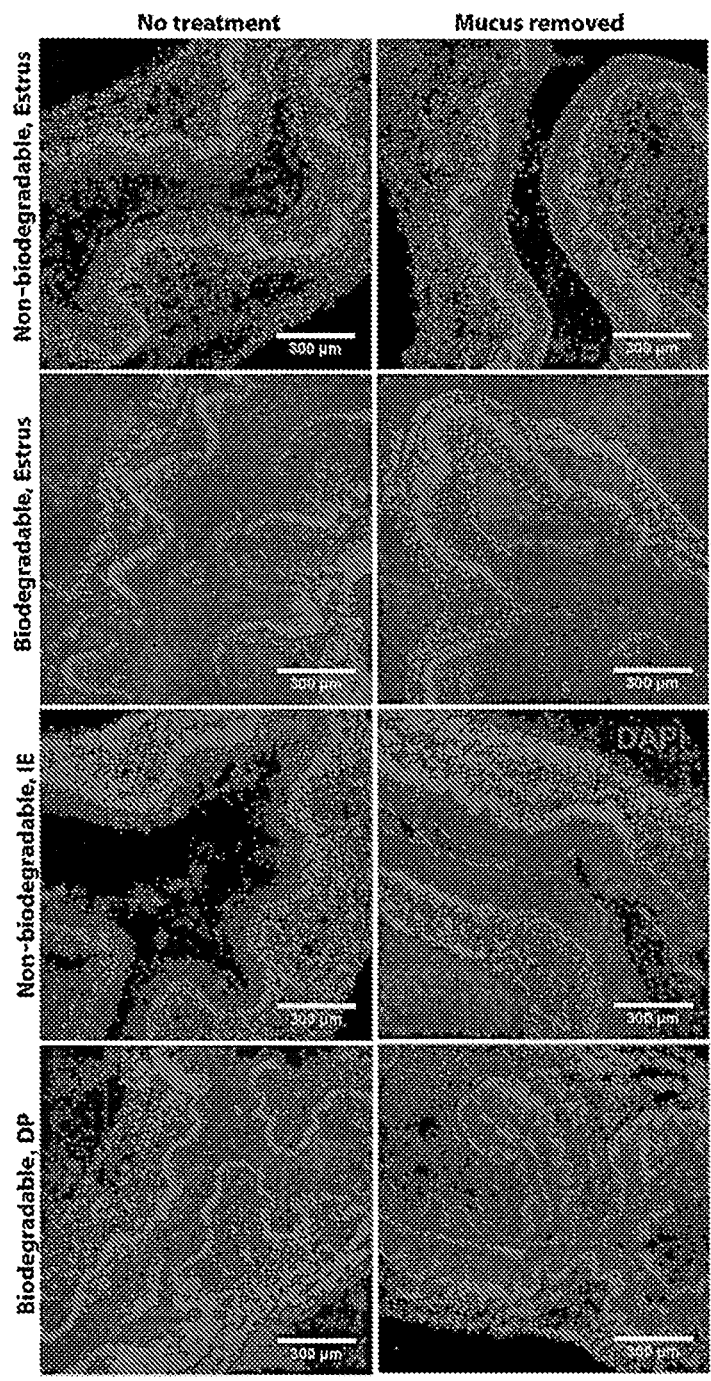
FIG. 19 includes images showing the effects of mucus removal on mucoadhesive nanoparticles. Distribution of red fluorescent non-biodegradable and biodegradable CPs in transverse cryosections of mouse vaginal tissue with either an intact mucus layer (No treatment) or mucus removed by lavage and swabbing (Mucus removed). Images are representative of n≥3 mice.
Figure 20:
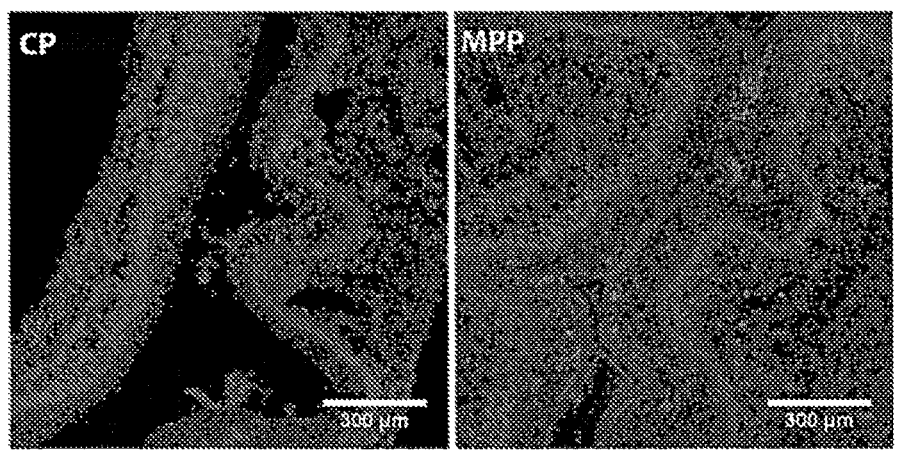
FIG. 20 includes images showing the particle distribution in the IE mouse vagina. Distribution of red fluorescent non-biodegradable CP and MPP in transverse cryosections of IE mouse vaginal tissue. Images are representative of n≥3 mice.

To further characterize the effects of the mucus barrier, we found that removing vaginal mucus by lavage (Cu Y et al., J Cont Rel 156:258-64, 2011; Woodrow K A et al. Nat Mater 8:526-33, 2009) prior to particle administration markedly improved CP distribution, indicating that their mucoadhesive character prevents uniform distribution in the vagina (FIG. 19).

It was next sought to determine vaginal retention of MPPs compared to mucoadhesive CPs using our IE model. Fluorescent MPPs and CPs were administered intravaginally to IE mice. At specified time points, the entire reproductive tract (vagina and uterine horns) was excised and analyzed quantitatively with fluorescence imaging (FIG. 21A). After an initial decrease in particle fluorescence that was similar for MPP and CP (likely owing to initial "squeeze out" preceding mucus penetration), the remaining amount of MPPs stayed constant at roughly 60% (FIG. 21B). In contrast, the amount of CPs steadily decreased with time to 10% (6 h). Importantly, although CPs were distributed along the length of the vagina, this longitudinal coverage does not indicate that the CP penetrated mucus to reach the epithelium, nor surfaces inside the vaginal folds, as shown in FIG. 16.

The immune system is highly active at mucosal surfaces (Mestecky O P et al. Mucosal Immunology. Elsevier Academic Press, Burlington, ed. Third, 2005), especially those with surfaces covered with living cells, such as columnar epithelia in the endocervix in humans. Inflammatory effects of nanoparticles were investigated using mice pre-treated with Depo-Provera, a long-acting progestin treatment that synchronizes mice in the diestrus phase, during which the vaginal epithelium thins and becomes covered with living cells. In contrast, in estrus, the mouse vagina thickens from 4 to 7 cell layers to about 12 cell layers and the epithelial surface is protected with many layers of dead and dying cells (Biology of the laboratory mouse. Ed. G D Snell. Dover Publications, Inc., New York, 1956; J Am Pharml Assoc 45:819-819, 1956). Additionally, the progestin-induced diestrus phase (DP) mouse vaginal epithelium has an increased immune cell population, leading to enhanced acute inflammatory responses; whereas the estrus phase is characterized by an absence of immune cells (Hubscher C H et al. Biotech Histochem 80:79-87, 2005). Depo-Provera effectively synchronizes mice to a diestrus-like state for days to weeks, which is important for experiments lasting 24 h or longer.

Figure 23:
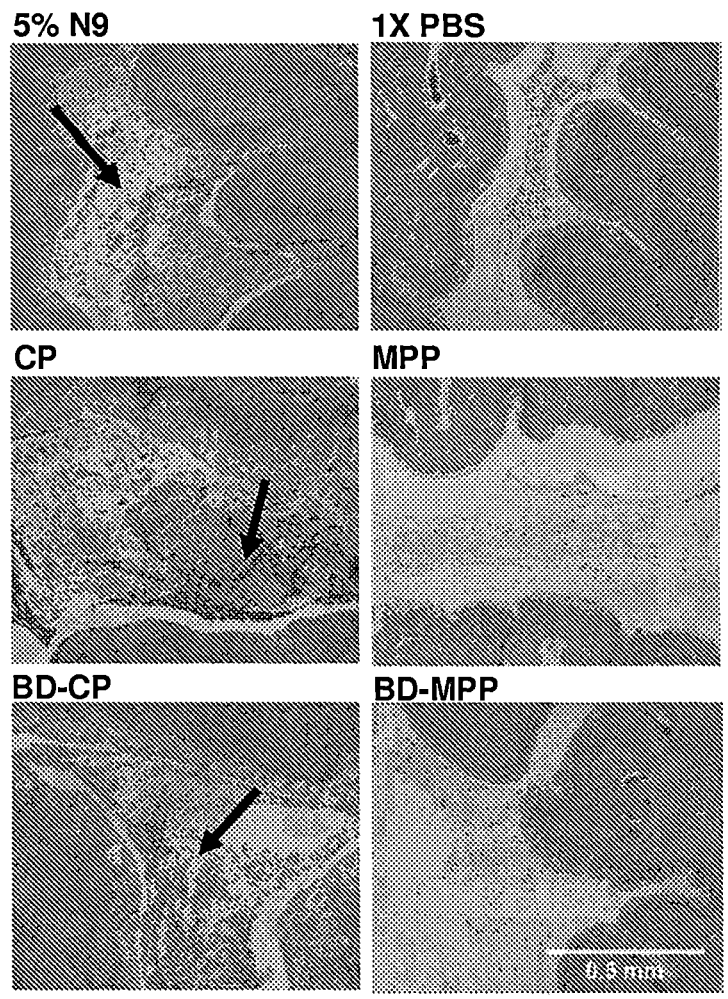
FIG. 23 includes images showing the acute toxicity and cytokine concentrations with daily administration. Hematoxylin and eosin (H&E)-stained cross-sections of mouse DP vaginal tissue excised 24 h after intravaginal administration of 5% N9, PBS, CPs, MPPs, BD-CPs, and BD-MPPs. Scale bar applies to all images. Arrowheads point to clusters of neutrophils. Images are representative of n≥5 mice.

Standard hematoxylin and eosin (H&E) staining was used to investigate potential toxic effects of intravaginally administered nanoparticles. Nonoxynol-9 (N9), a nonionic detergent known to cause vaginal toxicity (Ramjee G et al. AIDS 24 Suppl 4, S40-49. 2010), was used as a positive control, and PBS (saline) was used as a negative control. The same (BD-) MPPs and (BD-) CPs that were used for distribution and retention studies were tested for toxicity. As expected, N9 caused acute inflammation at 24 h that was not seen following PBS treatment (FIG. 23). CP, like N9, caused pronounced neutrophil infiltration into the lumen, but MPPs did not cause this inflammatory effect (FIG. 23, arrowheads).

Figure 24:
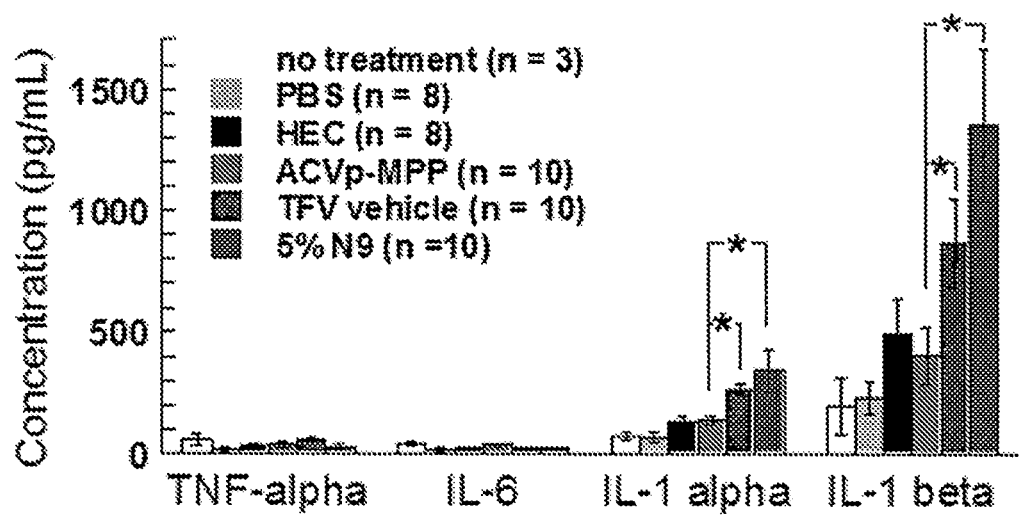
FIG. 24 is a plot showing the cytokine concentrations with daily administration. Cytokine concentrations in DP mouse cervicovaginal lavage (CVL) after daily vaginal treatments for 7 days. Data are means±SEM. *P<0.05, Student's t test.

Recent studies indicate that in response to certain vaginal products, the vaginal epithelium can secrete immune mediators that may enhance susceptibility to sexually transmitted infections (Cummins J E et al. Sex Transm Dis 36:S84-91, 2009; Wilson S S et al. Antivir Ther 14:1113-1124, 2009). Thus, it is important that a vaginal product not induce such an immune response, particularly after repeated dosing. Because our ultimate goal was to test MPPs for protection against HSV-2, we compared an MPP formulation containing acyclovir monophosphate (ACVp) to N9, HEC placebo gel, PBS, and a gel vehicle (TFV vehicle) used in recent tenofovir clinical trials. Nanoparticle and control formulations were administered vaginally to Depo Provera-treated mice daily for seven days. Vaginal lavages were collected on day 8 from each mouse and assessed for cytokines that have been found to be elevated in response to epithelial irritation: interleukin 1β (IL-1β), interleukin 1α (IL-1α), tumor necrosis factor α (TNF-α), and interleukin 6 (IL-6). It was found that both IL-1α and IL-1β levels were elevated in response to both the TFV vehicle and N9 solution (FIG. 24). This was not surprising in the case of N9 treatment, considering IL-1α and IL-1β are secreted by the vaginal epithelium in response to injury (Cummins J E et al., 2009). In contrast, the cytokine levels associated with ACVp-MPP were equivalent to the levels associated with HEC placebo gel (FIG. 24), which has been used in clinical trials without any associated increase in susceptibility to infection (Karim Q A et al. Science 329:1168-1174, 2010; Tien D et al. AIDS Res Hum Retroviruses 21:845-853, 2005). There was no detectable elevation of either IL-6 or TNF-α associated with any vaginal treatment as compared to untreated controls.

It was finally investigated whether the improved distribution, retention, and toxicity profile of MPPs would lead to improved protection against vaginal HSV-2 challenge in mice. Depo Provera treatment markedly increases the vaginal susceptibility of mice to infections, and candidate microbicides have provided only partial protection in the mouse model used here, even when administered immediately before the infectious inoculum (Achilles S L et al. Sex Transm Dis 29:655-664; 2002; Zeitlin L et al. Contraception 56:329-335, 1997). Moreover, several vaginal product excipients actually increase susceptibility to infection in this model (Cone R A et al., 2006; Moench T R et al. BMC Infect Dis 10:331, 2010). It was chosen to test ACVp for blocking vaginal transmission of HSV-2 infections, because acyclovir provides viral suppression in animals with repeated dosing multiple times per day (Kern E R, Am J Med 73, 100-108 (1982)). However, a single vaginal pretreatment with 50 mg/mL (5%) ACVp in guinea pigs resulted in 70% of animals infected compared to controls (Kern et al. Nucleos Nucleot Nucl 19:501-513, 2000). Therefore, ACVp provided a test case to determine whether MPP could significantly improve protection by a water-soluble and quickly metabolized drug by prolonging therapeutically relevant drug concentrations after a single application. Additionally, the mechanism of action of nucleotide analogs, such as ACVp, is prevention of intracellular viral replication, such that successful protection implies efficient uptake and retention in susceptible target cell populations in the vaginal and cervical mucosa.

ACVp nanoparticles were formulated with the same muco-inert coating used for all other studies. The size and ζ-potential of ACVp-MPP were similar to polystyrene (PS)-based MPP (Table 12). Mice were administered soluble ACVp or ACVp-MPP intravaginally 30 min prior to HSV-2 challenge. Soluble drug administered at the same concentration as the ACVp-MPP (1 mg/mL) was ineffective at protecting mice from viral infection (84.0% infected compared to 88.0% of controls), whereas only 46.7% of mice in the ACVp-MPP group were infected (Table 11). Groups of mice given soluble drug at 10-times the concentration in ACVp-MPPs were still infected at a rate of 62.0% (drug in PBS) or 69.3% (drug in water). Comparing soluble drug to ACVp-MPP in the same vehicle (pure water), soluble drug was significantly less protective, even at 10-fold higher concentration than ACVp-MPP (Table 11). To study the distribution and retention of nanoparticles at the vaginal mucosal surface and the effects of repeated dosing, 6-8 week old CF-1 mice (Harlan) were used. Mice were housed in a reversed light cycle facility (12 h light/12 h dark). For naturally cycling estrus, mice were selected for external estrus appearance and confirmed upon dissection (Champlin A K et al. Biol Reprod 8: 491-494, 1973; Allen E, Am J Anatomy 30:297-371, 1922). For hormonally induced estrus (IE), mice were acclimated for 3 weeks and injected subcutaneously with 100 µg of 17-β estradiol benzoate (Sigma) two days prior to the experiments. It has been demonstrated in numerous studies that treatment with estradiol induces an "estrus-like" state with analogous epithelial characteristics and vaginal cell populations (Rosa C G et al. Ann N Y Acad Sci 83:122-144, 1959; Rubio C A, Anat Rec 185:359-372, 1976; Gillgrass et al. J Virol 79:3107-3116, 2005). For vaginal toxicity and cytokine release, mice were injected subcutaneously with 2.5 mg of Depo-Provera (medroxyprogesterone acetate, 150 mg/mL) (Pharmacia & Upjohn Company) 7 days prior to the experiments.

Water was used as the hypotonic medium for all particle solutions. For ex vivo tracking, 5 µL of particles were administered intravaginally. After approximately 10 min, the vagina was removed and carefully sliced open to lay flat. The whole tissue was placed in a custom-made well-constructed such that a cover slip could be placed on top to contact the mucus without deforming the tissue. The well was a rectangle approximately 1 mm×0.5 mm cut out of three layers of electrical tape adhered to a standard glass slide. Cover slips were sealed around the edges with superglue and imaged immediately to prevent drying.

Mice were anesthetized prior to experimental procedures, including sacrifice by cervical dislocation. For all studies, mice were prevented from self-grooming by a collar of mildly adhesive tape around the abdomen, and from inter-grooming by housing in individual cages.

For conventional mucoadhesive particles (CPs), fluorescent, carboxyl (COOH)-modified polystyrene (PS) nanoparticles sized 100 nm (Molecular Probes) were used. These particles feature a negatively charged surface at neutral pH (Table 12). To produce mucus-penetrating particles (MPPs), CPs were covalently modified with 5-kDa amine-modified PEG (Creative PEGworks) via standard 1-ethyl-3-(3-dimethylaminopropyl) carbodiimide coupling reaction. Particle size and ξ-potential were determined by dynamic light scattering and laser Doppler anemometry, respectively, using a Zetasizer Nano ZS90 (Malvern Instruments). Size measurements were performed at 25° C. at a scattering angle of 90°. Samples were diluted in 10 mM NaCl solution (pH 7) and measurements performed according to instrument instructions. A near-neutral ξ-potential, measured by laser Doppler anemometry, was used to confirm PEG conjugation.

For biodegradable particles, PLGA acid 2A (50:50 Lakeshore Biomaterials), Lutrol F127 (BASF), and poly(vinyl alcohol) (PVA 25 kDa, Polysciences) were used. Alexa Fluor 555 was chemically conjugated to PLGA, which was used to produce nanoparticles by nanoprecipitation as described previously (Yang M et al. Angew Chem Int Ed Engl 50:2597-2600, 2011). Briefly, 10 mg/mL of labeled PLGA was dissolved in acetone or THF (with or without 2 mg FITC), and added dropwise to 40 mL of aqueous surfactant solution. After stirring for 2 h, particles were filtered through a 5-µm syringe filter and collected by centrifugation (Sorvall RC-6+, ThermoScientific) and washed. Particle size and ξ-potential were determined as described.

ACVp-MPPs were prepared by dissolving ACVp in ultrapure water containing Lutrol F127. Zinc acetate was added at a molar ratio of 5:1 ACVp:Zn, to chelate the ACVp and render it water insoluble, and then immediately flash frozen and lyophilized. Particle characterization was conducted after reconstitution. The powder was reconstituted with ultrapure water prior to administration, with a final concentration of 1 mg/mL ACVp and 0.8 mg/mL Lutrol. Soluble ACVp was titrated with NaOH as needed to reach pH to 6-7. Particle size and ξ-potential were determined as described.

The trajectories of the fluorescent particles in ex vivo vaginal tissue samples were recorded using a silicon-intensified target camera (VE-1000, Dage-MTI) mounted on an inverted epifluorescence microscope equipped with 100× oil-immersion objective (numerical aperture 1.3). Movies were captured with Metamorph software (Universal Imaging Corp.) at a temporal resolution of 66.7 ms for 20 s. Trajectories of n>130 particles were analyzed for each experiment, and three independent experiments were performed using tissue from different mice. The coordinates of particle centroids were transformed into time-averaged mean squared displacements (<MSD>), calculated as:

$$<\Delta r^2(\tau)>=[x(t+\tau)-x(t)]^2+[y(t+\tau)-y(t)]^2$$

where τ is time scale (or time lag), x and y are the corresponding particle coordinates at time t, and $\Delta r^2$ is the MSD. This equation was used to calculate particle MSDs and effective diffusivities ($D_{eff}$), as previously demonstrated (Lai S K et al. Proc Natl Acad Sci USA 104:1482-1487, 2007; Tang B C et al. Proc Natl Acad Sci USA 106:19268-19273, 2009). The calculated $D_{eff}$ values were used for modeling of particle penetration through a mucus slab, as described previously (Tang B C et al, 2009).

For distribution with mucus removal, prior to particle administration, mice were given 2× vaginal lavage with 50 µL of PBS followed by a single swab with a cotton-tipped applicator. Subsequently, 5 µL of either CPs or MPPs were administered intravaginally. The entire vagina was then removed and frozen in Tissue-Tek O.C.T. Compound (Sakura Finetek U.S.A., Inc.). Transverse sections were obtained at various points along the length of the tissue (between the introitus and the cervix) using a Microm HM 500 M Cryostat (Microm International). The thickness of the sections was set to 6 µm to achieve single cell layer thickness. The sections were then stained with ProLong Gold (Invitrogen) antifade reagent with DAPI to visualize cell nuclei and retain particle fluorescence. Fluorescent images of the sections were obtained with an inverted fluorescent microscope. To quantify nanoparticle distribution, 5 µL of either CPs or MPPs were administered intravaginally. Within 10 minutes, vaginal tissues, including a "blank" tissue with no particles administered, were sliced open longitudinally and clamped between two glass slides sealed shut with super glue. This procedure completely flattens the tissue, exposing the folds. The "blank" tissue was used to assess background tissue fluorescence levels to ensure that all images taken were well above background levels. Six fluorescent images at low magnification and at least one image at high magnification were taken for each tissue. The images were thresholded to draw boundaries around the fluorescent signal, and then the area covered quantified using ImageJ software. An average coverage was determined for each mouse, and then these values were averaged over a group of n≥3 mice. The cervix from each mouse was cut from the uterine horns and mounted using the same custom-made wells used for ex vivo particle tracking. The wells were sealed with a cover slip, and the background fluorescence levels determined using the blank tissue. One fluorescent image, constituting nearly the entire cervical surface, was taken at low magnification above tissue background levels. These images were thresholded in the same manner to determine the area covered with particles. At least one higher magnification image was taken for each tissue to show individual particles.

Advection of MPPs and CPs were visualized using a custom capillary tube setup. A flat capillary tube (0.4 mm×4 mm×50 mm; VitroCom) was attached to a 1 mL tuberculin syringe (Becton Dickinson) via a piece of flexible plastic tubing. The tubing was clamped to one end of the capillary tube, and sealed using silicone grease. The syringe and tubing were loaded with saline, followed by fresh, undiluted human CVM mixed with 3% (v/v) of ~500 nm uncoated (red fluorescent) and PEG-coated (green fluorescent) polystyrene beads (Invitrogen). PEG-coated beads were prepared as described above for the 100 nm MPP used in mouse studies. Approximately 80 µL of mucus was needed to fill the capillary tube, and care was taken to avoid introducing air bubbles. Time lapse videos showing the motions of MPP and CP within the capillary tube, with and without applied pressure, were recorded using a 40× objective on a Zeiss LSM 510 confocal microscope (Carl Zeiss MicroImaging, LLC).

FITC dye (Sigma-Aldrich) was mixed at 1 mg/mL in HEC gel kindly provided by T. Moench (Reprotect). Biodegradable MPP were prepared as described, loaded with FITC dye and suspended in 1% Lutrol F127. To evaluate distribution, 10 µL of either gel or particle solution was administered intravaginally. After 24 h, the vaginal tissue was removed and cut open to lie flat. The tissue was then mounted between two microscope slides and squeezed to flatten the rugae. A "blank" tissue was included to determine background autofluorescence from the vaginal tissue, to ensure that the exposure setting used was indicative of FITC presence. Fluorescent images of the dye distribution on the flattened tissue surface were obtained using a Nikon E600 inverted microscope equipped with a 2× objective. These images were thresholded in the same manner using ImageJ to determine the coverage area.

To evaluate nanoparticle retention, 5 µL of red fluorescent CPs or MPPs were administered intravaginally. Whole cervicovaginal tracts were obtained at 0, 2, 4, and 6 h and placed in a standard tissue culture dish. For each condition and time point, at n>7 mice were used. Fluorescence images of the tissues were obtained using the Xenogen IVIS Spectrum imaging device (Caliper Life Sciences). Quantification of fluorescent counts per unit area was calculated using the Xenogen Living Image 2.5 software.

Five µL of particles or control solutions were administered intravaginally to the DP mouse model. After 24 h, whole cervicovaginal tracts were obtained and fixed in 4% paraformaldehyde solution for 24 h. Tissues were placed in 70% ethanol and taken to the Johns Hopkins Reference Histology Laboratory for paraffin embedding and standard H&E staining.

Twenty µL of each test agent was administered intravaginally to the DP mouse model once-a-day for seven (7) days. HEC gel and N9 were provided by T. Moench (Reprotect), and TFV vehicle gel was kindly provided by C. Dezzutti (University of Pittsburgh). On the eighth day, each mouse was lavaged twice with 50 µL of PBS. Each lavage sample was diluted with an additional 200 µL of PBS and centrifuged to remove the mucus plug. Supernatant (200 µL) was removed and split into 50 µL for each of the four (IL-1β, IL-1α, TNF-α, and IL-6) Quantikine ELISA kits (R&D Systems, Inc.). ELISAs were conducted per the manufacturer's instructions.

All data are presented as a mean with standard error of the mean (SEM) indicated. Statistical significance was determined by a two-tailed, Student's t-test ($\alpha=0.05$) assuming unequal variance. In the case of HSV-2 challenge, statistical significance was determined using Fisher's exact test, two-tailed distribution.

The female reproductive tract is susceptible to a wide range of sexually transmitted infections (R. Mallipeddi, L. C. Rohan, Expert Opin Drug Deliv 7:37-48, 2010). Biological vulnerability, a lack of female-controlled prevention methods, and inability to negotiate condom use all contribute to male-to-female transmission worldwide (Mallipeddi, 2010; Ndesendo, V M et al. AAPS PharmSciTech 9:505-520, 2008). An easily administered, discreet, and effective method for protecting women against vaginal HIV, HSV-2, and other virus transmission could prevent millions of infections worldwide. After 11 unsuccessful microbicide trials, CAPRISA 004 was the first to demonstrate partial protection against HIV with a vaginally administered microbicide (tenofovir) in a gel formulation (Karim Q A et al. Science 329:1168-1174, 2010). An important difference between previous generation microbicides such as N9 and the current generation of microbicides is the site of action. Many current generation microbicides, such as nucleotide analogs tenofovir and acyclovir monophosphate, work intracellularly to inhibit viral replication, whereas previous generations directly inactivated pathogens in the vaginal lumen. However, some previous generation microbicides caused toxicity to the vaginal epithelium that increased susceptibility to infection (D'Cruz O J et al. J Antimicrob Chemo 57:411-423, 2006).

For vaginal drug delivery to be maximally effective, topically delivered drugs must be distributed uniformly, maintained at sufficiently high concentration, and remain in close proximity to the folded vaginal epithelium (rugae) and cervical mucosa. Several techniques have been used to observe distribution of gels and drugs following vaginal administration, such as MRI (Mauck C K et al. Contraception 77:195-204, 2008), gamma-scintigraphy (Mauck C K et al., 2008; Chatterton B E et al. Int J Pharm 271:137-143, 2004), colposcopy (Poelvoorde N et al. Eur J Pharm Biopharm 73:280-284, 2009), and fiber optics (Mauck C K et al, 2008). These techniques are adequate to observe gross distribution along the vaginal tract, but do not reveal entry into vaginal folds. Our work demonstrates that, although a topical treatment may be well-distributed longitudinally along the vaginal tract, much of the folded epithelium can be left untreated and unprotected. Such untreated surfaces could have contributed to recent failures of several candidate microbicides against HIV in clinical trials (Hendrix C W et al. Annu Rev Pharmacol Toxicol 49:349-375, 2009). Additionally, when a fluid or gel is administered to the vagina, it directly contacts the rapidly shed outer lumenal mucus layer. Mucoadhesive particles, such as CP, are trapped in this superficial mucus layer and thereby excluded from the rugae. In contrast, we demonstrated that MPPs are capable of penetrating deep into the mouse rugae and, when delivered hypotonically, provided complete coverage of the epithelium within only 10 minutes.

Diffusion of particles is not rapid enough to result in such a uniform epithelial coating within minutes. Diffusion over ~100 µm would take on the order of hours. However, the vaginal epithelium has a great capacity for fluid absorption induced by osmotic gradients. Absorption of water through the mucus barrier assists MPPs in rapidly reaching the entire epithelial surface by advection, where the drug payload can then be released for optimal tissue uptake. In contrast, water absorption was not beneficial for CP, because they became adhesively trapped and immobilized in the lumenal mucus (Video 2).

Inadequate retention of therapeutically active compounds in the vaginal tract is another limiting factor for vaginal protection. For example, many vaginal spermicides provide protection for no more than 1 h (Zaneveld L J D et al. J Androl 22:481-490, 2001). Other vaginal products are not well-retained even after 6 h (Omar R F et al. Contraception 77:447-455, 2008; N. Poelvoorde, 2009; Chatterton B E et al. Int J Pharm 271:137-143, 2004), necessitating repeated administration for adequate protection. Similarly, over 90% of CPs were shed from the vagina within 6 h because they did not penetrate deep into the mucus layers. In contrast, MPPs provided enhanced delivery of an encapsulated model drug (FITC) for at least 24 h, as compared to soluble drug in a gel formulation. Thus, MPPs may provide a means for achieving potent once-daily topical vaginal administration for treatments such as microbicides against sexually transmitted diseases.

In prior attempts to develop mucosal drug delivery systems for the vaginal tract, a variety of "pretreatments" have been used that diminish the mucus barrier. Administering fluids (Cu Y et al. J Control Release, (10.1016/j.jconrel.2011.06.036); Woodrow, K A et al. Nat Mater 8:526-533, 2009; Kanazawa T et al. Int J Pharm 360:164-170, 2008; Kanazawa T et al. J Pharm Pharmacol 61:1457-1463, 2009), swabs (Woodrow K A et al, 2008; Kask As et al. Vaccine 28:7483-7491, 2010), or degradative enzymes (Seavey M M et al. Vaccine 27:2342-2349, 2009) prior to administration of mucoadhesive delivery vehicles was likely essential to the drug or gene delivery achieved in these studies. Here, it was found that a lavage plus swab pretreatment markedly improved distribution of CPs in the vagina, allowing the particles to coat the epithelium similarly to MPP (FIG. 19). Barrier-removing pretreatments may be impractical for human use, and especially inappropriate for microbicides intended to prevent sexually transmitted diseases. Healthy CVM itself is a somewhat effective barrier to viral infections (Lai S K et al. J Virol 83:11196-11200, 2009). It was shown that effective epithelial coverage can be achieved by using MPPs without the need to degrade or remove the mucus barrier.

PEG coatings have been widely used in developing polymeric drug carriers that are not easily recognized by the immune system (Tang B C et al. Proc Natl Acad Sci USA 106: 19268-73, 2009). It was demonstrated that dense PEG coatings produce MPPs that rapidly penetrate mucus without causing inflammation in the mouse vaginal tract. In contrast, administration of uncoated CPs resulted in an acute inflammatory response similar to administration of N9. Additionally, cytokine levels associated with daily administration of MPPs were indistinguishable from HEC placebo gel. Elevated levels of IL-1α and IL-1β, which are associated with epithelial injury, occurred after daily dosing with both N9 and TFV vehicle gel. The tenofovir-containing version of this gel was shown to have complete protection against HIV in a tissue explant model, and complete protection occurred in spite of visible epithelial shedding (Rohan L C et al. PLoS One 5:e9310, 2010). Previous work suggests that glycerol in the TFV gel may be responsible for the observed toxicity in mice (Moench T R et al. BMC Infect Dis 10:331, 2010).

Mice are useful animal models for developing vaginal products, but there are key differences in vaginal physiology between mice and humans. First, the estrous cycle occurs over a 4 to 5 day period in contrast to the 28-day human menstrual cycle. Throughout the four stages of the mouse estrous cycle, substantial growth is followed by sloughing of the epithelium, whereas there is relatively little change in the human vaginal epithelium throughout the menstrual cycle (Smith B G et al. Am J Anat 54:27-85, 1934; Ildgruben A K et al. Obstet Gynecol 102:571-582, 2003). The late proestrus and early estrus phases of the mouse estrous cycle are the most similar to that of the human vaginal epithelium (Smith B G et al., 1934; Asscher A W et al. J Anat 90:547-552, 1956). In these stages, there is significant bacterial colonization, including a peak in the presence of lactobacilli (Cowley H M et al. Microb Ecol Health Dis 4:229-235 1991). Additionally, the estradiol influence causes active secretion of mucus (Cowley H M et al., 1991; Corbeil L B et al. Tissue Cell 17:53-68, 1985; Rosa C G et al. Ann N Y Acad Sci 83:122-144, 1959), which was found in mice is both penetrable by MPPs and cleared in a matter of hours, similar to humans. Thus, it is believed that the IE mouse model is a valuable model in addition to the commonly used DP model for investigating vaginal delivery methods. Estradiol can be used to synchronize mice in the estrus phase, but does not "arrest" them in estrus. They continue to cycle, whereas DP treatment can arrest mice in a diestrus-like phase for days to weeks (Kaushic C et al. J Virol 77:4558-4565, 2003).

Is has been shown that MPPs are capable of rapidly penetrating human cervicovaginal and mouse vaginal mucus and that MPPs significantly improve speed and uniformity of coverage and retention time compared to conventional mucoadhesive nanoparticles. CPs elicited acute inflammatory responses similar to a known irritant N9, but, similar to the placebo gel, MPP caused no detected inflammatory responses. Vaginally administered MPPs loaded with acyclovir monophosphate were more effective at protecting mice against vaginal HSV-2 infection than soluble drug, even at 10-fold higher soluble drug concentration. These results motivate further development of MPPs for safe and effective vaginal drug delivery, for prevention and treatment of sexually transmitted infections, contraception, and treatment of other cervicovaginal disorders.

Other Embodiments

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of" or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method of delivering a pharmaceutical agent across a mucosal barrier, the method comprising:
    delivering to the mucosal barrier a composition comprising a plurality of coated particles, wherein the coated particles comprise:
        a core particle comprising a solid pharmaceutical agent or a salt thereof, wherein the pharmaceutical agent or salt thereof constitutes at least 80 wt % of the core particle; and
        a coating comprising a surface-altering agent surrounding the core particle,
    wherein the surface-altering agent comprises a triblock copolymer comprising a hydrophilic block-hydrophobic block-hydrophilic block configuration, wherein the hydrophobic block has a molecular weight of at least 2 kDa, and the hydrophilic blocks constitute at least 15 wt % of the triblock copolymer,
    wherein the hydrophobic block associates with the surface of the core particle and renders the coated particle hydrophilic, and
    wherein the coated particles have a relative velocity of greater than 0.5 in mucus and pass through the mucosal barrier.

2. The method of claim 1, wherein the surface-altering agent is covalently attached to the core particles.

3. The method of claim 1, wherein the surface-altering agent is non-covalently adsorbed to the core particles.

4. The method of claim 1, wherein the surface-altering agent is present on the surfaces of the coated particles at a density of at least 0.001 molecules per nanometer squared.

5. The method of claim 1, wherein the hydrophilic blocks of the triblock copolymer constitute at least 30 wt % of the triblock copolymer.

6. The method of claim 1, wherein the hydrophilic block of the triblock copolymer comprises poly(ethylene oxide) or poly(ethylene glycol) or a derivative thereof.

7. The method of claim 1, wherein the hydrophobic block of the triblock copolymer is poly(propylene oxide).

8. The method of claim 1, wherein the triblock copolymer is poly(ethylene oxide)-poly(propylene oxide)-poly(ethylene oxide) or poly(ethylene glycol)-poly(propylene oxide)-poly(ethylene glycol).

9. The method of claim 6, wherein the poly(ethylene oxide) or poly(ethylene glycol) block has a molecular weight of at least 2 kDa.

10. The method of claim 7, wherein the poly(propylene oxide) block has a molecular weight of at least 3 kDa.

11. The method of claim 1, wherein each of the core particles comprises a crystalline pharmaceutical agent or a salt thereof.

12. The method of claim 1, wherein each of the core particles comprises an amorphous pharmaceutical agent or a salt thereof.

13. The method of claim 1, wherein each of the core particles comprises a salt of the solid pharmaceutical agent.

14. The method of claim 1, wherein the pharmaceutical agent is at least one of a therapeutic agent or a diagnostic agent.

15. The method of claim 1, wherein the pharmaceutical agent is at least one of a small molecule, a peptide, a peptidomimetic, a protein, a nucleic acid, or a lipid.

16. The method of claim 1, wherein the pharmaceutical agent or a salt thereof has an aqueous solubility of less than or equal to 0.1 mg/mL at 25° C.

17. The method of claim 1, wherein the coated particles have an average size of at least 20 nm and less than or equal to 1 μm.

18. The method of claim 1, wherein the coated particles diffuse through human cervicovaginal mucus at a diffusivity that is greater than 1/500 the diffusivity that the particles diffuse through water on a time scale of 1 second.

19. The method of claim 1, wherein the coated particles have a relative velocity of greater than 0.8 in mucus.

20. The method of claim 1, wherein the mucosal barrier is mucus or a mucosal membrane.

21. The method of claim 1, wherein the mucosal barrier is present in a mucosal tissue.

* * * * *